(12) United States Patent
Wagner et al.

(10) Patent No.: US 11,795,216 B2
(45) Date of Patent: Oct. 24, 2023

(54) ANTIBODIES NEUTRALIZING GM-CSF FOR USE IN THE TREATMENT OF RHEUMATOID ARTHRITIS OR AS ANALGESICS

(71) Applicant: Takeda Pharmaceutical Company Limited, Osaka (JP)

(72) Inventors: Thomas Wagner, Constance (DE); Malin Carlsson, Lund (DK); Margit Staum Kaltoft, Birkerod (DK)

(73) Assignee: Takeda Pharmaceutical Company Limited, Osaka (JP)

( * ) Notice: Subject to any disclaimer, the term of this patent is extended or adjusted under 35 U.S.C. 154(b) by 211 days.

(21) Appl. No.: 16/995,617

(22) Filed: Aug. 17, 2020

(65) Prior Publication Data
US 2021/0171620 A1 Jun. 10, 2021

Related U.S. Application Data

(63) Continuation of application No. 14/913,578, filed as application No. PCT/EP2014/068489 on Sep. 1, 2014, now Pat. No. 10,745,475.

(60) Provisional application No. 61/871,900, filed on Aug. 30, 2013, provisional application No. 61/871,904, filed on Aug. 30, 2013.

(51) Int. Cl.
*A61K 39/395* (2006.01)
*C07K 16/24* (2006.01)
*A61K 39/00* (2006.01)

(52) U.S. Cl.
CPC ........ *C07K 16/243* (2013.01); *A61K 39/3955* (2013.01); *A61K 2039/54* (2013.01); *C07K 2317/56* (2013.01); *C07K 2317/565* (2013.01); *C07K 2317/76* (2013.01)

(58) Field of Classification Search
CPC .............................. A61K 39/395; C07K 16/24
See application file for complete search history.

(56) References Cited

U.S. PATENT DOCUMENTS

| | | | |
|---|---|---|---|
| 4,297,344 A | 10/1981 | Schwinn et al. | |
| 4,783,441 A | 11/1988 | Thurow | |
| 4,812,557 A | 3/1989 | Yasushi et al. | |
| 4,816,567 A | 3/1989 | Cabilly et al. | |
| 5,098,893 A | 3/1992 | Franks et al. | |
| 5,580,856 A | 12/1996 | Prestrelski et al. | |
| 5,648,260 A | 7/1997 | Winter et al. | |
| 5,747,032 A | 5/1998 | Metcalf et al. | |
| 6,171,586 B1 | 1/2001 | Lam et al. | |
| 6,309,636 B1 | 10/2001 | do Couto et al. | |
| 6,685,940 B2 | 2/2004 | Andya et al. | |
| 6,689,869 B2 | 2/2004 | Waldmann et al. | |
| 6,846,634 B1 | 1/2005 | Tomlinson et al. | |
| 7,691,379 B2 | 4/2010 | Allan | |
| 7,741,450 B2 | 6/2010 | Sass et al. | |
| 7,807,155 B2 | 10/2010 | Di Padova et al. | |
| 8,017,748 B2 | 9/2011 | Raum et al. | |
| 8,318,168 B2 | 11/2012 | Sass et al. | |
| 8,623,364 B2 | 1/2014 | Sass et al. | |
| 9,919,051 B2 | 3/2018 | Urbig et al. | |
| 2001/0014326 A1 | 8/2001 | Andya et al. | |
| 2003/0138417 A1 | 7/2003 | Kaisheva et al. | |
| 2003/0180287 A1 | 9/2003 | Gombotz et al. | |
| 2003/0202972 A1 | 10/2003 | Andya et al. | |
| 2005/0271663 A1 | 12/2005 | Ignatovich et al. | |
| 2006/0088523 A1 | 4/2006 | Andya et al. | |
| 2006/0193850 A1 | 8/2006 | Warne et al. | |
| 2008/0206241 A1* | 8/2008 | Bebbington | ............ A61P 17/00 514/249 |
| 2008/0317757 A1 | 12/2008 | Nakajima | |
| 2009/0297532 A1 | 3/2009 | Raum et al. | |
| 2009/0274706 A1 | 11/2009 | Bebbington et al. | |
| 2011/0182905 A1 | 7/2011 | Takada et al. | |
| 2011/0189082 A1 | 8/2011 | Kirchner | |
| 2012/0230982 A1 | 9/2012 | Zhao et al. | |
| 2014/0086928 A1 | 3/2014 | Sass et al. | |
| 2015/0246969 A1 | 9/2015 | Hartle et al. | |

FOREIGN PATENT DOCUMENTS

| | | |
|---|---|---|
| CN | 1612689 A | 5/2005 |
| CN | 1711282 A | 12/2005 |
| CN | 101001645 A | 7/2007 |
| CN | 101184777 A | 5/2008 |
| CN | 101861336 A | 10/2010 |
| CO | 15063785 | 5/2014 |
| EA | 201590359 A1 | 8/2015 |

(Continued)

OTHER PUBLICATIONS

Barnard et al., "Sarcoidosis: immunology, rheumatic involvement, and therapeutics", Current Opinion in Rheumatology, vol. 13(1), p. 84-91, Jan. 2001.*
Alberts, et al., Molecular Biology of the Cell, 4th Edition, Garland Science, New York, 2002.
Altschul, et al., "Gapped BLAST and PSI-BLAST: a new generation of protein database search programs", Nucleic Acids Research, vol. 25, No. 17, pp. 3389-3402, 1997.
Amendment and Response to non-Final Office Action dated Sep. 14, 2017, filed Jan. 16, 2018 for U.S. Appl. No. 14/718,923, filed May 21, 2015, 18 pages.
Andoh et al., (2005). "Interleukin-17 augments tumor necrosis factor-alpha-induced granulocyte and granulocyte/macrophage colony-stimulating factor release from human colonic myofibroblasts"; J Gastroenterol., 40(8):802-10.

(Continued)

*Primary Examiner* — Xiaozhen Xie
(74) *Attorney, Agent, or Firm* — Morrison & Foerster LLP

(57) ABSTRACT

The invention relates to neutralizing antibodies of GM-CSF and compositions comprising the same for use in the treatment of inflammatory disorders such as rheumatoid arthritis according to specific dosing regimen. The invention relates also to neutralizing antibodies of GM-CSF and compositions comprising the same for use in the treatment of pain, e.g. pain experienced in inflammatory disorders such as rheumatoid arthritis, according to specific dosage regimen.

14 Claims, No Drawings

Specification includes a Sequence Listing.

(56) References Cited

FOREIGN PATENT DOCUMENTS

| | | | |
|---|---|---|---|
| EP | 0265384 A2 | 4/1988 | |
| EP | 0344957 A1 | 12/1989 | |
| EP | 0499161 A2 | 8/1992 | |
| EP | 1256348 A1 | 11/2002 | |
| EP | 1593690 A1 | 11/2005 | |
| EP | 1947178 A1 | 7/2008 | |
| EP | 2399604 A1 | 12/2011 | |
| JP | H11510170 A | 9/1999 | |
| JP | 2004-538287 A | 12/2004 | |
| JP | 2008-536505 A | 9/2008 | |
| JP | 2009-525986 A | 7/2009 | |
| JP | 2010-531306 A | 9/2010 | |
| JP | 2011-518886 A | 6/2011 | |
| JP | 2013-515754 A | 5/2013 | |
| JP | 6346389 B1 | 6/2018 | |
| KR | 2008-0005962 | 1/2008 | |
| KR | 2009-0110827 | 10/2009 | |
| WO | WO199704801 A1 | 2/1997 | |
| WO | WO199954440 A1 | 10/1999 | |
| WO | WO2003009817 A2 | 2/2003 | |
| WO | WO2003039485 A2 | 5/2003 | |
| WO | WO2003068924 A2 | 8/2003 | |
| WO | WO2006013107 A1 | 2/2006 | |
| WO | WO2006066088 A2 | 6/2006 | |
| WO | WO2006111353 A2 | 10/2006 | |
| WO | WO-2006111353 A2 * | 10/2006 | ........... A61K 39/395 |
| WO | WO2006122797 A2 | 11/2006 | |
| WO | WO2007049472 A1 | 5/2007 | |
| WO | WO2007092772 A2 | 8/2007 | |
| WO | WO2007092939 A2 | 8/2007 | |
| WO | WO2007110631 A1 | 10/2007 | |
| WO | WO2008064321 A2 | 5/2008 | |
| WO | WO2009002521 A2 | 12/2008 | |
| WO | WO2009038760 A2 | 3/2009 | |
| WO | WO2009064399 A1 | 5/2009 | |
| WO | WO2009133103 A1 | 11/2009 | |
| WO | WO2009134805 A2 | 11/2009 | |
| WO | WO2010071923 A1 | 7/2010 | |
| WO | WO2010128035 A1 | 11/2010 | |
| WO | WO2011017070 A1 | 2/2011 | |
| WO | WO2011080209 A2 | 7/2011 | |
| WO | WO2011104381 A2 | 9/2011 | |
| WO | WO2013053767 A1 | 4/2013 | |
| WO | WO2014044768 A1 | 3/2014 | |
| WO | WO2014068026 A1 | 5/2014 | |
| WO | WO2014068029 A1 | 5/2014 | |

OTHER PUBLICATIONS

Avanzi, et al., "M-07e Human Leukemic Factor-Dependent Cell Line Provides a Rapid and Sensitive Bioassay for the Human Cytokines GM-CSF and IL-3", Journal of Cellular Physiology, vol. 145, pp. 458-464, 1990.
Behrens et al., (2012). "First in Patient Study of Anti-GM-CSF Monoclonal Antibody (MOR103) in Active Rheumatoid Arthritis: Results of a Phase 1b/2a Randomized, Double-Blind, Placebo-Controlled Trial," Arthritis & Rheumatism, & Annual Scientific Meeting of the American-College-of-Rheumatology and Association-of-Rheumatology-He, 64(12):4171-4172.
Beiboer et al. (2000). "Guided selection of a pan carcinoma specific antibody reveals similar binding characteristics yet structural divergence between the original murine antibody and its human equivalent," J Mol Biol., 296(3):833-489.
Campbell et al., (1998). "Protection from collagen-induced arthritis in granulocyte-macrophage colony stimulating factor-deficient mice," J Immunol., 161:3639-44.
Carpenter, et al., "Rational Design of Stable Lyophilized Protein Formulations: Some Practical Advice", Pharmaceutical Research, vol. 14, No. 8, pp. 969-975, 1997.
Chabaud, et al., "Enhancing Effect of IL-17 on IL-1-Induced IL-6 and Leukemia Inhibitory Factor Production by Rheumatoid Arthritis Synoviocytes and Its Regulation by Th2 Cytokines", the Journal of Immunology, vol. 161, pp. 109-414, 1998.
Chiba, "A new orally active anti-rheumatic drug targets IL-15 and IL-17", Japanese Journal of Clinical Immunology, vol. 30, No. 5, pp. 375-382, 2007.
Chinese Office Action dated Aug. 24, 2012 issued in corresponding Chinese Application No. 200980115521.9.
Chinese Office Action dated Nov. 28, 2018, regarding CN201580037108.0, 18 pages.
Choi et al. (2000). "A cost-effectiveness analysis of treatment options for patients with methotrexate-resistant rheumatoid arthritis," Arthritis Rheum., 43(10):2316-2327.
Clackson, et al., "Making antibody fragments using phage display libraries", Letters to Nature, vol. 352, pp. 624-628, 1991.
Cleland, et al., "The Development of Stable Protein Formulations: a Close Look at Protein Aggregation, Deamidation, and Oxidation", Critical Reviews in Therapeutic Drug Carrier Systems, vol. 10, No. 4, pp. 307-377, 1993.
Cook et al., (2012). "Granulocyte-macrophage colony-stimulating factor is a key mediator in experimental osteoarthritis pain and disease development," Arthritis Research & Therapy, 14(5): 1-9.
Cook et al., Blockade of collagen-induced arthritis post-onset by antibody to granulocyte macrophage colony-stimulating factor (GM-CSF): requirement for GM-CSF in the effector phase of disease. Arthritis Res. 2001 ;3:293-8.
Crane, et al., "Cytokine regulation of granulocyte-macrophage colony-stimulating factor (GM-CSF) production by human retinal pigment epithelial cells", Clinical and Experimental Immunology, vol. 115, pp. 288-293, 1999.
Danis, et al., "Effects of granulocyte-macrophage colony-stimulating factor (GM-CSF), IL-2, interferon-gamma (IFN-y), tumour necrosis factor-alpha (TNF-a) and IL-6 on the production of immunoreactive IL-1 and TNF-a by human-monocytes", Clin. Exp. Immunol., vol. 85, pp. 143-150, 1991.
De Vries et al., (1991). "Flare-up of rheumatoid arthritis during GM-CSF treatment after chemotherapy," Lancet.,338:517-8.
Dempsey et al., (1990). "Monoclonal antibodies that recognize human granulocyte-macrophage colony-stimulating factor and neutralize its bioactivity in vitro," Hybridoma, 9: 545-58.
Eberhardt et al., (2003). "Identification of two potential receptor binding sites for hGM-CSF," Braz. J. Chem. Eng. 20: 1-9.
European Examination Report dated Apr. 15, 2016, regarding EP13798260.9., 4 pages.
European Examination Report dated Feb. 13, 2017, regarding EP13798590.9., 7 pages.
European Examination Report dated Nov. 27, 2018, regarding EP15720968.5., 4 pages.
Fernandez, et al., "Transcriptional and post-transcriptional regulation of GM-CSF-induced IL-1B gene expression in PMN", Journal of Leukocyte Biology, vol. 59, pp. 598-603, 1996.
Folwaczny C et al. (2003). "Crohn's disease: an immunodeficiency?" Eur J Gastroenterol Hepatol, 15:621-6.
Gokarn, et al., "Self-Buffering Antibody Formulations", Journal of Pharmaceutical Sciences, vol. 97, No. 8, pp. 3051-3066, 2008.
Harlow, et al., A Laboratory Manual, Cold Spring Harbor Laboratory Press, New York, 1988.
Harlow, et al., Using Antibodies: a Laboratory Manual, Cold Spring Harbor Laboratory Press, New York, 1999.
Hawkins, et al., "Selection of Phage Antibodies by Binding Affinity", Journal Molecular Biology, vol. 226, pp. 889-896, 1992.
Hora, et al., "Lyophilized Formulations of Recombinant Tumor Necrosis Factor", Pharmaceutical Research, vol. 9, No. 1, pp. 33-36, 1992.
Huizinga et al. (2017). "Phase 1b randomized, double-blind study of namilumab, an anti-granulocyte macrophage colony-stimulating factor monoclonal antibody, in mild-to-moderate rheumatoid arthritis," Arthritis Research & Therapy 19(53): 1-10.
Japanese Office Action dated Feb. 27, 2019, regarding JP2016-566811., 6 pages.
Jones, "Analysis of polypeptides and proteins", Advanced Drug Delivery Reviews, vol. 10, pp. 29-90, 1993.

(56) References Cited

OTHER PUBLICATIONS

Jones, et al., "Replacing the complementarity-determining regions in a human antibody with those from a mouse", Nature, vol. 321, pp. 522-525, 1986.
Kanakura et al. (1991). "Identification of functionally distinct domains of human granulocyte-macrophage colony-stimulating factor using monoclonal antibodies," Blood, 77(5):1033-1043.
Kawaguchi, et al., (2004). "Induction of granulocyte-macrophage colony-stimulating factor by a new cytokine, ML-1 (IL-17F), via Raf I-MEK-ERK pathway", American Academy of Allergy, Asthma and Immunology,10:444-450.
Kitamura, et al., "Establishment and Characterization of a Unique Human Cell Line That Proliferates Dependently on GM-CSF, IL-3, or Erythropoietin", Journal of Cellular Physiology, vol. 140, pp. 323-334, 1989.
Klein et al., (2013). "Epitope interactions of monoclonal antibodies targeting CD20 and their relationships to functional properties," mAbs. 5(1):22-33.
Koenders, et al., "1300 IL-17 Synergy with TNF Causes Striking Cartilage Erosion In vivo", American College of Rheumatology, Annual Scientific Meeting, 2007.
Koenders, et al., Inflamm. Res., Supplement 2, p. 5100, 2008.
Kohler, et al., "Continuous cultures of fused cells secreting antibody of predefined specificity", Nature, vol. 256, pp. 495-497, 1975.
Komatsu, et al, "Establishment and Characterization of a Human Leukemic Cell Line with Megakaryocytic Features: Dependency on Granulocyte-Macrophage Colony-stimulating Factor, Interleukin 3, or Erythropoietin for Growth and Survival", Cancer Research, vol. 51, pp. 341-348, 1991.
Kunik et al., (2012). "Structural consensus among antibodies defines the antigen binding site," PLoS One, 8(2):1-12.
Laan, et al. "A role of GM-CSF in the accumulation of neutrophils in the airways caused by IL-17 and TNF-a", European Respiratory Journal, vol. 21, pp. 387-393, 2003.
Lakhtina et al., (1999). "Immunoenzyme determination of human granulocyte-macrophage colony-stimulating factor using monoclonal antibodies," Bioorg. Khim. 25: 673-8. (Abstract Only).
Lange, et al., "Growth factor requirements of childhood acute leukemia: establishment of GM-CSF-dependent cell lines", Blood, vol. 70, pp. 192-1999, 1987.
Langer, New Methods of Drug Delivery, Science, vol. 249, pp. 1527-1533, 1990.
Li et al., (2006). Human antibodies for immunotherapy development generated via a human B cell hybridoma technology. Proc. Natl. Acad. Sci. USA, 103: 3557-62.
Liu et al., "Moisture-Induced Aggregation of Lyophilized Proteins in the Solid State", Biotechnology and Bioengineering, vol. 37, pp. 177-184, 1991.
Lowman, et al., "Selecting High-Affinity Binding Proteins by Monovalent Phage Display", Biochemistry, vol. 30, pp. 10832-10838, 1991_.
Lubberts, et al., "Treatment With a Neutralizing Anti-Murine Interleukin-17 Antibody After the Onset of Collagen—Induced Arthritis Reduces Joint Inflammation, Cartilage Destruction, and Bone Erosion", Arthritis & Rheumatism, vol. 50, No. 2, pp. 650-659, 2004.
Maccallum et al., (1996). "Antibody-antigen Interactions: Contact Analysis and Binding Site Topography"; J. Mal. Biol., 262:732-745. (Abstract Only).
Manning, et al, "Stability of Protein Pharmaceuticals", Pharmaceutical Research, vol. 6, No. 11, pp. 903-918, 1989.
Marks, et al., "By-passing Immunization Human Antibodies from V-gene Libraries Displayed on Phage", Journal of Molecular Biology, vol. 22, pp. 581-597, 1991.
Marusic et al., (2002). "Local delivery of granulocyte macrophage colony-stimulating factor by retrovirally transduced antigen-specific T cells leads to severe, chronic experimental autoimmune encephalomyelitis in mice," Neurosci Lett, 332:185-9.
Matute-Bello et al., (2000). "Modulation of neutrophil apoptosis by granulocyte colony-stimulating factor and granulocyte/macrophage colony-stimulating factor during the course of acute respiratory distress syndrome," Crit Care Med., 28(1):13 pages.
Mcallister et al., (2005). "In vitro effector activity of Pneumocystis murina-specific T-cytotoxic-1 CDB' T cells: Role of granulocyte-macrophage colony-stimulating factor," Infect. Immun., 73:7450-7.
McQualter et al., (2001). "Granulocyte macrophage colony-stimulating factor: a new putative therapeutic target in multiple sclerosis," J Exp Med,194:873-81.
MorphoSys AG, (2012). "MorphoSys's MOR103 Antibody Demonstrates Excellent Safety and Efficacy in Rheumatoid Arthritis Patients", https://www.morphosys.com/media-investors/media-center/morphosyss-mor103-antibody-demonstrates-excellent-safety-and-efficacy, 6 pages.
Morrison, et al., "Chimeric human antibody molecules: Mouse antigen-binding domains with human constant region domains", Proc. Natl. Acad. Sci. USA, vol. 81, pp. 6851-6855, 1984.
Nang, "Instability, stabilization, and formulation of liquid protein pharmaceuticals", International Journal of Pharmaceutics, vol. 185, pp. 129-188, 1999.
Nang, "Lyophilization and development of solid protein pharmaceuticals", International Journal of Pharmaceutics, vol. 203, pp. 1-60, 2000.
Nice et al., (1990). "Human granulocyte-macrophage colony-stimulating factor (hGM-CSF): Identification of a binding site for a neutralizing antibody," Growth Factors 3:159-69.
Nicola et al., "Neutralizing and nonneutralizing monoclonal antibodies to the human granulocyte-macrophage colony—stimulating factor receptor alpha-chain", Blood, vol. 82, No. 6, pp. 1724-1731, 1993.
Numasaki, et al., "Interleukin-17 promotes angiogenesis and tumor growth", Blood, vol. 101, pp. 2620-2627, 2002.
Oez et al, "A Highly Sensitive Quantitative Bioassay for Human Granulocyte-Macrophage Colony-stimulating Factor", Experimental Hematology, vol. 18, pp. 1108-1111, 1990.
Oggero et al. (2004). "Defining the antigenic structure of human GM-CSF and its implications for receptor interaction and therapeutic treatments," Molecular diversity, Kluwer academic Publishers DO, 8(3):257-269.
Padlan et al., (1989). "Structure of an antibody-antigen complex: Crystal structure of the HyHEL-10 Fab-lysozyme complex"; Proc. Natl. Acad. Sci. USA, 86:5938-5942.
Park et al., (1998). "Granulocyte macrophage colony-stimulating factor is the main cytokine enhancing survival of eosinophils in asthmatic airways," Eur Respir J.,12(4):872-8.
Pearlman, et al., "Analysis of Protein Drugs", Advances in Parenteral Sciences, pp. 247-301, 1991.
Plater-Zyberk, et al., "GM-CSF neutralisation suppresses inflammation and protects cartilage in acute streptococcal mil wall arthritis of mice", Ann. Rheum. Dis, vol. 66, pp. 452-457, 2007.
Presneill et al., (2002). "A randomized phase II trial of granulocyte-macrophage colony-stimulating factor therapy in severe sepsis with respiratory dysfunction," Am J Respir Grit Care Med., 15;166(2):138-43.
Presta, "Antibody engineering", Current Opinion in Structural Biology, vol. 2, pp. 593-596, 1992.
Rambaldi, et al., "Establishment and characterization of a new granulocyte-macrophage colony-stimulating factor-dependent and interleukin-3-dependent human acute myeloid leukemia cell line (GF-D8)", Blood, vol. 81, pp. 1376-1383, 1993.
Riechmann et al., "Reshaping human antibodies for therapy", Nature, vol. 332, pp. 323-327, 1988.
Rudikoff et al., (1982). "Single amino acid substitution altering antigen-bending specificity," Proc. Natl. Acad. Sci. USA, 79:1979-83.
Sane, et al., "Raman Spectroscopic Characterization of Drying-Induced Structural Changes in a Therapeutic Antibody: correlating Structural Changes with Long-Term Stability", Journal of Pharmaceutical Sciences, vol. 93, No. 4, pp. 1005-1018, 2004.
Shen et al., (2008). "Structure-function relationships in the 1L-17 receptor: implications for signal transduction and therapy," Cytokine, 41(2):92-104.

(56) References Cited

OTHER PUBLICATIONS

Smith et al., (2006). "Synergism between GM-CSF and IFNy: Enhanced immunotherapy in mice with glioma," Int. J. Cancer, 120:75-80.
Starnes, et al., "Cutting Edge: IL-17D, a Novel Member of the IL-17 Family, Stimulates Cytokine Production and Inhibits Hemopoiesis", the Journal of Immunology, vol. 169, pp. 642-646, 2002.
Tang, et al., "Design of Freeze-Drying Processes for Pharmaceuticals: Practical Advice", Pharmaceutical Research, vol. 21, No. 2, pp. 191-200, 2004.
Taylor, et al. (2019). "Efficacy and safety of namilumab, a human monoclonal antibody against granulocyte-macrophage colony-stimulating factor (GM-CSF) ligand in patients with rheumatoid arthritis (RA) with either an inadequate response to background methotrexate therapy or an inadequate response or intolerance to an anti-TNF (tumour necrosis factor) biologic therapy: a randomized, controlled trial," Arthritis Research & Therapy, 21(101):1-13.
Valtieri, et al., "Establishment and Characterization of an Undifferentiated Human T Leukemia Cell Line which Requires Granulocyte-Macrophage Colony Stimulatory Factor for Growth", the Journal of Immunology, vol. 138, No. 11, pp. 4042-4050; 1987.
Van Dijk et al. (2001). "Human antibodies as next generation therapeutics," Curr Opin Chem Biol., 5(4):368-374. Review.
Van Nieuwenhuijze et al., (2014). "Synergism Between GM-CSF and IL-17 Causes Enhanced Joint Pathology via the Production of IL-6 and IL-23," Ann. Rheum. Dis., A24,73(Suppl 1), BMJ Publishing Group Ltd, London, UK. (Abstract Only), 2 pages.
Vasu et al. (2003). "Selective induction of dendritic cells using granulocyte macrophage-colony stimulating factor, but not fms-like tyrosine kinase receptor 3-ligand, activates thyroglobulin-specific CD4+/CD25+ T cells and suppresses experimental autoimmune thyroiditis," J Immunol., 170(11):5511-22.
Warne (2011). "Development of high concentration protein biopharmaceuticals: the use of platform approaches in formulation development," European Journal of Pharmaceutics and Biopharmaceutics, 78(2):208-212.
Wang et al. (2007). "Antibody Structure, Instability, and Formulation," Journal of Pharmaceutical Sciences, 96(1):1-26.
Yoon et al., (1998). "Synergistic anti-tumor effects with co-expression of GM-CSF and IFNy in murine tumors," Int. J. Cancer, 77:907-12.
Brazilian Office Action dated Aug. 10, 2021, regarding BR112016025126-1, 5 pages. English translation.
European Examination Report dated Sep. 3, 2021, regarding EP21161450.8, 11 pages.
Japanese Office Action dated Jan. 5, 2022, regarding JP2020-042267, 13 pages. English translation.

\* cited by examiner

ANTIBODIES NEUTRALIZING GM-CSF FOR USE IN THE TREATMENT OF RHEUMATOID ARTHRITIS OR AS ANALGESICS

CROSS REFERENCE TO RELATED APPLICATIONS

This application is a continuation application of U.S. patent application Ser. No. 14/913,578, filed Feb. 22, 2016, now U.S. Pat. No. 10,745,475, which is the national stage of International Application No. PCT/EP2014/068489, filed internationally on Sep. 1, 2014, which claims the benefit of U.S. Provisional Patent Application No. 61/871,900, filed Aug. 30, 2013, and U.S. Provisional Patent Application No. 61/871,904, filed Aug. 30, 2013, the disclosures of which are hereby incorporated by reference in their entireties for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 794112000101SEQLIST.TXT, date recorded: Aug. 17, 2020, size: 85 KB).

TECHNICAL FIELD

The present invention relates to antibodies and functional fragments thereof which neutralize the activity of human granulocyte macrophage colony stimulating factor (GM-CSF) for use as active ingredients, particularly in drugs for treating rheumatoid arthritis. The invention further relates to pharmaceutical compositions comprising such antibodies and functional fragments thereof as well as to methods of treatment of a patient in need thereof using such pharmaceutical compositions. The invention relates also to the preparation of medicaments for the treatment of rheumatoid arthritis with specific dosing. The invention relates also to antibodies and functional fragments thereof which neutralize the activity of human granulocyte macrophage colony stimulating factor for use as active ingredients in analgesics. The invention further relates to pharmaceutical compositions comprising such antibodies and functional fragments thereof as well as to methods of pain treatment of a patient in need thereof using such analgesic pharmaceutical compositions.

TECHNICAL BACKGROUND

Rheumatoid arthritis (RA) is an autoimmune disease characterized by the presence of autoantibodies, systemic inflammation and persistent synovitis affecting primarily cartilage and bone of small and midsized joints. Various inflammatory cells, including macrophages and neutrophils infiltrate the joint. These activated cells release a plethora of inflammatory cytokines and enzymes damaging local tissues. An important inflammatory mediator in RA is Granulocyte Macrophage Colony Stimulating Factor (GM-CSF) as it is involved in the activation of the innate arm of the immune system, which comprises macrophages, neutrophils, granulocytes, eosinophils and dendritic cells, all of which contribute to progression of RA. The absence of GM-CSF was found to reduce dramatically the severity of arthritis development in the antigen-induced mouse model. There is evidence that GM-CSF is produced in RA synovium and that levels of this cytokine can be measured in RA synovial fluid, suggesting that it plays a direct or indirect role in the pathogenesis of said disease. Further, studies have demonstrated the efficacy of systemic neutralization of GM-CSF using an anti-mouse GM-CSF monoclonal antibody in an acute and in a chronic mouse model of streptococcal cell wall-induced arthritis. Previous publications relating to other RA models have reported that also in collagen-induced arthritis, and arthritis induced by methylated bovine serum albumin, treatment with a neutralizing anti-GM-CSF monoclonal antibody (mAb) decreased disease severity, whereas GM-CSF injection into mice exacerbated the disease. Further, it has been shown that administration of GM-CSF to animals suffering from experimentally induced diseases (e.g. collagen-induced arthritis, etc.; cf. e.g. Bischof, R. J. et al. Clin Exp Immunol., 2000 February; 119(2): 361-367) or to patients afflicted with diseases, such as Felty's syndrome, may worsen disease symptoms (Hazenberg B P C, et al.; Blood, 1989; 83:876-82). Thus, the administration of pharmaceuticals comprising GM-CSF antagonists may be an effective way to substitute or complement commonly used treatment of autoimmune diseases such as RA.

Despite enhanced management of RA during the last decades, it has become clear that early diagnosis and aggressive step-up therapy resulting in reduction in disease activity is crucial in order to control disease progression and for bringing patients into a stage of low disease activity or remission. In some trials, the proportion of early RA patients that can achieve remission/low disease activity may be around 50% over one to two years but in daily clinical practice remission figures are lower and so far no drug has succeeded in curing RA which for most patients is a permanent chronic disease. Stable efficacy in long-term treatment is therefore a need in many patients on DMARDs and biologics, and there is accordingly also a need to improve safety over long-term administration of drugs. Further, in RA patients symptoms such as structural joint damage persist and do not completely resolve upon treatment. Accordingly, there is a need for new medicaments, which act in patients suffering from RA, for example moderate, moderate-to-severe or severe RA.

An additional problem in the treatment of RA patients is that conventional medicaments such as MTX or other chemical DMARDs or biologics such as TNF inhibitors are frequently not reducing sufficiently the symptoms of RA experienced by such individuals. Accordingly, there is a need for new medicaments which can be used alone or in addition to known medicaments, e.g., in combination with a standard MTX therapy, or other chemical DMARDs, e.g., for patients suffering from moderate, moderate-to-severe or severe rheumatoid arthritis.

Another problem associated with the use of biologics (biotechnologically produced active ingredients in a medicine), in particular biologics that are not species-specific, for example chimeric antibodies or mouse-derived antibodies used in humans is the triggering of an immune reaction against the active ingredient that is recognized as an non-self/foreign antigen. It is therefore necessary to provide medicaments that do not induce immune reactions (e.g. anti-drug antibodies, ADA) against biologics.

The above objectives are achieved by the compositions, the neutralizing antibodies or functional fragments thereof (also referred to as active ingredients) provided herein as well as by the methods of treatment of RA symptoms using the herein provided compositions and active ingredients.

Furthermore, the present invention relates to the treatment of pain. Pain can be caused by various different stimuli such as burns, cuts or by diseases, e.g. cancer, chronic diseases such as diverse inflammatory diseases or acute diseases, e.g. headache. The treatment of pain depends on the pain intensity. The WHO introduced the term "pain ladder" in its guideline for the use of drugs in the management of pain. Originally applied to the management of cancer pain, medical professionals use it as guidance in the treatment of different types of pain. According to the recommendations of the WHO patients not suffering from severe pain should first be treated with non-opioid drugs such as paracetamol, non-steroidal anti-inflammatory drugs (NSAIDs) or COX-2 inhibitors. When pain persists despite treatment with the first line medicaments mild opioids such as codeine, tramadol-hydrochloride and the like may be used. Patients suffering from severe pain or agonizing pain respond generally well to treatment with opioids, such as morphine and the like at the cost of side effects, which may become intolerable.

There is an ongoing need for the development of new analgesics, e.g., analgesics that are not associated with uncontrollable side effects or with side effects making their use completely intolerable, such as severe nausea, vomiting, gastrointestinal problems, dizziness, etc. Today, the most frequently prescribed analgesics are small organic molecules. However, modern biotechnology and the understanding of biological mechanisms underlying pain and the detection of effector molecules, surface receptors, etc. involved in the development and maintenance of pain opened up the possibility of designing molecules, e.g. peptides or nucleic acids, specifically targeting such molecules. For example, it may be possible to provide small interfering RNA (siRNA) molecules that switch off genes involved in the pain transmission, e.g. genes encoding nociceptors on cell surfaces. Another alternative would be to target proteins that are directly involved in the development or conductance of pain, e.g. nociceptors or down-stream molecules expressed on the surface or inside neuronal cells (cf. e.g. Stosser et al., J Mol Med (2011) 89:321-329).

Recently, receptors for factors that were originally discovered as important for the immune system or for hemostasis have been identified on the surface of peripheral neuronal cells. WO2010/071923 discloses the development of antibodies binding rodent GM-CSF and their use in animal models of pain. Antibodies directed to primate, e.g. human, GM-CSF were not tested.

Originally described as a potent stimulus of the growth and differentiation of granulocyte and macrophage precursor cells in vitro, granulocyte-macrophage colony-stimulating factor (GM-CSF) is an approximately 23 kDa glycoprotein with a four alpha helical bundle structure that binds to a heterodimeric receptor composed of subunits belonging to the type 1 cytokine receptor family. It stimulates the maturation of, i.a., macrophages, neutrophils, granulocytes, eosinophils and antigen-presenting dendritic cells, to increase their functional capacity in combating infections. Genetic ablation experiments i.e. experiments silencing or knocking out the gene of interest—here GM-CSF—in mice indicated that GM-CSF is essential for maintaining the functional activity of some macrophage populations such as those involved in clearing surfactant in the lung and in responding to certain kinds of infection or immune responses.

GM-CSF has potent stimulatory activities in vitro on progenitor cells for neutrophils, eosinophils, macrophages, and to a lesser extent erythroid and megakaryocyte cells. Results obtained in vivo with gene knockout mice suggest that the major physiological role of GM-CSF is to maintain or stimulate the functional activity of mature macrophages and granulocytes and to stimulate antigen presentation to the immune system. It does the latter by its direct effects on dendritic cell and macrophage production, but also by increasing, expression of the class II major histocompatibility complex and Fc receptors on macrophages and dendritic cells.

GM-CSF stimulates the functional activities of neutrophils, eosinophils, and monocyte-macrophages. These include enhancement of chemotactic activity, increased expression of cellular adhesion molecules and increased adhesion to surfaces, and increased phagocytic activity as well as inhibition and delay of apoptosis of these cells. Neutrophils represent the first line of defense against aggressions. The programmed death of neutrophils is delayed by proinflammatory stimuli including GM-CSF to ensure a proper resolution of the inflammation in time and place. GM-CSF also stimulates the capacity of these cells to mediate antibody-dependent cell cytotoxicity and to kill microorganisms intracellularly and has a 'priming' effect on these cells to enhance their response to subsequent stimuli for the oxidative burst (superoxide anion production), degranulation and release of antimicrobial agents, and chemotaxis. Further, GM-CSF stimulates the release of secondary cytokines and mediators from these cells including IL-1, G-CSF, M-CSF, and leukotrienes from neutrophils, as well as IL-1, TNF, IL-6, G-CSF, M-CSF, and prostaglandins from macrophages.

It is clear from the above that GM-CSF plays a key role in activating and maintaining the cell populations necessary to ward off infection. However, in some instances activation of these cell populations may be undesirable. For example, activation of the above cell lineages when no pathogen is present leads in many instances to acute and/or chronic inflammatory conditions which, in extreme cases, may be life-threatening. Similarly, treatment with or over-expression of GM-CSF may lead to excess immune activation and this may be accompanied by pain. The role of pain in RA is discussed, e.g., in David Walsh and Daniel McWilliams, Curr Pain Headache Rep (2012) 16:509-517. In such instances, it may be desirable to neutralize the activity of GM-CSF such that the pain is reduced or eliminated.

Further, it has been shown that administration of GM-CSF to animals suffering from experimentally induced diseases (e.g. collagen-induced arthritis, etc.; cf. e.g. Bischof, R. J. et al. Clin Exp Immunol., 2000 February; 119(2): 361-367) or to patients afflicted with diseases, such as Felty's syndrome, may worsen disease symptoms (Hazenberg B P C, et al.; Blood, 1989; 83:876-82) and cause painful sensations. GM-CSF receptors are expressed on peripheral nerve cells, for example on nociceptive neurons. Accordingly, neutralization or antagonizing the activities of GM-CSF may prevent the stimulus of GM-CSF exerted on such neuronal cells. Blocking nociception is an aim in many different pathologic conditions or diseases which are very painful. Thus, the administration of pharmaceuticals comprising GM-CSF antagonists may be an effective way to substitute or complement commonly used pain treatment.

It is therefore an aim of the invention to provide neutralizing antibodies and functional fragments thereof targeting GM-CSF, analgesic compositions comprising the same, and uses thereof comprising to reduce painful sensations in subjects, e.g., human patients, particularly in human patients suffering from rheumatoid arthritis or other autoimmune or muscoloskeletal disorders, cancer, neurodegenerative diseases, wounds, burns, etc.

It is another objective of the invention to provide neutralizing antibodies and functional fragments thereof targeting GM-CSF, analgesic compositions comprising the same that can be used in methods of treatment of human patients suffering from RA, which are insufficiently controllable with methotrexate (MTX) alone, with DMARDs, MTX plus other chemical DMARD(s) or one TNF inhibitor. These neutralizing antibodies and functional fragments thereof targeting GM-CSF or analgesic compositions comprising the same are conventionally used in the treatment of RA patients, but are sometimes insufficient to reduce the disease symptoms, e.g. pain, or lead to a remission of disease. Accordingly, there is a need for drugs that are effective in reducing disease activity, e.g. as can be determined using the DAS28CRP clinical assessment, thereby also reducing pain associated with the underlying disease, e.g. RA. It is one objective of the present invention to provide such neutralizing antibodies and functional fragments thereof targeting GM-CSF, analgesic compositions comprising the same.

Other objectives of the present invention are:
An improvement of the general physical function in a treated individual; and/or
Preventing or reducing fatigue in patients treated with the compositions of the invention; and/or
Preventing or reducing fatigue in patients treated with the analgesic compositions of the invention; and/or
Improving the quality of life of the patient; and/or
Improving work productivity; and/or
Improving safety and tolerability of the medicament; and/or
Improving immunogenicity (e.g. prevention or minimization of the formation of anti-drug antibodies (ADA), e.g. neutralizing antibodies, against the active ingredients of the inventive medicaments.

An additional problem in the treatment of RA patients is that conventional medicaments such as DMARDs, e.g. anti-folate compounds such as MTX, alone or in combination with other chemical or biologic such as TNF inhibitors are not to alleviating sufficiently pain experienced by such individuals. Accordingly, there is a need for new medicaments which can be used alone or in addition to known medicaments, e.g., in combination with a standard MTX therapy or other chemical DMARDs, or an MTX therapy and the additional administration of one or more other chemical DMARDs, e.g., for patients suffering from moderate-to-severe rheumatoid arthritis.

Another problem associated with the use of biologics, in particular biologics that are not species specific, for example chimeric antibodies or mouse-derived antibodies used in humans is their potential immunogenicity. It is therefore necessary to provide medicaments that induce very rarely immune reactions (e.g. anti-drug antibodies, ADA) against biologics.

The above objectives are achieved by the neutralizing antibodies and functional fragments thereof targeting GM-CSF, analgesic compositions comprising the same (also referred to as active ingredients) provided herein as well as by the methods of treatment of pain using the herein provided analgesics and active ingredients.

It must be noted that as used herein, the singular forms "a", "an", and "the", include plural references unless the context clearly indicates otherwise. Thus, for example, reference to "an antibody" includes one or more of such different antibodies and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having" or could even be replaced by consisting of.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

DESCRIPTION OF THE INVENTION

Aspects of the invention relate to a neutralizing antibody or a functional fragment thereof specifically binding primate GM-CSF, wherein said antibody comprises a light chain variable region comprising an amino acid sequence as set out in SEQ ID NOs: 19, 34, 54 or 55, and a heavy chain variable region comprising an amino acid sequence chosen from the group consisting of those set out in any of the SEQ ID NOs: 20-33, 35-48, 52 or 53. Any possible combination of sequences of variable region is explicitly encompassed by the scope of the present invention, e.g. combinations of SEQ ID NO: 19 and SEQ ID NO: 20, 21, 22, 23, 24, 25, 26, 27, 28, 29, 30, 31, 32, or 33, and combinations of the remaining heavy and light chain variable regions is possible.

The invention also relates to a neutralizing antibody or a functional fragment thereof specifically binding primate GM-CSF or an analgesic composition comprising such, wherein said antibody comprises a light chain variable region comprising an amino acid sequence as set out in SEQ ID NOs: 19, 34, 54 or 55, and a heavy chain variable region comprising an amino acid sequence chosen from the group consisting of those set out in any of the SEQ ID NOs: 20-33, 35-48, 52 or 53. Any possible combination of sequences of variable region is explicitly encompassed by the scope of the present invention, e.g. combinations of SEQ ID NO: 19 and SEQ ID NO: 20, 21, 22, 23, 24, 25, 26, 27, 28, 29, 30, 31, 32, or 33, and combinations of the remaining heavy and light chain variable regions is possible. The production of the neutralizing antibodies and functional fragments discussed herein is disclosed in detail in WO 2006/111353, the contents of which are disclosed herein in their entirety. With respect to the sequences, reference is made to the sequence listing in said publication. Sequence identity numbers therein correspond to sequence identity numbers in the present application.

In accordance with the invention, the neutralizing antibody or a functional fragment thereof specifically binding primate GM-CSF having in its heavy chain variable region a CDR3 comprising an amino acid sequence chosen from the group consisting of those set out in any of the SEQ ID NOs: 1-13 or 56.

Further, according to the invention, the neutralizing antibodies and functional fragments thereof targeting GM-CSF, the analgesic compositions comprising the same comprise in their heavy chain variable region a CDR3 comprising an amino acid sequence chosen from the group consisting of those set out in any of the SEQ ID NOs: 1-13 or 56.

In accordance with the invention, the neutralizing antibody or functional fragment thereof comprising a heavy chain variable region CDR3 sequence set out in any of the amino acid sequences in SEQ ID NOs: 1-13 or 56 together with the heavy chain variable region CDR1 sequence set out in the amino acid sequence of SEQ ID NO: 14 and heavy chain variable region CDR2 sequence set out in the amino acid sequence of SEQ ID NO: 15.

According to the invention, the neutralizing antibodies and functional fragments thereof targeting GM-CSF, the analgesic compositions comprising the same comprise in their heavy chain a variable region CDR3 sequence set out in any of the amino acid sequences in SEQ ID NOs: 1-13 or 56 together with the heavy chain variable region CDR1 sequence set out in the amino acid sequence of SEQ ID NO: 14 and heavy chain variable region CDR2 sequence set out in the amino acid sequence of SEQ ID NO: 15.

In accordance with the invention, the neutralizing antibody or functional fragment thereof having in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

According to the invention, the neutralizing antibodies and functional fragments thereof targeting GM-CSF, the analgesic compositions comprising the same comprise in their light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

In accordance with the invention, the neutralizing antibody or functional fragment thereof having in its light chain variable region a CDR1 comprising an amino acid sequence as set out in SEQ ID NO: 16, a CDR2 having an amino acid sequence as set out in SEQ ID NO: 17 and a CDR3 having an amino acid sequence as set out in SEQ ID NO: 18; and comprising in its heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in any of SEQ ID Nos: 1-13 or 56.

According to the invention, the neutralizing antibodies and functional fragments thereof targeting GM-CSF, the analgesic compositions comprising the same comprise in their light chain variable region a CDR1 comprising an amino acid sequence as set out in SEQ ID NO: 16, a CDR2 having an amino acid sequence as set out in SEQ ID NO: 17 and a CDR3 having an amino acid sequence as set out in SEQ ID NO: 18; and comprising in their heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in any of SEQ ID Nos: 1-13 or 56.

In a preferred embodiment, the neutralizing antibodies and functional fragments thereof targeting GM-CSF, the analgesic compositions comprising the same comprise in their light chain variable region a CDR1 comprising an amino acid sequence as set out in SEQ ID NO: 16, a CDR2 having an amino acid sequence as set out in SEQ ID NO: 17 and a CDR3 having an amino acid sequence as set out in SEQ ID NO: 18; and comprising in their heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in SEQ ID NO: 2.

In accordance with the invention, the neutralizing antibody or a functional fragment thereof specifically binding primate GM-CSF comprises a light chain amino acid sequence as set out in SEQ ID NO: 34 and a heavy chain amino acid sequence as set out in any of SEQ ID NOs: 35-48.

According to the invention, the neutralizing antibodies and functional fragments thereof targeting GM-CSF, or the analgesic compositions comprising the same comprise in their light chain amino acid sequence as set out in SEQ ID NO: 34 and a heavy chain amino acid sequence as set out in any of SEQ ID NOs: 35-48.

In a further preferred embodiment, the neutralizing antibodies and functional fragments thereof targeting GM-CSF, or the analgesic compositions comprising the same comprise in their light chain amino acid sequence as set out in SEQ ID NO: 34 and a heavy chain amino acid sequence as set out in SEQ ID NO: 35.

In accordance with the invention, the neutralizing antibody or a functional fragment thereof specifically binding primate GM-CSF comprises an amino acid sequence bearing at least 70%, at least 75%, at least 80%, at least 85%, at least 90%, at least 95%, at least 97%, or at least 99% homology to the to the respective amino acid sequence as set out in any of SEQ ID NOs: 1-48 and/or 52-56.

According to the invention, the neutralizing antibodies and functional fragments thereof targeting GM-CSF, the analgesic compositions comprising the same comprise an amino acid sequence bearing at least 70%, at least 75%, at least 80%, at least 85%, at least 90%, at least 95%, at least 97%, or at least 99% identity to the respective amino acid sequence as set out in any of SEQ ID NOs: 1-48 and/or 52-56.

In accordance with the invention, neutralizing anti-primate GM-CSF antibody or functional fragment thereof as described above for use in the treatment of RA symptoms in a subject are provided. Preferably, the subject is a mammal, more preferably a human patient. In other preferred embodiments, the neutralizing anti-primate GM-CSF antibody or functional fragment thereof for use in the treatment of RA symptoms in a subject according to the present invention is used together (e.g. at the same time or one before or after the other, according to the prescription regulations of respective drugs; e.g. before or after a meal) with at least one further active ingredient of a medicament.

According to the invention, neutralizing anti-primate GM-CSF antibody or functional fragment thereof as described above for use in the treatment of pain in a subject are provided. In preferred embodiments, the subject is a mammal, e.g., a human. In other preferred embodiments, the neutralizing anti-primate GM-CSF antibody or functional fragment thereof for use in the treatment of pain in a subject according to the present invention is used together (e.g. at the same time or one before or after the other, according to the prescription regulations of respective drugs, e.g. before or after a meal) with at least one further analgesic compound.

According to the invention, the neutralizing anti-primate GM-CSF antibody or functional fragment for use according to the present invention or any of the compositions described above, which comprise the neutralizing anti-primate GM-CSF antibody or functional fragment thereof is formulated for subcutaneous administration. This means, that the formulation has a viscosity that allows for subcutaneous injection and that the concentration of active ingredient is sufficiently high to inject a therapeutically effective dose using one injection per administered dose in order to take into account patient compliance.

According to the invention, the neutralizing anti-primate GM-CSF antibody or functional fragment for use according to the present invention or any of the analgesic compositions described above, which comprise the neutralizing anti-primate GM-CSF antibody or functional fragment thereof is formulated for subcutaneous administration. This means, that the formulation has a viscosity that allows for subcutaneous injection and that the concentration of active ingredient is sufficiently high to inject a therapeutically effective dose using one injection per administered dose in order to take into account patient compliance.

According to the invention, the neutralizing anti-primate GM-CSF antibody or functional fragment thereof for use according to the present invention is administered in combination with compounds selected from methotrexate, corticosteroids (e.g. prednisolone), opioids (e.g. codeine), hydroxychloroquine (> or equal to 200 mg/day, or >400 mg/day), oral chloroquine (>250 mg/day), or other non-biologics DMARDs.

Further, according to the invention, the neutralizing anti-primate GM-CSF antibody or functional fragment thereof for use according to the present invention is used in combination with methotrexate or other non-biologics DMARDs. Additional administration of oral corticosteroids (e.g. prednisolone or equivalents thereof) in doses up to 10 mg/day is also contemplated. According to the invention, the treatment with opioide-containing medicines is also contemplated.

Further, according to the invention, the neutralizing anti-primate GM-CSF antibody or functional fragment thereof for use according to the present invention is administered in combination with compounds selected from methotrexate, corticosteroids (e.g. prednisolone), opioids (e.g. codeine), DMARDs, hydroxychloroquine (> or equal to 200 mg/day, or >400 mg/day), oral chloroquine (>250 mg/day), or optionally other biologics, e.g. therapeutic antibodies such as infliximab or other TNF-inhibitors, CD20-antagonists, IL-17-antagonists, or IL-6R inhibitors such as tocilizumab.

In accordance with the present invention, the neutralizing anti-primate GM-CSF antibody or functional fragment thereof is used as active ingredient formulated for subcutaneous administration of doses of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, or 300 mg per dose. These doses may be administered once weekly, or in shorter or longer intervals, e.g. every second day, every third day, every fifth day, etc., or every second or third week or monthly. The doses may be administered over a period of several weeks or months according to the patients' specific needs. For example, administration over at least 3 weeks, 6 weeks, 12 weeks, 24 weeks or longer is contemplated. The doses may increase over time, e.g. starting with a lower dose at the first injection (e.g. at least 20, 25, or 50 mg in a single or more doses), and increasing the dose in the following injections, e.g. 50 to 100 mg, e.g. 75 or 80 mg at the second injection, and about 100 to 250 mg, e.g. 125 to 200 mg, e.g., about 150 mg at the third injection.

In accordance with the present invention, it is possible that the doses may decrease over time, e.g. starting with a higher dose, called loading dose, at the first injection (e.g. at least 150 or 300 mg in a single or more doses), and decreasing the dose in the following injections, e.g. 100 to 250 mg, e.g. 125 to 200 mg, e.g., about 150 mg at the second injection, 100 to 150 mg, e.g. 75 or 80 mg at the third injection.

In accordance with the present invention, it is possible to administer these doses in more than one injection, but it is preferred that one injection is administered for patient compliance. Preferably, the doses of the neutralizing anti-primate GM-CSF antibody or functional fragment thereof remain the same, e.g. about 20 mg doses, optionally administered as a first initial dose on day 1, then as a second dose about 14 days after the first initial dose, and then as further doses about every 28 day. Further, preferably, the doses are the same, e.g. about 80 mg doses, optionally administered on day 1, day 14, and then every 28 days. Further, the doses may be the same, e.g. about 150 mg doses, optionally administered on day 1, day 14, and then every 28 days. In a further embodiment, the doses are the same, e.g. about 20 mg, or about 80 mg doses or about 150 mg doses, administered after day 1, day 28, and then every 28 days, that means in 4 weeks intervals.

In further embodiments of the embodiments referred to in the preceding sections, a so-called "loading dose" is administered about 7-21 days, e.g. 10-18 days, preferably 14 days before the administration of the above described first dose. In preferred embodiments the loading dose is administered 14 days before the first dose and comprises the same, or two times the amount of the subsequent dose. For example, when the first initial dose comprises 150 mg of the herein described neutralizing antibody or a fragment thereof, the loading dose is two times 150 mg. Optionally, the loading dose may be higher, e.g., three times the amount of the first dose. The loading dose may be administered subcutaneously. The rationale behind administration of a loading dose to a patient in need thereof is that a steady state will be reached much quicker.

The second dose (ii) of the neutralizing antibody or a fragment thereof of the dosage regimen described herein may be administered 7-21 days after administration of the first initial dose, optionally 10-15 days after administration of the first initial dose. In one embodiment, the second dose is administered on day 7, 8, 9, 10, 11, 12, 13, 14, 15, 16, 17, 18, 19, 20 or 21 after administration of the first initial dose, in particular on day 14 after administration of the first initial dose.

The second dose (ii) of the neutralizing antibody or a fragment thereof of the dosage regimen described herein may also be administered 21-35 days after administration of the first initial dose, optionally 25-20 days after administration of the first initial dose. In one embodiment, the second dose is administered on day 21, 22, 23, 24, 25, 26, 27, 28, 29, 30, 31, 32, 33, 34, or 35 after administration of first initial dose, in particular on day 28 after administration of the first initial dose.

In very preferred embodiments, the neutralizing anti-primate GM-CSF antibody or functional fragment thereof for use according to the present invention is used in combination with methotrexate at conventionally prescribed doses (e.g. maximally 25 mg/weekly, e.g., 7.5 mg to 25 mg/weekly, most preferred 15 mg to 25 mg/week) or other non-biologic DMARDs.

In accordance with the invention, the neutralizing anti-primate GM-CSF antibody or functional fragment for use according to the present invention or any of the compositions comprising the neutralizing anti-primate GM-CSF antibody or functional fragment thereof is formulated for subcutaneous administration. This means, that the formulation has a viscosity that allows subcutaneous injection and further requires that the concentration of active ingredient is sufficiently high to inject a therapeutically effective dose using one injection per administered dose taking into account patient compliance.

The further doses (d) may be administered to the patient as long he is in need of a treatment and/or prevention of RA or pain, or any other arthritic or painful conditions referred to herein. Thus, the further doses (d) may be administered to the patient until a full or partial remission or alleviation of symptoms of the disease as described herein, a reduction of, e.g., the DAS28-CRP score (see below) or reduction of VAS pain (infra) is achieved. For example, further doses (d) may be administered to the patient over a period of at least 2, at least 3, at least 4, at least 5, at least 6, at least 7, at least 8, at least 9, at least 10 weeks, at least 12 weeks, at least 15 weeks, at least 18 weeks, at least 21 weeks, at least 24 weeks, at least 30 weeks, at least 36 weeks or over a period of at least 48 weeks, for at least 1 year, or longer.

If the neutralizing antibody or a fragment thereof is used for the prevention of RA or is used as analgesic, further doses (d) may be administered to the patient to the patient as long as full or partial prevention of these indications or related symptoms is desired.

It is to be understood that the administration of the neutralizing antibody or a fragment thereof may also be stopped after a certain period of treatment with the neutralizing antibody or fragment thereof after which the desired effects (such as a reduction of the DAS28-CRP score or VAS pain) have been achieved. This is due to the fact that the therapeutic or preventive effects of the antibody or fragment thereof can persist for a certain period of time after the administration has been stopped. Such a "drug holiday" (or "drug vacation", "medication vacation", "structured treatment interruption" or "strategic treatment interruption") may reduce the risk of adverse (i.e. treatment-related) effects and may maintain the sensitivity to the neutralizing antibody or fragment thereof, may lead to the recovery of some normal physiologic functions in the patient or may improve patient compliance.

The time point for a drug holiday may vary from patient to patient and may be chosen on the basis of the clinical assessment by the treating physician. This clinical assessment may take into account the presence and desired extent of therapeutic effects achieved by administration of the neutralizing antibody or fragment thereof. Any effect defined herein with respect to the term "treatment" may be indicative that a drug holiday may be made.

In one embodiment of the invention, a drug holiday is made when the patient shows a substantial reduction of the initial DAS28-CRP score. Disease severity is usually defined by the EULAR response criterion on the basis of the DAS28.

DAS28 is the Disease Activity Score in which 28 joints in the body are assessed to determine the number of tender joints and the number of swollen joints. When the DAS28 calculation includes a measurement of C-reactive protein (CRP) rather than erythrocyte sedimentation rate (ESR), it is referred to as DAS28-CRP. CRP is believed to be a more direct measure of inflammation than ESR, and is more sensitive to short term changes. CRP production is associated with radiological progression in RA and is considered at least as valid as ESR to measure RA disease activity.

DAS28-CRP>5.1 indicates severe disease activity. Moderate disease activity is characterized by a DAS28-CRP of >3.2 and 5.1. Low disease activity is characterized by a DAS28-CRP of <3.2. A DAS28-CRP of less than 2.6 indicates disease remission. Therefore, when a substantial improvement of this parameter is achieved, e.g. low disease activity or disease remission is achieved, a drug holiday may start. Alternatively, when a patient was initially diagnosed as suffering from severe disease, the drug holiday may be contemplated when such patient, after treatment according to the invention, attains a low disease level or remission.

In another embodiment, a drug holiday may be made at least 6 months, at least 7 months, at least 8 months, at least 9 months, at least 10 months, at least 11 months or at least 12 months after administration of the first (or loading) dose (a). In yet another embodiment, a drug holiday may be made at least 6 months, at least 7 months, at least 8 months, at least 9 months, at least 10 months, at least 11 months or at least 12 months after administration of the second dose (b). In a preferred embodiment a drug holiday is made after a minimum treatment of 6 months according to any of the methods disclosed herein.

During the drug holiday clinical parameters of the patient (such as the DAS28-CRP) are monitored in regular intervals, such as monthly. If the clinical parameters worsen, e.g. if the DAS28-CRP increases, the neutralizing antibody or a fragment thereof should again be administered to the patient. In one embodiment such a worsening of the clinical parameters may be an increase of the DAS28-CRP measured at the beginning of the drug holidays of about 25%, about 35%, about 45% or about 50% or more, e.g. to a DAS28-CRP of >3.2, or in the case of disease remission, to a DAS28-CRP of more than 2.6, or even more than 3.2.

After a drug holiday, the neutralizing antibody or a fragment thereof may again be used according to any the dosage regimen described herein.

According to the invention, methods of treatment of RA symptoms in a subject are provided, said methods comprising administering a composition or neutralizing antibody or functional fragment thereof according to the invention and as defined above. In accordance with the invention, the subject is a human subject, e.g. a human patient.

Further, in accordance with the present invention, methods of treatment of pain in a subject are provided, said methods comprising administering an analgesic composition or neutralizing antibody or functional fragment thereof according to the invention and as defined above. In preferred embodiments, the subject is a human subject, e.g. a human patient.

According to the invention, methods of treatment of a subject suffering from an autoimmune disease, e.g., rheumatoid arthritis are provided. In accordance with the invention, the methods of treatment in a subject are associated with mild, mild to moderate, moderate, moderate to severe or severe rheumatoid arthritis, e.g., moderate, moderate to severe or severe rheumatoid arthritis. The classification used in the context of the present invention is based on the 2010 ACR/EULAR Rheumatoid Arthritis Classification Criteria (Arthritis & Rheumatism, Vol. 62, No. 9, September 2010, pp. 2569-2581). These classification criteria, jointly published by the American College of Rheumatology (ACR) and the European League Against Rheumatism (EULAR) establish a point value between 0 and 10. Disease severity is usually defined by the value of the DAS28. DAS28-CRP>5.1 indicates severe disease activity. Moderate disease activity is characterized by a DAS28-CRP of >3.2 and 5.1. Low disease activity is characterized by a DAS28-CRP of <3.2. A DAS28-CRP of less than 2.6 indicates disease remission. When the DAS28 calculation includes a measurement of C-reactive protein (CRP) rather than erythrocyte sedimentation rate (ESR), it is referred to as DAS28-CRP. CRP is believed to be a more direct measure of inflammation than ESR, and is more sensitive to short term changes. CRP production is associated with radiological progression in RA and is considered at least as valid as ESR to measure RA disease activity. The methods of the present invention induce a disease remission or an amelioration below a DAS28-CRP value of <3.2, preferably of at least 1.2.

The clinical benefit of using the neutralizing antibody or functional fragment thereof according to the invention may be an improvement of at least 20%, at least 50% or at least 70% treatment efficacy as determined by the 1987 ACR criteria, i.e. the clinical benefit may be achieving ACR 20, ACR 50 or ACR 70, respectively. The clinical benefit comprises achieving ACR 20 in at least 40, 50, 55, 60, 65 or 70% of patients. It may comprise achieving ACR 50 in at least 20%, 25%, 30%, 35% or at least 40% of patients. It may comprise achieving ACR 70 in at least 5%, 10%, 15% or 20% of patients with insufficiently controlled RA by MTX or other non-biologic DMARDs treatment.

According to the present invention, the neutralizing antibody or a functional fragment thereof specifically binding primate GM-CSF for use in the treatment of an inflammatory disease, e.g., RA, in a patient to provide clinical benefit as measured by a decrease in DAS28-CRP by more than 1.2 within 85 days, the method comprising administering a composition comprising the neutralizing antibody to GM-CSF or a functional fragment thereof to the patient, wherein the composition is administered, e.g., at a dose of 20 mg or 50 mg or 80 mg or 150 mg/month after two initial injections of the same dose on day one and/or about 14 days later by subcutaneous administration.

In accordance with the present invention, the neutralizing antibody or a functional fragment thereof specifically binding primate GM-CSF for use in the treatment of an inflammatory disease, e.g., RA to provide clinical benefit as measured by an improvement of at least ACR20, at least ACR50 or at least ACR70 within about 7 weeks, the method comprising administering a composition comprising the neutralizing antibody or functional fragment thereof to the patient, wherein the composition is administered at a dose of 20 mg or of 50 mg or of 80 mg or of 150 mg/month after two initial injections of the same dose on day one and about 14 days later, e.g., by subcutaneous administration. Preferably, the therapeutic effect is detectable within preferably 2, 3 or 4 weeks after treatment begin.

In accordance with the present invention, the neutralizing antibody or a functional fragment thereof specifically binding primate GM-CSF for use in the treatment of an inflammatory disease, e.g., RA for inducing remission of RA in a patient, as measured by a DAS28-CRP of less than 2.6, the method comprising administering a composition comprising a therapeutically effective amount of the neutralizing antibody or functional fragment thereof to the patient, wherein the composition is administered by subcutaneous administration, and wherein the onset of remission is seen after about 2 weeks, at least after 3 weeks, at least after 4 weeks, at least after 5 weeks, at least after 6 weeks, at least after 8 weeks, at least after 10 weeks, or at least 12 weeks after the initial administration of the neutralizing antibody or functional fragments thereof disclosed herein.

In accordance with the present invention, the neutralizing antibody or a functional fragment thereof specifically binding primate GM-CSF for use in the treatment of an inflammatory disease, e.g., RA, resulting in an improvement of physical function of an RA patient, as determined by HAQ-DI, is used in a method comprising administering a composition comprising the neutralizing antibody or a functional fragment thereof specifically binding GM-CSF to the patient, wherein the composition is administered in a dose of 10-150 mg, e.g., at a dose of 10-30 mg, e.g., 20 mg, or at a dose of 50-150 mg, e.g., at a dose of 80 mg, or at a dose of 100-300 mg, e.g., at a dose of 150 mg, in 1 ml monthly by subcutaneous administration, and wherein an improvement in HAQ-DI is achieved within about 2 weeks, at least after 3 weeks, at least after 4 weeks, at least after 5 weeks, at least after 6 weeks, at least after 8 weeks, at least after 10 weeks, or at least 12 weeks, e.g., wherein the improvement is a reduction of at least 0.25 in the patient's HAQ-DI score.

In accordance with the methods of the present invention, the treatment alleviates fatigue and/or sleeping disturbances associated with pain (as determined using the Facit-Fatigue, the MOS sleep scale or any other suitable scale).

In accordance with the invention, the methods of the present invention, the treatment alleviates fatigue and/or sleeping disturbances (as determined using the Facit-Fatigue, the MOS sleep scale or other classification systems for the assessment of sleeping disturbances).

In accordance with methods of the present invention, the administration of a composition or neutralizing antibody or functional fragment thereof rarely or only minimally induces formation of anti-drug antibodies, neutralizing anti-drug antibodies, or increases of native anti-GM-CSF autoantibodies compared with the start of the treatment, and at least does not to induce such antibodies to an extent where the treatment has to be interrupted.

In accordance with the methods of the present invention, the treatment of an inflammatory disease comprises the subcutaneous administration of the above-described compositions or neutralizing antibody or functional fragment thereof. The compositions, or the neutralizing antibody or functional fragment s thereof of the present invention may be administered subcutaneously in the inventive methods of treatment of an inflammatory disease, e.g. at doses of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, of 300 mg, or higher. It is contemplated that the compositions, or the neutralizing antibody or functional fragment s thereof of the present invention is administered subcutaneously at doses of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, of 300 mg, in at least 3, e.g., at least 5, e.g., at least 7 doses over a period of at least 21 weeks. It is, however, possible to administer fewer or more of doses according to the specific requirements and the patient's characteristics (e.g. depending on severity of disease, gender, age, weight, other drugs used, etc.). The duration of the treatment may be at least 21 weeks, but it is contemplated that the therapeutic methods of the invention are set forth as long as necessary. It is also contemplated that MTX is administered at the same time according to standard therapeutic regimen (e.g. 7.5 mg to 25 mg MTX per week as suggested in the Guidelines of the British Society for Rheumatology of July 2000), e.g., at a dose of 7.5 to 25 mg/week, 15 to 25 mg/week or 7.5 to 15 mg/week.

It is also possible to administer the herein disclosed compositions, or of the neutralizing antibody or functional fragment s thereof for any of the above time periods, but with intervals, e g administer the compositions or active ingredients for 2, 3, or 4 weeks or 1, 2, or 3 months and use an interval of 2, 3, or 4 weeks or 1, 2, or 3 months, where no composition is administered. At the same time, administration of MTX at the above indicated weekly doses should be continued, optionally accompanied by supplementary administration of folic acid/folinic acid on the days where MTX is not administered.

In accordance with the methods of the present invention, administration of any of the herein disclosed compositions, or of the neutralizing antibody or functional fragment s thereof in a pharmaceutically acceptable carrier, e.g., in a pharmaceutically acceptable carrier that allows for subcutaneous administration is contemplated. In accordance with the methods of the present invention, administration of the composition or neutralizing antibody or functional fragment thereof results in an about ≥20%, about ≥25%, about ≥30% ≥40%, or about ≥50% reduction of pain as measured on the 100 mm VAS scale after 12 weeks.

In accordance with the methods of the present invention, administration of the composition or neutralizing antibody or functional fragment thereof results in an in vivo half-life of the active ingredient of about 2 to 4 weeks, e.g. about 2 to 3 weeks after administration to the patient.

Furthermore, it is also possible to use other biologics in combination with the compositions of the present invention, for example monoclonal antibodies targeting CD20, for example rituximab, or antibodies targeting other cytokines or cytokine receptors, for example tocilizumab, which targets the IL-6 receptor, or antibodies targeting the GM-CSF-receptor.

The compositions or medicaments according to the invention comprising the above antibodies or functional fragments or uses thereof are embodiments of the invention.

Compositions or medicaments according to the invention or kits comprising the above antibodies or functional fragments or uses thereof are embodiments of the invention.

The compositions or medicaments comprising the above antibodies or functional fragments or uses thereof are embodiments of the invention.

It is contemplated that the present methods and compositions may be employed for the treatment of pain from chronic conditions (including inhibiting progression of and/ or reversing damage associated with chronic conditions). Chronic conditions include, for example, arthritic conditions such as osteoarthritis, rheumatoid arthritis, and psoriatic arthritis. For example, the present methods and compositions may be used to treat one or more symptoms or signs of osteoarthritis of the joint, (such as a hip or knee) or the back (for example, the lower back). Chronic conditions also include, for example, conditions associated with or resulting from pain such as chronic pain, including pain associated with or arising from cancer, from infection or from the nervous system (e.g., neurogenic pain such as peripheral neurogenic pain following pressure upon or stretching of a peripheral nerve or root or having its origin in stroke, multiple sclerosis or trauma, including of the spinal cord). Chronic conditions also include, for example, conditions associated with or arising from psychogenic pain (e.g., pain not due to past disease or injury or visible sign of damage inside or outside the nervous system). The present methods and compositions may also be employed for the treatment of back pain from other arthritic conditions, including gout and spondylarthropathies (including ankylosing spondylitis, Reiter's syndrome, psoriatic arthropathy, enterapathric spondylitis, juvenile arthropathy or juvenile ankylosing spondylitis, and reactive arthropathy). The present methods and compositions may be used for the treatment of back pain from infectious or post-infectious arthritis (including gonoccocal arthritis, tuberculous arthritis, viral arthritis, fungal arthritis, syphlitic arthritis, and Lyme disease).

The invention provides methods of treatment of pain in a subject, wherein the pain is associated with an autoimmune disease, e.g., rheumatoid arthritis. In accordance with the invention, the methods of treatment of pain in a subject are associated with mild, mild to moderate, moderate, moderate to severe or severe rheumatoid arthritis, e.g., moderate, moderate to severe or severe rheumatoid arthritis. The classification used in the context of the present invention is based on the 2010 ACR/EULAR Rheumatoid Arthritis Classification Criteria (Arthritis & Rheumatism, Vol. 62, No. 9, September 2010, pp. 2569-2581). These classification criteria, jointly published by the American College of Rheumatology (ACR) and the European League Against Rheumatism (EULAR) establish a point value between 0 and 10. Disease severity is usually defined by the EULAR response criterion on the basis of the DAS28. DAS28-CRP>5.1 indicates severe disease activity. Moderate disease activity is characterized by a DAS28-CRP of >3.2 and 5.1. Low disease activity is characterized by a DAS28-CRP of ≤3.2. A DAS of less than 2.6 indicates disease remission. DAS28-CRP between 2.6 and 3.2 indicates low disease activity. DAS28 is the Disease Activity Score in which 28 joints in the body are assessed to determine the number of tender joints and the number of swollen joints. When the DAS28 calculation includes a measurement of C-reactive protein (CRP) rather than erythrocyte sedimentation rate (ESR), it is referred to as DAS28-CRP. CRP is believed to be a more direct measure of inflammation than ESR, and is more sensitive to short term changes. CRP production is associated with radiological progression in RA and is considered at least as valid as ESR to measure RA disease activity. The methods of the present invention induce a disease remission or an amelioration below a DAS28-CRP value of <3.2.

Aspects of the Invention

1. A neutralizing antibody or a functional fragment thereof specifically binding primate GM-CSF for use in the treatment of pain emanating from an inflammatory disease selected from a group comprising rheumatoid arthritis, systemic lupus erythematosus (SLE), psoriatic arthritis, ankylosing spondylitis, juvenile idiopathic arthritis, and osteoarthritis, wherein the neutralizing antibody or a functional fragment specifically binding primate GM-CSF is used according to the following dosing scheme:
(i) a first initial dose,
(ii) followed by administration of a second dose within a period of 7-21 days after said first initial dose,
(iii) at least one further dose administered within a period of 21-35 days after said second dose,
(iv) optionally followed by further doses administered within intervals of 21-35 days.

2. The neutralizing antibody or a functional fragment thereof specifically binding primate GM-CSF for use in the treatment of pain emanating from an inflammatory disease according to item 1, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days.

3. The neutralizing antibody or a functional fragment thereof specifically binding primate GM-CSF for use in the treatment of pain emanating from an inflammatory disease according to items 1 or 2, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days, and
wherein the patients receive at least one additional anti-inflammatory drug selected from the group comprising DMARDs, corticosteroids, e.g. glucocorticoids, NSAIDS, opioids, and biologic drugs.

4. The neutralizing antibody or a functional fragment thereof specifically binding primate GM-CSF for use in the treatment of pain emanating from an inflammatory disease according to items 1 to 3, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days, and
wherein the at least one additional anti-inflammatory drug is selected from anti-folate compounds.

5. The neutralizing antibody or a functional fragment thereof specifically binding primate GM-CSF for use in the treatment of pain emanating from an inflammatory disease according to items 1 to 4, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days, and
wherein the anti-folate compound is methotrexate.

6. The neutralizing antibody or a functional fragment thereof specifically binding primate GM-CSF for use in the treatment of pain emanating from an inflammatory disease according to items 1 to 5, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days, and
wherein the methotrexate is administered once weekly.

7. The neutralizing antibody or a functional fragment thereof specifically binding primate GM-CSF for use in the treatment of pain emanating from an inflammatory disease according to items 1 to 6, wherein said disease is selected from a group comprising rheumatoid arthritis, SLE, psoriatic arthritis, ankylosing spondylitis, juvenile idiopathic arthritis and osteoarthritis,
wherein the neutralizing antibody or a functional fragment specifically binding primate GM-CSF is used according to the following dosing scheme:
(i) a first initial dose,
(ii) followed by administration of a second dose after about 14 days after the first initial dose,
(iii) at least one further dose administered after about 28 days after said second dose,
(iv) optionally followed by further doses administered within intervals of about 28 days, and
wherein the at least one additional anti-inflammatory drug is methotrexate that is administered at weekly doses, e.g. once a week, at a dose per administration of 7.5 to 25 mg, e.g., 15-25 mg, or 7.5 to 15 mg.

8. The neutralizing antibody or a functional fragment thereof specifically binding primate GM-CSF for use in the treatment of pain emanating from an inflammatory disease according to items 1 to 7, wherein said disease is selected from a group comprising rheumatoid arthritis, SLE, psoriatic arthritis, ankylosing spondylitis, juvenile idiopathic arthritis and osteoarthritis, wherein the neutralizing antibody or a functional fragment specifically binding primate GM-CSF is used according to the following dosing scheme:
  (i) a first initial dose,
  (ii) followed by administration of a second dose after about 14 days after the first initial dose,
  (iii) at least one further dose administered after about 28 days after said second dose,
  (iv) optionally followed by further doses administered within intervals of about 28 days, and
wherein the antibody is formulated for subcutaneous administration.

9. A neutralizing antibody or a functional fragment thereof specifically binding primate GM-CSF for use in the treatment of pain emanating from an inflammatory disease selected from a group comprising rheumatoid arthritis, ankylosing spondylitis, juvenile idiopathic arthritis SLE, psoriatic arthritis, and osteoarthritis,
wherein said disease is wherein the neutralizing antibody or a functional fragment thereof specifically binding primate GM-CSF is used according to the following dosing scheme:
  (i) a first initial dose,
  (ii) followed by administration of a second dose within a period of 7-21 days after the first initial dose,
  (iii) at least one further dose administered within a period of 21-35 days after said second dose,
  (iv) optionally followed by further doses administered within intervals of 21-35 days,
wherein the patients are selected from the following patient subgroups:
  a-1) Patients previously not treated for an inflammatory disease selected from a group comprising rheumatoid arthritis, SLE, psoriatic arthritis, ankylosing spondylitis, juvenile idiopathic arthritis or osteoarthritis, or
  a-2) Patients previously not treated for pain associated with a group of inflammatory diseases comprising rheumatoid arthritis, SLE, psoriatic arthritis, ankylosing spondylitis, juvenile idiopathic arthritis, or osteoarthritis, or
  a-3) Patients treated for an inflammatory condition.

9a) A neutralizing antibody or a functional fragment thereof specifically binding primate GM-CSF for use in the treatment of pain emanating from an inflammatory disease selected from a group comprising rheumatoid arthritis, SLE, psoriatic arthritis, ankylosing spondylitis, juvenile idiopathic arthritis and osteoarthritis,
wherein said disease is wherein the neutralizing antibody or a functional fragment thereof specifically binding primate GM-CSF is used according to the following dosing scheme:
  (i) a first initial dose,
  (ii) followed by administration of a second dose after about 14 days after the first initial dose,
  (iii) at least one further dose administered after 28 days after said second dose,
  (iv) optionally followed by further doses administered within intervals of about 28 days, and,
wherein the patients are selected from the following patient subgroups:
  a-1) Patients previously not treated for an inflammatory disease selected from a group comprising rheumatoid arthritis, SLE, psoriatic arthritis, ankylosing spondylitis, juvenile idiopathic arthritis, and osteoarthritis, or
  a-2) Patients previously not treated for pain associated with a group of inflammatory diseases comprising rheumatoid arthritis, SLE, psoriatic arthritis, ankylosing spondylitis, juvenile idiopathic arthritis, and osteoarthritis, or
  a-3) Patients treated for an inflammatory condition.

9b) A neutralizing antibody or a functional fragment thereof specifically binding primate GM-CSF for use in the treatment of pain emanating from an inflammatory disease selected from a group comprising rheumatoid arthritis, psoriatic arthritis, ankylosing spondylitis, juvenile idiopathic arthritis, and osteoarthritis,
wherein said disease is wherein the neutralizing antibody or a functional fragment thereof specifically binding primate GM-CSF is used according to the following dosing scheme:
  (i) a first initial dose,
  (ii) followed by administration of a second dose after about 14 days after the first initial dose,
  (iii) at least one further dose administered after 28 days after said second dose,
  (iv) optionally followed by further doses administered within intervals of about 28 days, and,
wherein the patients are selected from the following patient subgroups:
  a-1) Patients previously not treated for an inflammatory disease selected from a group comprising rheumatoid arthritis, SLE, psoriatic arthritis, ankylosing spondylitis, juvenile idiopathic arthritis and osteoarthritis, or
  a-2) Patients previously not treated for pain associated with a group of inflammatory diseases comprising rheumatoid arthritis, SLE, psoriatic arthritis, ankylosing spondylitis, juvenile idiopathic arthritis, or osteoarthritis, or
  a-3) Patients treated for an inflammatory condition.

9c) A neutralizing antibody or a functional fragment thereof specifically binding primate GM-CSF for use in the treatment of pain emanating from rheumatoid arthritis,
wherein said disease is wherein the neutralizing antibody or a functional fragment thereof specifically binding primate GM-CSF is used according to the following dosing scheme:
  (i) a first initial dose,
  (ii) followed by administration of a second dose after about 14 days after the first initial dose,
  (iii) at least one further dose administered after 28 days after said second dose,
  (iv) optionally followed by further doses administered within intervals of about 28 days, and,
wherein the patients are selected from the following patient subgroups:
  a-1) Patients previously not treated for rheumatoid arthritis, or
  a-2) Patients previously not treated for pain associated with rheumatoid arthritis, or
  a-3) Patients treated for rheumatoid arthritis.

9d) The neutralizing antibody or a functional fragment thereof specifically binding primate GM-CSF for use in the treatment of pain emanating from rheumatoid arthritis, wherein the neutralizing antibody or a functional fragment thereof specifically binding primate GM-CSF is used according to the following dosing scheme:
(i) a first initial dose,
(ii) followed by administration of a second dose after about 14 days after the first initial dose,
(iii) at least one further dose administered after 28 days after said second dose,
(iv) optionally followed by further doses administered within intervals of about 28 days, and,
wherein the patients are selected from the following patient subgroups:
a-1) Patients previously not treated for rheumatoid arthritis, or
a-2) Patients previously not treated for inflammatory pain associated with rheumatoid arthritis, or
a-3) Patients treated for rheumatoid arthritis,
wherein the patients receive at least one additional anti-inflammatory drug selected from the group comprising DMARDs, corticosteroids, NSAIDS, opioids, and biologic drugs.

9e) The neutralizing antibody or a functional fragment thereof specifically binding primate GM-CSF for use in the treatment of pain emanating from an inflammatory disease according to item 9d), wherein the at least one additional anti-inflammatory drug is methotrexate, which administered at a dose of, e.g. 7.5 to 25 mg/weekly, such as at a dose of 7.5 to 15 mg/weekly or 15 to 25 mg/weekly.

9f) The neutralizing antibody or a functional fragment thereof specifically binding primate GM-CSF for use in the treatment of pain emanating from an inflammatory disease according to item 9e), wherein the at least one additional anti-inflammatory drug is methotrexate, which is administered at a dose of 7.5 to 25 mg/weekly, such as at a dose of 7.5 to 15 mg/weekly or 15 to 25 mg/weekly, and wherein the neutralizing antibody or a functional fragment thereof specifically binding primate GM-CSF is formulated for subcutaneous administration.

9g) The neutralizing antibody or a functional fragment thereof specifically binding primate GM-CSF for use in the treatment of pain emanating from an inflammatory disease
(i) according to items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 10 to 50 mg.

9h) The neutralizing antibody or a functional fragment thereof specifically binding primate GM-CSF for use in the treatment of an inflammatory disease
(i) according to items 9a) to 9c), wherein the neutralizing antibody or a functional fragment thereof specifically binding primate GM-CSF is formulated for subcutaneous administration,
(ii) or according to any one of items 9d) to 9g), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 20 mg.

9i) The neutralizing antibody or a functional fragment thereof specifically binding primate GM-CSF for use in the treatment of an inflammatory disease
(i) according to items 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 25 to 100 mg.

9j) The neutralizing antibody or a functional fragment thereof specifically binding primate GM-CSF for use in the treatment of an inflammatory disease
(i) according to items 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 80 mg.

9k) The neutralizing antibody or a functional fragment thereof specifically binding primate GM-CSF for use in the treatment of an inflammatory disease
(i) according to items 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration, and wherein in any of (i) or (ii) the first initial dose of said neutralizing antibody or functional fragment thereof, as well as the second dose and optionally further doses comprises a quantity of 50 to 300 mg.

9l) The neutralizing antibody or a functional fragment thereof specifically binding primate GM-CSF for use in the treatment of an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
  and wherein in any of (i) or (ii) the first initial dose of said neutralizing antibody or functional fragment thereof, as well as the second dose and optionally further doses comprises a quantity of 150 mg.

9m) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is formulated for subcutaneous administration,
  and wherein in any of (i) or (ii) the first initial dose of said neutralizing antibody or functional fragment thereof, as well as the second dose and optionally further doses comprises a quantity of 20 mg, or of 80 mg, or of 150 mg,
  and wherein in any of (i) or (ii) the pain is moderate, moderate to severe or severe pain.

9n) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly,
  and wherein the neutralizing antibody or a functional fragment thereof specifically binding primate GM-CSF is formulated for subcutaneous administration,
  and wherein in any of (i) or (ii) the first initial dose of said neutralizing antibody or functional fragment thereof as well as the second dose and optionally further doses comprises a quantity of 20 mg, or of 80 mg, or of 150 mg,
  and wherein in any of (i) or (ii) the pain is moderate, moderate to severe or severe pain,
  and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35.

9o) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, wherein the neutralizing antibody or a functional fragment thereof specifically binding primate GM-CSF is formulated for subcutaneous administration,
  and wherein in any of (i) or (ii) the first initial dose of said neutralizing antibody or functional fragment thereof as well as the second dose and optionally further doses comprises a quantity of 20 mg, or of 80 mg, or of 150 mg,
  and wherein in any of (i) or (ii) the pain is moderate, moderate to severe or severe pain,
  and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with at least one other chemical DMARD(s) and/or at least one TNF-inhibitor.

9p) The neutralizing antibody or a functional fragment thereof specifically binding primate GM-CSF for use in the treatment of pain emanating from an inflammatory disease
  (i) according to item items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, wherein the neutralizing antibody or a functional fragment thereof specifically binding primate GM-CSF is administered subcutaneously, and wherein in any of (i) or (ii) the first initial dose of said neutralizing antibody or functional fragment thereof as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor.

9q) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, wherein the neutralizing antibody or a functional fragment thereof specifically binding primate GM-CSF is administered subcutaneously, and wherein in any of (i) or (ii) the first initial dose of said neutralizing antibody or functional fragment thereof as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor.

9r) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof as well as the second dose and optionally further doses comprises a quantity of 20 mg, or of 80 mg, or of 150 mg, and wherein in any of (i) or (ii) the pain is moderate, moderate to severe or severe pain, and wherein the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor, and wherein in any of (i) or (ii) the administration of the neutralizing antibody or functional fragment alone or in a combination therapy with methotrexate or another anti-folate compound thereof induces ACR20/50/70 scores of ≥50%/20%/10% at 24 weeks in TNF non-responders, or ≥55%/30%/10% in methotrexate non-responders.

9s) The neutralizing antibody or a functional fragment thereof specifically binding primate GM-CSF for use in the treatment of pain emanating from an inflammatory disease
  (i) according to items 9a) to 9c), wherein the neutralizing antibody or a functional fragment thereof specifically binding primate GM-CSF is formulated for subcutaneous administration, or
  (ii) according to any one of items 9d) to 9f), wherein the at least one additional anti-inflammatory drug is methotrexate, which is administered at a dose of 7.5 to 25 mg/weekly, e.g., at a dose of 7.5 to 15 mg/weekly or 15 to 25 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor, and wherein in any of (i) or (ii) the disease activity (DAS28CRP) at least 12 weeks subsequent to the start of treatment, e.g., at least 24 weeks subsequent to the start of treatment is reduced to a score of <3.2, e.g., <2.6.

10. The neutralizing antibody or a functional fragment thereof specifically binding primate GM-CSF for use in the treatment of pain emanating from an inflammatory disease according to item 9 including any of items 9a) to 9s),
  wherein the neutralizing antibody or a functional fragment thereof specifically binding primate GM-CSF is used according to the following dosing scheme:
    (i) a first initial dose,
    (ii) followed by administration of a second dose after about 14 days,
    (iii) at least one further dose administered after 28 days after said second dose,
    (iv) optionally followed by further doses administered within intervals of about 28 days, and
  wherein the patients are selected from the following subgroups:
a-1) Patients not treated for an inflammatory condition or for pain, further selected from
  individuals with RA that have not previously been treated for RA, or
  individuals that have not previously been treated for RA who were diagnosed as RA patients at least 6 months prior to the first initial dose, at least 1 year prior to the first initial dose, 2 years prior to the first initial dose, 3 years prior to the first initial dose, 4 years prior to the first initial dose, or more than 5 years prior to the first initial dose, or
a-2) Patients treated for RA who have not received medication for pain in addition to the treatment for RA,
a-3) Patients treated for an inflammatory condition, selected from the group comprising rheumatoid arthritis, SLE, psoriatic arthritis, ankylosing spondylitis, juvenile idiopathic arthritis, and osteoarthritis selected from the following subgroups:
  patients receiving a non-biologic DMARD treatment, but who have previously not been treated with biologics (biologics treatment naïve),
  patients receiving a treatment with anti-folate compounds, e.g., methotrexate, or other DMARS and/or glucocorticoids,
  patients receiving a treatment with anti-folate compounds, e.g., a stable dose of methotrexate at about >15 mg/week for at least 12 weeks and who do not suffer from neutropenia,
  patients that are treated with methotrexate for at least 3 months, wherein said patients further receiving folinic acid or folic acid on the days after methotrexate administration, but not on the day when methotrexate is administered,
  patients that are treated with methotrexate but not co-treated with adenosine receptor antagonists selected from a group comprising theophylline and caffeine,
  patients that are treated with methotrexate without any signs of marrow suppression, said signs comprising neutropenia, for at least 12 weeks after initial administration of weekly doses of 7.5-25 mg per week, e.g., after initial administration of weekly doses of 7.5-15 mg per week,
  Patients that are treated with methotrexate, which having a genetic polymorphism in at least one thymidylate synthase gene, the AICAR transformylase gene, or the RFC1 gene;

patients without polymorphism at C677T in the MTHFR (methylene tetrahydrofolate reductase gene), patients with insufficiently controlled RA treated with methotrexate for at least 3 months with moderate, moderate to severe, or severe disease activity, patients with insufficiently controlled RA treated with DMARDs, e.g. those selected from sulfasalazine, leflunomide or hydroxychloroquine, for at least 3 months with moderate, moderate to severe, or severe disease activity, patients with moderate, moderate to severe, or severe disease activity insufficiently controlled RA treated with methotrexate for at least 3 months in combination with another non-biologic (chemical) DMARD, e.g., an anti-folate compound, e.g., methotrexate, patients with moderate, moderate to severe, or severe disease activity insufficiently controlled RA treated with methotrexate for at least 3 months in combination with another biologic DMARD, e.g., antagonists of IL-6R, IL-6, or IL-17;

patients selected from the group of individuals receiving non-biologic DMARD treatment, e.g., treatment with an anti-folate compound, e.g., treatment with methotrexate, plus biologic treatment, wherein the biologic treatment is selected from the group of compounds comprising anti-cytokine antagonists selected from a group chemical antagonists and antibodies or derivatives thereof, cytokine receptor antagonists selected from a group comprising chemical antagonists and antibodies or derivatives thereof, TNF-alpha neutralising agents selected from a group comprising chemical neutralising agents and antibodies or derivatives thereof, IL-1 neutralising agents selected from a group comprising chemical neutralising agents and antibodies or derivatives thereof, IL-6 neutralising agents selected from a group comprising chemical neutralising agents and antibodies or derivatives thereof, IL-6R neutralising agents selected from a group comprising chemical neutralising agents and antibodies or derivatives thereof, CD20 neutralising agents selected from a group comprising chemical neutralising agents and antibodies or derivatives thereof, IL-17 antagonists selected from a group comprising chemical neutralising agents and antibodies or derivatives thereof, and patients with insufficiently controlled RA treated with methotrexate for at least 3 months in combination with a biologic DMARD with moderate, moderate to severe, or severe disease activity, a-4) Patients treated for pain comprising individuals selected from the follow subgroups of patients:

patients treated for pain associated with a disease other than rheumatoid arthritis, wherein said disease is selected from autoimmune diseases, neuropathies, or inflammatory diseases, patients treated with methotrexate for at least 3 months in combination with a biologic DMARD with moderate/moderate to severe/severe disease activity, wherein the pain is insufficiently controlled by the treatment patients with a non-biologic DMARD treatment and reduction of RA signs and symptoms and inhibition of progression of structural damage, wherein the pain persists or remits, patients with no signs of ongoing inflammation, where pain in the joints is still present, patients insufficiently controlled on methotrexate, patients who were insufficiently controlled on methotrexate plus TNF inhibitor treatment;

patients who were insufficiently controlled on treatment with sulfasalazine, hydroxychloroquine, and/or leflunomide, patients that do not suffer from neutropenia (or optionally those that do not suffer from a cancer); or patients that have not been treated with GM-CSF prior to the first initial dose;

patients that have previously not been treated to correct chemotherapy induced cytopenias and to counteract cytopenia-related predisposition to infections and hemorrhages, patients that do not suffer from respiratory tract problems, particularly lung problems associated with infections.

11. A neutralizing antibody or a functional fragment thereof specifically binding primate GM-CSF for use in the treatment of pain emanating from an inflammatory disease as defined in any one of items 1 to 10, wherein the administration of the second dose is omitted, thereby having the doses after the first initial dose administered in intervals of 21-35 days, specifically 28 days.

12. The neutralizing antibody or functional fragment thereof specifically binding primate GM-CSF for use in the treatment of pain emanating from an inflammatory disease as defined in any one of items 1 to 11, wherein the pain is mild, mild to moderate, e.g., moderate, moderate to severe or severe pain.

13. The neutralizing antibody or a functional fragment thereof specifically binding primate GM-CSF for use in the treatment of pain emanating from an inflammatory disease as defined in any one of items 1 to 12, wherein the antibody is formulated for subcutaneous administration.

14. The neutralizing antibody or a functional fragment thereof specifically binding primate GM-CSF for use in the treatment of pain emanating from an inflammatory disease as defined in any one of items 1 to 13, the first initial dose of said neutralizing antibody or functional fragment thereof, as well as the second dose and optionally further doses comprises a quantity of 10 to 50 mg, or a quantity of 25 to 100 mg, or a quantity of 50 to 300 mg.

15. The neutralizing antibody or a functional fragment thereof specifically binding primate GM-CSF for use in the treatment of pain emanating from an inflammatory disease as defined in any one of items 1 to 14, wherein the first initial dose of said neutralizing antibody or functional fragment thereof, as well as the second dose and optionally further doses comprises a quantity of 20 mg, or of 80 mg, or of 150 mg.

16. The neutralizing antibody or a functional fragment thereof specifically binding primate GM-CSF for use in the treatment of pain emanating from an inflammatory disease as defined in any one of items 1 to 15, wherein said antibody comprises a light chain variable region comprising an amino acid sequence as set out in SEQ ID NOs: 19, 34, 54 or 55, and a heavy chain variable region comprising an amino acid sequence chosen from the group consisting of those set out in any of the SEQ ID NOs: 20-33, 35-48, 52 or 53, e.g., said antibody comprises a light chain variable region comprising an amino acid sequence as set out in SEQ ID NO: 19, and a heavy chain variable region comprising an amino acid sequence set out in SEQ ID NO: 21.

17. The neutralizing antibody or a functional fragment thereof specifically binding primate GM-CSF for use in the treatment of pain emanating from an inflammatory disease as defined in any one of items 1 to 16, wherein said neutralizing antibody or functional fragment thereof comprises in its heavy chain variable region a CDR3 comprising an amino acid sequence chosen from the group consisting of those set out in any of the SEQ ID NOs: 1-13 or 56.

18. The neutralizing antibody or a functional fragment thereof specifically binding primate GM-CSF for use in the treatment of pain emanating from an inflammatory disease as defined in any one of items 1 to 17, wherein said neutralizing antibody or functional fragment thereof comprises a heavy chain variable region CDR3 sequence set out in any of the amino acid sequences in SEQ ID NOs: 1-13 or 56 together with the heavy chain variable region CDR1 sequence set out in the amino acid sequence of SEQ ID NO: 14 and heavy chain variable region CDR2 sequence set out in the amino acid sequence of SEQ ID NO: 15.

19. The neutralizing antibody or a functional fragment thereof specifically binding primate GM-CSF for use in the treatment of pain emanating from an inflammatory disease as defined in any one of items 1 to 18, wherein said neutralizing antibody or functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

20. The neutralizing antibody or a functional fragment thereof specifically binding primate GM-CSF for use in the treatment of pain emanating from an inflammatory disease as defined in any one of items 1 to 19, wherein said neutralizing antibody or functional fragment thereof comprises in its light chain variable region a CDR1 comprising an amino acid sequence as set out in SEQ ID NO: 16, a CDR2 having an amino acid sequence as set out in SEQ ID NO: 17 and a CDR3 having an amino acid sequence as set out in SEQ ID NO: 18; and comprising in its heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in any of SEQ ID Nos: 1-13 or 56, e.g., SEQ ID No. 2.

21. The neutralizing antibody or a functional fragment thereof specifically binding primate GM-CSF for use in the treatment of pain emanating from an inflammatory disease as defined in any one of items 1 to 20, comprising a light chain amino acid sequence as set out in SEQ ID NO: 34 and a heavy chain amino acid sequence as set out in any of SEQ ID NOs: 35-48, e.g., SEQ ID NO: 35.

22. The neutralizing antibody or a functional fragment thereof specifically binding primate GM-CSF for use in the treatment of pain emanating from an inflammatory disease as defined in any one of items 1 to 21, wherein said neutralizing antibody or functional fragment thereof comprises an amino acid sequence bearing at least 70%, at least 80%, at least 85%, at least 90%, at least 95% homology to the respective amino acid sequence as set out in any of SEQ ID NOs: 1-48 and/or 52-56.

23. The neutralizing antibody or a functional fragment thereof specifically binding primate GM-CSF for use in the treatment of pain emanating from an inflammatory disease as defined in any one of items 1 to 22, wherein additionally at least one further analgesic compound is used.

24. The neutralizing anti-primate GM-CSF antibody or functional fragment thereof for use according to any one of items 1 to 23, wherein the at least one further analgesic compound is selected from the group comprising oral corticosteroids, e.g., prednisolone or codeine.

25. A method of treatment of pain in a patient comprising administering the neutralizing antibody or a functional fragment thereof specifically binding primate GM-CSF as defined in any one of items 1 to 24.

26. The method according to any one of item 25, wherein the pain is associated with mild, mild to moderate, moderate, moderate to severe or severe rheumatoid arthritis, e.g., moderate, moderate to severe or severe rheumatoid arthritis.

27. The method according to any one of items 25 or 26, wherein the subject has moderate, moderate to severe, or severe rheumatoid arthritis that is insufficiently controlled by either methotrexate alone, or by methotrexate in combination with at least one other chemical DMARD(s) and/or at least one TNF-inhibitor and/or at least one inhibitor of a cytokine different from TNF, e.g. an IL-6R inhibitor.

28. The method according to any one of items 25 to 27, wherein neutralizing antibody or functional fragment thereof is administered parenterally, e.g., subcutaneously.

29. The method according to any one of items 25 to 28, wherein the neutralizing antibody or functional fragment thereof as defined in any of the preceding claims is administered subcutaneously in at least 3, at least 5, at least 7 doses over a period of at least 21 weeks.

30. The method according to any one of items 25 to 29, wherein the administration of the neutralizing antibody or functional fragment alone or in a combination therapy with methotrexate or another anti-folate compound thereof induces ACR20/50/70 scores of ≥50%/20%/10% at 24 weeks in TNF non-responders, or ≥55%/30%/10% in methotrexate non-responders.

31. The method according to any one of items 25 to 30, wherein the treatment alleviates fatigue and/or sleeping disturbances associated with pain.

32. The method according to any one of items 25 to 31, wherein the patient's pain symptoms remit for at least 1 year subsequent to the start of treatment.

33. The method according to any one of items 25 to 32, wherein structural joint damages does not advance for at least 1 year subsequent to the start of treatment.

34. The method according to any one of items 25 to 33, wherein the disease activity (DAS28CRP) at least 12 weeks subsequent to the start of treatment, at least 24 weeks subsequent to the start of treatment is reduced to a score of <3.2, e.g., <2.6.

35. The method according to any one of items 25 to 34, wherein the serum levels contains at least 20%, at least 25%, at least 30%, at least 40%, at least 50% of the neutralizing anti-primate GM-CSF antibody or functional fragment thereof seven days, for at least 14 days, e.g., for at least 21 days, for at least 28 days after the last administration.

Preferred aspects relating to antibodies neutralizing GM-CSF relate to:

1. A neutralizing antibody or a functional fragment thereof specifically binding primate GM-CSF for use in the treatment of an inflammatory disease selected from a group comprising rheumatoid arthritis, SLE, psoriatic arthritis, ankylosing spondylitis, juvenile idiopathic arthritis, and osteoarthritis,
   wherein the neutralizing antibody or a functional fragment specifically binding primate GM-CSF is used according to the following dosing scheme:
   (i) a first initial dose,
   (ii) followed by administration of a second dose within a period of 7-21 days after the first initial dose,
   (iii) at least one further dose administered within a period of 21-35 days after said second dose,
   (iv) optionally followed by further doses administered within intervals of 21-35 days.

2. The neutralizing antibody or a functional fragment thereof specifically binding primate GM-CSF for use in the treatment of an inflammatory disease according to item 1, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose,
   (iv) optionally followed by further doses administered within intervals of about 28 days.

3. The neutralizing antibody or a functional fragment thereof specifically binding primate GM-CSF for use in the treatment of an inflammatory disease according to item 1 or 2, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose,
   (iv) optionally followed by further doses administered within intervals of about 28 days, and
   wherein the patients receive at least one additional anti-inflammatory drug selected from the group comprising DMARDs, corticosteroids, e.g., glucocorticoids, NSAIDS, opioids, and biologic drugs.

4. The neutralizing antibody or a functional fragment thereof specifically binding primate GM-CSF for use in the treatment of an inflammatory disease according to items 1 to 3, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose,
   (iv) optionally followed by further doses administered within intervals of about 28 days, and
   wherein the at least one additional anti-inflammatory drug is selected from anti-folate compounds.

5. The neutralizing antibody or a functional fragment thereof specifically binding primate GM-CSF for use in the treatment of an inflammatory disease according to items 1 to 4, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment thereof specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose,
   (iv) optionally followed by further doses administered within intervals of about 28 days, and
   wherein the anti-folate compound is methotrexate.

6. The neutralizing antibody or a functional fragment thereof specifically binding primate GM-CSF for use in the treatment of an inflammatory disease according to items 1 to 5, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment thereof specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose,
   (iv) optionally followed by further doses administered within intervals of about 28 days, and
   wherein the methotrexate is administered once weekly.

7. The neutralizing antibody or a functional fragment thereof specifically binding primate GM-CSF for use in the treatment of an inflammatory disease according to items 1 to 6, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment thereof specifically binding primate GM-CSF is used according to the following dosing scheme:
   (i) a first initial dose,
   (ii) followed by administration of a second dose after about 14 days after the first initial dose,
   (iii) at least one further dose administered after about 28 days after said second dose, (iv) optionally followed by further doses administered within intervals of about 28 days, and
wherein the at least one additional anti-inflammatory drug is methotrexate that is administered once a week at a dose per administration of 7.5 to 25 mg, e.g., 15-25 mg, or 7.5 to 15 mg.

8. The neutralizing antibody or a functional fragment thereof specifically binding primate GM-CSF for use in the treatment of an inflammatory disease according to items 1 to 7, wherein said disease is selected from a group comprising rheumatoid arthritis, SLE, psoriatic arthritis, ankylosing spondylitis, juvenile idiopathic arthritis, and osteoarthritis,
   wherein the neutralizing antibody or a functional fragment thereof specifically binding primate GM-CSF is used according to the following dosing scheme:
      (ii) followed by administration of a second dose after about 14 days after the first initial dose,
      (iii) at least one further dose administered after about 28 days after said second dose,
      (iv) optionally followed by further doses administered within intervals of about 28 days, and
   wherein the antibody is formulated for subcutaneous administration.

9. A neutralizing antibody or a functional fragment thereof specifically binding primate GM-CSF for use in the treatment of an inflammatory disease selected from a group comprising rheumatoid arthritis, SLE, psoriatic arthritis, ankylosing spondylitis, juvenile idiopathic arthritis, and osteoarthritis,
   wherein said disease is wherein the neutralizing antibody or a functional fragment thereof specifically binding primate GM-CSF is used according to the following dosing scheme:
      (i) a first initial dose,
      (ii) followed by administration of a second dose within a period of 7-21 days after the first initial dose,
      (iii) at least one further dose administered within a period of 21-35 days after said second dose,
      (iv) optionally followed by further doses administered within intervals of 21-35 days,
   wherein the patients are selected from the following patient subgroups:
      a-1) Patients not treated for an inflammatory disease selected from a group comprising rheumatoid arthritis, SLE, psoriatic arthritis, ankylosing spondylitis, juvenile idiopathic arthritis, and osteoarthritis, or
      a-2) Patients treated for an inflammatory condition.

9a) A neutralizing antibody or a functional fragment thereof specifically binding primate GM-CSF for use in the treatment of an inflammatory disease selected from a group comprising rheumatoid arthritis, SLE, psoriatic arthritis, ankylosing spondylitis, juvenile idiopathic arthritis and osteoarthritis,
   wherein said disease is wherein the neutralizing antibody or a functional fragment thereof specifically binding primate GM-CSF is used according to the following dosing scheme:
      (v) a first initial dose,
      (vi) followed by administration of a second dose after about 14 days after the first initial dose,
      (vii) at least one further dose administered after 28 days after said second dose,
      (viii) optionally followed by further doses administered within intervals of about 28 days, and,
   wherein the patients are selected from the following patient subgroups:
      a-1) Patients previously not treated for an inflammatory disease selected from a group comprising rheumatoid arthritis, SLE, psoriatic arthritis, ankylosing spondylitis, juvenile idiopathic arthritis, or osteoarthritis, or
      a-2) Patients treated for an inflammatory condition.

9b) A neutralizing antibody or a functional fragment thereof specifically binding primate GM-CSF for use in the treatment of an inflammatory disease selected from a group comprising rheumatoid arthritis, psoriatic arthritis, ankylosing spondylitis, juvenile idiopathic arthritis, or osteoarthritis,
   wherein said disease is wherein the neutralizing antibody or a functional fragment thereof specifically binding primate GM-CSF is used according to the following dosing scheme:
      (v) a first initial dose,
      (vi) followed by administration of a second dose after about 14 days after the first initial dose,
      (vii) at least one further dose administered after 28 days after said second dose,
      (viii) optionally followed by further doses administered within intervals of about 28 days, and,
   wherein the patients are selected from the following patient subgroups:
      a-1) Patients previously not treated for an inflammatory disease selected from a group comprising rheumatoid arthritis, SLE, psoriatic arthritis, ankylosing spondylitis, juvenile idiopathic arthritis and osteoarthritis, or
      a-2) Patients previously not treated for inflammatory pain associated with a group of inflammatory diseases comprising rheumatoid arthritis, SLE, psoriatic arthritis, ankylosing spondylitis, juvenile idiopathic arthritis, and osteoarthritis, or
      a-3) Patients treated for an inflammatory condition.

9c) A neutralizing antibody or a functional fragment thereof specifically binding primate GM-CSF for use in the treatment of rheumatoid arthritis,
   wherein said disease is wherein the neutralizing antibody or a functional fragment thereof specifically binding primate GM-CSF is used according to the following dosing scheme:
      (v) a first initial dose,
      (vi) followed by administration of a second dose after about 14 days after the first initial dose,
      (vii) at least one further dose administered after 28 days after said second dose,
      (viii) optionally followed by further doses administered within intervals of about 28 days, and,
   wherein the patients are selected from the following patient subgroups:
      a-1) Patients previously not treated for rheumatoid arthritis, or
      a-2) Patients previously not treated for inflammatory pain associated with rheumatoid arthritis, or
      a-3) Patients treated for rheumatoid arthritis.

9d) The neutralizing antibody or a functional fragment thereof specifically binding primate GM-CSF for use in the treatment of rheumatoid arthritis,
   wherein the neutralizing antibody or a functional fragment specifically binding primate GM-CSF is used according to the following dosing scheme:

(v) a first initial dose,
(vi) followed by administration of a second dose after about 14 days,
(vii) at least one further dose administered after 28 days after said second dose,
(viii) optionally followed by further doses administered within intervals of about 28 days, and,
wherein the patients are selected from the following patient subgroups:
 a-1) Patients previously not treated for rheumatoid arthritis, or
 a-2) Patients previously not treated for inflammatory pain associated with rheumatoid arthritis, or
 a-3) Patients treated for rheumatoid arthritis,
wherein the patients receive at least one additional anti-inflammatory drug selected from the group comprising DMARDs, corticosteroids, NSAIDS, opioids, and biologic drugs.

9e) The neutralizing antibody or a functional fragment thereof specifically binding primate GM-CSF for use in the treatment of an inflammatory disease according to item 9d), wherein the at least one additional anti-inflammatory drug is methotrexate, which administered at a dose of, e.g. 15-25 mg., or 7.5 to 25 mg/weekly, such as at a dose of 7.5 to 15 mg/weekly.

9f) The neutralizing antibody or a functional fragment thereof specifically binding primate GM-CSF for use in the treatment of an inflammatory disease according to item 9e), wherein the at least one additional anti-inflammatory drug is methotrexate, which is administered at a dose of 15-25 mg, or 7.5 to 25 mg/weekly, such as at a dose of 7.5 to 15 mg/weekly, and wherein the neutralizing antibody or a functional fragment thereof specifically binding primate GM-CSF is formulated for subcutaneous administration.

9g) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, wherein the first initial dose of said neutralizing antibody or functional fragment thereof, as well as the second dose and optionally further doses comprises a quantity of 10 to 50 mg, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration, and wherein the first initial dose of said neutralizing antibody or functional fragment thereof, as well as the second dose and optionally further doses comprises a quantity of 10 to 50 mg.

9h) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 15-25 mg, or 7.5 to 25 mg/weekly, e.g., at a dose of 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 20 mg.

9i) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 25 to 100 mg.

9j) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 80 mg.

9k) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 50 to 300 mg.

9l) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 150 mg.

9m) The neutralizing antibody or a functional fragment thereof specifically binding primate GM-CSF for use in the treatment of an inflammatory disease
(i) according to any one of items 9a) to 9c), wherein the neutralizing antibody or a functional fragment thereof specifically binding primate GM-CSF is formulated for subcutaneous administration, or
(ii) according to any one of items 9d)-9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 20 mg, or of 80 mg, or of 150 mg,
and wherein in any of (i) or (ii) the pain is moderate, moderate to severe or severe pain.

9n) The neutralizing antibody or a functional fragment thereof specifically binding primate GM-CSF for use in the treatment of an inflammatory disease
(i) according to 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof, as well as the second dose and optionally further doses comprises a quantity of 20 mg, or of 80 mg, or of 150 mg,
and wherein in any of (i) or (ii) the pain is moderate, moderate to severe or severe pain,
and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35.

9o) The neutralizing antibody or a functional fragment thereof specifically binding primate GM-CSF for use in the treatment of an inflammatory disease
(i) according to 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is formulated for subcutaneous administration,
and wherein in any of (i) or (ii) the first initial dose of said neutralizing antibody or functional fragment thereof as well as the second dose and optionally further doses comprises a quantity of 20 mg, or of 80 mg, or of 150 mg,
and wherein in any of (i) or (ii) the pain is moderate, moderate to severe or severe pain,
and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35,
and wherein in any of (i) or (ii) the subject has moderate, moderate to severe, or severe rheumatoid arthritis that is insufficiently controlled by either methotrexate alone, or by methotrexate in combination with at least one other chemical DMARD(s) and/or at least one TNF-inhibitor.

9p) The neutralizing antibody or a functional fragment thereof specifically binding primate GM-CSF for use in the treatment of an inflammatory disease
(i) according to any one of items 9 and 9a) to 9c), wherein the neutralizing antibody or a functional fragment thereof specifically binding primate GM-CSF is formulated for subcutaneous administration, or
(ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof, as well as the second dose and optionally further doses comprises a quantity of 20 mg, or 80 mg, or 150 mg, and wherein in any of (i) or (ii) the pain is moderate, moderate to severe or severe pain, and wherein the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor.

9q) The neutralizing antibody or a functional fragment thereof specifically binding primate GM-CSF for use in the treatment of an inflammatory disease (i) according to item any one of items 9 and 9a) to 9c), wherein the neutralizing antibody or a functional fragment thereof specifically binding primate GM-CSF is formulated for subcutaneous administration, or (ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof, as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor.

9r) The neutralizing antibody or a functional fragment thereof specifically binding primate GM-CSF for use in the treatment of an inflammatory disease (i) according to item any one of items 9 and 9a) to 9c), wherein the neutralizing antibody or a functional fragment thereof specifically binding primate GM-CSF is formulated for subcutaneous administration, or (ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof, as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor, and wherein in any of (i) or (ii) the administration of the neutralizing antibody or functional fragment alone or in a combination therapy with methotrexate or another anti-folate compound thereof induces ACR20/50/70 scores of ≥50%/20%/10% at 24 weeks in TNF non-responders, or ≥55%/30%/10% in methotrexate non-responders.

9s) The neutralizing antibody or a functional fragment thereof specifically binding primate GM-CSF for use in the treatment of an inflammatory disease (i) according to item any one of items 9 and 9a) to 9c), wherein the neutralizing antibody or a functional fragment thereof specifically binding primate GM-CSF is formulated for subcutaneous administration, or (ii) according to any one of items 9d) to 9f), wherein the at least one additional anti-inflammatory drug is methotrexate, which is administered at a dose of 7.5 to 25 mg/weekly, e.g., at a dose of 15-25 mg, or 7.5 to 15 mg/weekly, and wherein the neutralizing antibody or a functional fragment thereof specifically binding primate GM-CSF is administered subcutaneously, and wherein in any of (i) or (ii) the first initial dose of said neutralizing antibody or functional fragment thereof, as well as the second dose and optionally further doses comprises a quantity of 20 mg, or of 80 mg, or of 150 mg, and wherein in any of (i) or (ii) the pain is moderate, moderate to severe or severe pain, and wherein in any of (i) or (ii) the neutralizing antibody or a functional fragment thereof specifically binding primate GM-CSF comprising a light chain variable region set forth in SEQ ID No: 19 and a heavy chain variable region set forth in SEQ ID NO: 21, or sequences that are at least 70%, at least 75%, at least 80%, at least 85%, at least 90%, at least 95%, at least 97%, or at least 99%, identical with SEQ ID NO: 19 and/or with SEQ ID NO: 21, e.g., a light chain amino acid sequence as set out in SEQ ID NO: 34 and a heavy chain amino acid sequence as set out in any of SEQ ID NOs: 35-48, e.g., SEQ ID NO: 35, or sequences that are at least 70%, at least 75%, at least 80%, at least 85%, at least 90%, at least 95%, at least 97%, or at least 99%, identical with SEQ ID NO: 34 and/or with SEQ ID NOs: 35-48, e.g., with SEQ ID NO:35, and wherein in any of (i) or (ii) the subject has moderate, moderate to severe, or severe rheumatoid arthritis that is insufficiently controlled by either methotrexate alone, or by methotrexate in combination with one TNF-inhibitor, and wherein in any of (i) or (ii) the disease activity (DAS28CRP) at least 12 weeks subsequent to the start of treatment, e.g., at least 24 weeks subsequent to the start of treatment is reduced to a score of <3.2, e.g., <2.6.

10. The neutralizing antibody or a functional fragment thereof specifically binding primate GM-CSF for use in the treatment of an inflammatory disease according to item 9 including any of items 9a) to 9s),
    wherein the neutralizing antibody or a functional fragment thereof specifically binding primate GM-CSF is used according to the following dosing scheme:
    (i) a first initial dose,
    (ii) followed by administration of a second dose after about 14 days after the first initial dose,
    (iii) at least one further dose administered after 28 days after said second dose,
    (iv) optionally followed by further doses administered within intervals of about 28 days, and
    wherein the patients are selected from the following subgroups:
    a-1) Patients not treated for an inflammatory condition or for inflammatory pain, further selected from
        individuals with RA that have not previously been treated for RA, or
        individuals that have not previously been treated for RA who were diagnosed as RA patients at least 6 months prior to the first initial dose, at least 1 year prior to the first initial dose, 2 years prior to the first initial dose, 3 years prior to the first initial dose, 4 years prior to the first initial dose, or more than 5 years prior to the first initial dose, or
    a-2) Patients treated for RA who have not received medication for pain in addition to the treatment for RA,
    a-3) Patients treated for an inflammatory condition, selected from the group comprising rheumatoid arthritis, SLE, psoriatic arthritis, ankylosing spondylitis, juvenile idiopathic arthritis, and osteoarthritis selected from the following subgroups:
        patients receiving a non-biologic DMARD treatment, but who have previously not been treated with biologics (biologics treatment naïve),
        patients receiving a treatment with anti-folate compounds, e.g., methotrexate, or other DMARS and/or glucocorticoids,
        patients receiving a treatment with anti-folate compounds, e.g., a stable dose of methotrexate at about >15 mg/week for at least 12 weeks and who do not suffer from neutropenia,
        patients that are treated with methotrexate for at least 3 months, wherein said patients further receiving folinic acid or folic acid on the days after methotrexate administration, but not on the day when methotrexate is administered,
        patients that are treated with methotrexate but not co-treated with adenosine receptor antagonists selected from a group comprising theophylline and caffeine,
        patients that are treated with methotrexate without any signs of marrow suppression, said signs comprising neutropenia, for at least 12 weeks after initial administration of weekly doses of 7.5-25 mg per week, e.g., after initial administration of weekly doses of 15-25 mg, or 7.5-15 mg per week,
        Patients that are treated with methotrexate, which having a genetic polymorphism in at least one thymidylate synthase gene, the AICAR transformylase gene, or the RFC1 gene;
        patients without polymorphism at C677T in the MTHFR (methylene tetrahydrofolate reductase gene),
        patients with insufficiently controlled RA treated with methotrexate for at least 3 months with moderate, moderate to severe, or severe disease activity
        patients with moderate, moderate to severe, or severe disease activity insufficiently controlled RA treated with methotrexate for at least 3 months in combination with another non-biologic DMARD, e.g., an anti-folate compound, e.g., methotrexate,
        patients with insufficiently controlled RA treated with DMARDs, e.g. selected from sulfasalazine, leflunomide or hydroxychloroquine, for at least 3 months with moderate, moderate to severe, or severe disease activity
        patients selected from the group of individuals receiving non-biologic DMARD treatment, e.g., treatment with an anti-folate compound, e.g., treatment with methotrexate, plus biologic treatment, wherein the biologic treatment is selected from the group of compounds comprising comprising
        anti-cytokine antagonists selected from a group chemical antagonists and antibodies or derivatives thereof,
        cytokine receptor antagonists selected from a group comprising chemical antagonists and antibodies or derivatives thereof,
        TNF-alpha neutralising agents selected from a group comprising chemical neutralising agents and antibodies or derivatives thereof, IL-1 neutralising agents selected from a group comprising chemical neutralising agents and antibodies or derivatives thereof, IL-6 neutralising agents selected from a group comprising chemical neutralising agents and antibodies or derivatives thereof, and CD20 neutralising agents selected from a group comprising chemical neutralising agents and antibodies or derivatives thereof, patients with insufficiently controlled RA treated with methotrexate for at least 3 months in combination with a biologic DMARD with moderate, moderate to severe, or severe disease activity, a-4) Patients treated for inflammatory pain comprising individuals selected from the follow subgroups of patients:

patients treated for pain associated with a disease other than rheumatoid arthritis, wherein said disease is selected from autoimmune diseases, neuropathies, or inflammatory diseases, patients treated with methotrexate for at least 3 months in combination with a biologic DMARD with moderate/moderate to severe/severe disease activity, wherein the inflammatory pain is insufficiently controlled by the treatment patients with a non-biologic DMARD treatment and reduction of RA signs and symptoms and inhibition of progression of structural damage, wherein the pain persists or remits, patients with no signs of ongoing inflammation, where pain in the joints is still present, patients insufficiently controlled on methotrexate, patients who were insufficiently controlled on methotrexate plus TNF alpha inhibitor treatment;

patients who were insufficiently controlled on treatment with sulfasalazine, hydroxychloroquine, and/or leflunomide or other DMARDS, patients that do not suffer from neutropenia or a cancer; or patients that have not been treated with GM-CSF prior to the first initial dose (t=d0);

patients that have previously not been treated to correct chemotherapy induced cytopenias and to counteract cytopenia-related predisposition to infections and hemorrhages, patients that do not suffer from respiratory tract problems, particularly lung problems associated with infections.

11. A neutralizing antibody or a functional fragment thereof specifically binding primate GM-CSF for use in the treatment of an inflammatory disease as defined in any one of items 1 to 10, wherein the administration of the second dose is omitted, thereby having the doses after the first initial dose administered in intervals of 21-35 days, optionally about 28 days.

12. The neutralizing antibody or a functional fragment thereof specifically binding primate GM-CSF for use in the treatment of an inflammatory disease as defined in any one of items 1 to 11, wherein the antibody is formulated for subcutaneous administration.

13. The neutralizing antibody or a functional fragment thereof specifically binding primate GM-CSF for use in the treatment of an inflammatory disease as defined in any one of items 1 to 12, wherein the first initial dose of said neutralizing antibody or functional fragment thereof, as well as the second dose and optionally further doses comprises a quantity of 10 to 50 mg, or a quantity of 25 to 100 mg, or a quantity of 50 to 300 mg.

14. The neutralizing antibody or a functional fragment thereof specifically binding primate GM-CSF for use in the treatment of an inflammatory disease as defined in any one of items 1 to 13, wherein the first initial dose of said neutralizing antibody or functional fragment thereof, as well as the second dose and optionally further doses comprises a quantity of 20 mg, or of 80 mg, or of 150 mg.

15. The neutralizing antibody or a functional fragment thereof specifically binding primate GM-CSF for use in the treatment of an inflammatory disease as defined in any one of items 1 to 14, wherein said antibody comprises a light chain variable region comprising an amino acid sequence as set out in SEQ ID NOs: 19, 34, 54 or 55, and a heavy chain variable region comprising an amino acid sequence chosen from the group consisting of those set out in any of the SEQ ID NOs: 20-33, 35-48, 52 or 53, e.g., said antibody comprises a light chain variable region comprising an amino acid sequence as set out in SEQ ID NO: 19, and a heavy chain variable region comprising an amino acid sequence set out in any of the SEQ ID NOs: 21.

16. The neutralizing antibody or a functional fragment thereof specifically binding primate GM-CSF for use in the treatment of an inflammatory disease as defined in any one of items 1 to 15, wherein said neutralizing antibody or functional fragment thereof comprises in its heavy chain variable region a CDR3 comprising an amino acid sequence chosen from the group consisting of those set out in any of the SEQ ID NOs: 1-13 or 56.

17. The neutralizing antibody or a functional fragment thereof specifically binding primate GM-CSF for use in the treatment of an inflammatory disease as defined in any one of items 1 to 16, wherein said neutralizing antibody or functional fragment thereof comprises a heavy chain variable region CDR3 sequence set out in any of the amino acid sequences in SEQ ID NOs: 1-13 or 56 together with the heavy chain variable region CDR1 sequence set out in the amino acid sequence of SEQ ID NO: 14 and heavy chain variable region CDR2 sequence set out in the amino acid sequence of SEQ ID NO: 15.

18. The neutralizing antibody or a functional fragment thereof specifically binding primate GM-CSF for use in the treatment of an inflammatory disease as defined in any one of items 1 to 17, wherein said neutralizing antibody or functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

19. The neutralizing antibody or a functional fragment thereof specifically binding primate GM-CSF for use in the treatment of an inflammatory disease as defined in any one of items 1 to 18, wherein said neutralizing antibody or functional fragment thereof comprises in its light chain variable region a CDR1 comprising an amino acid sequence as set out in SEQ ID NO: 16, a CDR2 having an amino acid sequence as set out in SEQ ID NO: 17 and a CDR3 having an amino acid sequence as set out in SEQ ID NO: 18; and comprising in its heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in any of SEQ ID Nos: 1-13 or 56, e.g., SEQ ID No. 2.

20. The neutralizing antibody or a functional fragment thereof specifically binding primate GM-CSF for use in the treatment of an inflammatory disease as defined in any one of items 1 to 19, comprising a light chain amino acid sequence as set out in SEQ ID NO: 34 and a heavy chain amino acid sequence as set out in any of SEQ ID NOs: 35-48, e.g., SEQ ID NO: 35.

21. The neutralizing antibody or a functional fragment thereof specifically binding primate GM-CSF for use in the treatment of an inflammatory disease as defined in any one of items 1 to 20, wherein said neutralizing antibody or functional fragment thereof comprises an amino acid sequence bearing at least 70% homology to the respective amino acid sequence as set out in any of SEQ ID NOs: 1-48 and/or 52-56.

22. The neutralizing antibody or a functional fragment thereof specifically binding primate GM-CSF for use in the treatment of an inflammatory disease as defined in any one of items 1 to 21, wherein additionally at least one further analgesic compound is used.

23. The neutralizing anti-primate GM-CSF antibody or functional fragment thereof for use according to any one of items 1 to 22, wherein the at least one further analgesic compound is selected from the group comprising oral corticosteroids, e.g., prednisolone or codeine.

24. A method of treatment of an inflammatory disease selected from a group comprising rheumatoid arthritis, SLE, psoriatic arthritis, ankylosing spondylitis, juvenile idiopathic arthritis, or osteoarthritis in a patient comprising administering the neutralizing antibody or a functional fragment thereof specifically binding primate GM-CSF as defined in any one of items 1 to 23.

25. The method according to any one of item 24, wherein the patient suffers from mild, mild to moderate, moderate, moderate to severe or severe rheumatoid arthritis, e.g., moderate, moderate to severe or severe rheumatoid arthritis.

26. The method according to any one of items 24 or 25, wherein the subject has moderate, moderate to severe, or severe rheumatoid arthritis that is insufficiently controlled by either methotrexate alone, or by methotrexate in combination with at least one other chemical DMARD(s) and/or at least one TNF-inhibitor and/or at least one inhibitor of a cytokine different from TNF, e.g. an IL-6R inhibitor.

27. The method according to any one of items 24 to 26, wherein neutralizing antibody or functional fragment thereof is administered parenterally, e.g., subcutaneously.

28. The method according to any one of items 24 to 27, wherein the neutralizing antibody or functional fragment thereof as defined in any of the preceding claims is administered subcutaneously in at least 3, at least 5, at least 7 doses over a period of at least 21 weeks.

29. The method according to any one of items 24 to 28, wherein the administration of the neutralizing antibody or functional fragment alone or in a combination therapy with methotrexate or another anti-folate compound thereof induces ACR20/50/70 scores of ≥50%/20%/10% at 24 weeks in TNF non-responders, or ≥55%/30%/10% in methotrexate non-responders.

30. The method according to any one of items 24 to 29, wherein the treatment alleviates fatigue and/or sleeping disturbances associated with pain.

31. The method according to any one of items 24 to 30, wherein the patient's pain symptoms remit for at least 1 year subsequent to the start of treatment.

32. The method according to any one of items 24 to 31, wherein structural joint damages does not advance for at least 1 year subsequent to the start of treatment.

33. The method according to any one of items 24 to 32, wherein the disease activity (DAS28CRP) at least 12 weeks subsequent to the start of treatment, at least 24 weeks subsequent to the start of treatment is reduced to a score of <3.2, e.g., <2.6.

34. The method according to any one of items 24 to 33, wherein the serum levels contains at least 20%, at least 25%, at least 30%, at least 40%, at least 50% of the neutralizing anti-primate GM-CSF antibody or functional fragment thereof seven days, for at least 14 days, e.g., for at least 21 days, for at least 28 days after the last administration.

In any of the above embodiments it is contemplated to administer the first dose optionally as a so-called "loading dose" of the neutralizing anti-GM-CSF antibody, and preferably in an amount of two times the amount administered with the first dose according to the present dosing regime. For example, when the first dose according to the herein disclosed dosing regimen (usually) comprises administration of 150 mg of the neutralizing antibody or functional fragment thereof, the loading dose is administered in an amount of, preferably two times 150 mg.

Description of the Invention

The American College of Rheumatology (ACR) proposed a set of criteria for classifying RA. The commonly used criteria are the ACR 1987 revised criteria. Diagnosis of RA according to the ACR criteria requires a patient to satisfy a minimum number of listed criteria, such as tender or swollen joint counts, stiffness, pain, radiographic indications and measurement of serum rheumatoid factor. ACR 20, ACR 50 and ACR 70 are commonly used measures to express efficacy of RA therapy, particularly in clinical trials. ACR 20 represents a 20% improvement in the measured ACR criteria. Analogously, ACR 50 represents a 50% improvement in the measured ACR criteria, and ACR 70 represents a 70% improvement in the measured ACR criteria. In preferred embodiments of the present invention, the neutralizing antibody or functional fragments thereof achieve an ACR of at least 20, e.g., at least 30, e.g., at least 40, 50, 60, or 70.

An individual, patient reported measure of disability in RA patients is the Health Assessment Questionnaire Disability Index (HAQ-DI). HAQ-DI scores represent physical function in terms of the patient's reported ability to perform everyday tasks, including the level of difficulty they experience in carrying out the activity. By recording patients' ability to perform everyday activities, the HAQ-DI score can be used as one measure of their quality of life.

Clinical benefit achieved as described herein may comprise any one or more of the following outcomes.

The clinical benefit may be a decrease in DAS28-CRP by more than 1.2. The reduction in DAS28-CRP may be achieved in at least 40%, at least 50% or at least 60% of patients treated. The clinical benefit may comprise an increasing the proportion of patients who achieve a decrease in DAS28-CRP by more than 1.2, compared with control patients who are not treated with the neutralizing antibody or functional fragment thereof as used according to the invention.

The clinical benefit may comprise remission of RA. Typically, remission is defined by a DAS28-CRP of less than 2.6. In patients treated as described herein, the time to onset of remission may be reduced compared with patients who are not treated with a neutralizing antibody or functional fragment thereof according to the invention time to remission may be reduced. It is also of clinical benefit to achieve low disease activity in those patients where remission is not achieved.

According to the present invention, the neutralizing antibody or a functional fragment thereof specifically binding primate GM-CSF for use in the treatment of improves the radiographically measurable ACR criteria, preferably the neutralizing antibody or functional fragments thereof achieve an ACR of at least 20, e.g., at least 30, e.g., at least 40, 50, 60, or 70.

The clinical benefit of using the neutralizing antibody or functional fragment thereof according to the invention may be an improvement of at least 20%, at least 50% or at least 70% treatment efficacy as determined by the 1987 ACR criteria, i.e. the clinical benefit may be achieving ACR 20, ACR 50 or ACR 70, respectively. The clinical benefit comprises achieving ACR 20 in at least 40, 50, 55, 60, 65 or 70% of patients. It may comprise achieving ACR 50 in at least 20, 25, 30, 35 or 40% of patients. It may comprise achieving ACR 70 in at least 5%, 10%, 15 or 20% of patients with insufficiently controlled RA by MTX treatment alone, or patients with insufficiently controlled RA by MTX treatment and anti-TNF treatment.

A form of clinical benefit that is of particular value to RA patients is an improvement in their ability to perform everyday activities. Methods of the invention may comprise improvement in the patient's self-assessed disability measured by the Health Assessment Questionnaire, known as HAQ-DI. The following categories are assessed by the HAQ-DI: dressing and grooming, arising, eating, walking, hygiene, reach, grip, common daily activities. The patients report the amount of difficulty they have in performing some of these activities. Each question asks on a scale ranging from 0 to 3 if the categories can be performed without any difficulty (scale 0) up to cannot be done at all (scale 3) (Ramey D R, Fries J F, Singh G. The Health Assessment Questionnaire 1995-status and review. In: Quality of Life and pharmacoeconomics in clinical trials. Second edition. Edited by B Spilker. Lippincott-Raven Publishers, Philadelphia, 1996). Methods comprising providing clinical benefit to an RA patient, wherein the clinical benefit comprises improving physical function of an RA patient as determined by HAQ-DI, and compositions and kits for use in such methods, are all aspects of the invention. Clinical benefit may comprise improving physical function of an RA patient as determined by HAQ-DI. Preferably, a statistically significant improvement in HAQ-DI is achieved within twelve, ten, eight or six weeks of starting treatment according to the invention, e.g., within four weeks, or within two weeks. The improvement may be at least a 0.25 improvement in HAQ-DI, i.e. a reduction of 0.25 or more in the patient's HAQ-DI score. Preferably, the improvement is at least a 0.30, 0.40 or 0.45 improvement in HAQ-DI score. Improvement is generally measured with reference to the patient's baseline average HAQ-DI score prior to treatment with an inhibitor according to the invention. Where a group of patients is treated, the improvement may be observed in at least 50%, at least 60% or at least 70% of treated patients. The clinical benefit may be achieved sooner in treated patients compared with patients who are not treated with an inhibitor according to the invention. For example, patients who are treated with an inhibitor according to the invention in combination with methotrexate may achieve clinical benefit sooner than patients treated with methotrexate alone. The time to onset of response, or period of treatment before the clinical benefit is achieved, may be decreased by at least 10%, at least 20%, at least 30%, at least 40% or at least 50% compared with patients who are not treated with the inhibitor. Preferably, the clinical benefit is achieved within 85 days. So, for example, DAS28-CRP may be decreased by more than 1.2 within 85 days. More preferably, the onset of response occurs within 2 weeks. Thus, clinical benefit may be achieved within 14 days of treatment with the neutralizing antibody according to the invention or functional fragment thereof.

Patients may be monitored during and/or following a course of treatment with the inhibitor, to assess the level of clinical benefit, for example by measuring DAS28-CRP and/or determining clinical benefit according to the ACR criteria and/or measuring HAQ-DI. The method may comprise determining that the clinical benefit is achieved, e.g. that the specified reduction in DAS28-CRP, and/or achievement of ACR20, ACR50 or ACR70 is met, and/or that the HAQ-DI score is improved.

According to the present invention, the neutralizing antibody or a functional fragment thereof specifically binding primate GM-CSF for use in the treatment of pain emanating from an inflammatory disease, e.g., RA, in a patient to provide clinical benefit as measured by a decrease in DAS28-CRP by more than 1.2 within 85 days, the method comprising administering a composition comprising the neutralizing antibody to GM-CSF or a functional fragment thereof to the patient, wherein the composition is administered at a dose of 20 mg or 50 mg or 80 mg or 150 mg/month after two initial injections of the same dose on day d0 and about 14 days later by subcutaneous administration.

In accordance with the present invention, the neutralizing antibody or a functional fragment thereof specifically binding primate GM-CSF for use in the treatment of pain emanating from an inflammatory disease, e.g., RA to provide clinical benefit as measured by an improvement of at least ACR50 or at least ACR70 within about 7 weeks, the method comprising administering a composition comprising the neutralizing antibody or functional fragment thereof to the patient, wherein the composition is administered at a dose of 20 mg or of 50 mg or of 80 mg or of 150 mg/month after two initial injections of the same dose on day d0 and about 14 days later by parenteral, e.g., subcutaneous administration.

In accordance with the present invention, the neutralizing antibody or a functional fragment thereof specifically binding primate GM-CSF for use in the treatment of pain emanating from an inflammatory disease, e.g., RA for inducing remission of RA in a patient, as measured by a DAS28-CRP of less than 2.6, the method comprising administering a composition comprising a therapeutically effective amount of the neutralizing antibody or functional fragment thereof to the patient, wherein the composition is administered by subcutaneous administration, and wherein the onset of remission is seen after about 12 weeks after the initial administration of the neutralizing antibody or functional fragments disclosed herein.

In accordance with the present invention, the neutralizing antibody or a functional fragment thereof specifically binding primate GM-CSF for use in the treatment of pain emanating from an inflammatory disease, e.g., RA, resulting in an improvement of physical function of an RA patient, as determined by HAQ-DI, is used in a method comprising administering a composition comprising the neutralizing antibody or a functional fragment thereof specifically binding GM-CSF to the patient, wherein the composition is administered in a dose of 10-150 mg, e.g., at a dose of 10-30 mg, e.g., 20 mg, or at a dose of 50-150 mg, e.g., at a dose of 80 mg, or at a dose of 100-300 mg, e.g., at a dose of 150 mg, in 1 ml monthly by subcutaneous administration, and wherein an improvement in HAQ-DI is achieved within twelve weeks, e.g., wherein the improvement is a reduction of at least 0.25 in the patient's HAQ-DI score.

In accordance with the present invention, the methods according to present invention for the treatment of subject having moderate, moderate to severe, or severe rheumatoid arthritis are specifically suited for patients that are insufficiently controlled by either methotrexate (MTX) alone, or by MTX in combination with at least one other chemical DMARD and/or at least one TNF-inhibitor.

Within the context of the present invention, "Insufficiently controlled RA" means that a status of low disease activity (DAS28CRP≤3.2) is not reached or remission is not achieved (DAS28CRP<2.6) after about 12 weeks to 24 weeks. In additional feature may be, that also no inhibition of progression of joint destruction is identified on X-ray (only controlled after ½ year and then every 1 year).

The patients to be treated according to the invention may have a mild, or mild to moderate, or a moderate, or a moderate to severe, or either a severe form of RA. In preferred embodiments of treatments of the present invention, the patients have moderate, moderate to severe or severe disease activity. These patients are generally older than 18 years, e.g. 18 to 30 years of age, or 30 to 40 years old, or 40 to 50 years old, or older than 50 years. In another embodiment, the patients may be juvenile patients.

Based on the distribution of pain Visual analogue scores (VAS) in postsurgical patients (knee replacement, hysterectomy, or laparoscopic myomectomy) who described their postoperative pain intensity as none, mild, moderate, or severe, the following cut points on the pain VAS have been recommended: no pain (0-4 mm), mild pain (5-44 mm), moderate pain (45-74 mm), and severe pain (75-100 mm) (Jensen M P, Chen C, Brugger A M. Interpretation of visual analog scale ratings and change scores: a reanalysis of two clinical trials of postoperative pain. J Pain 2003; 4:407-14; Sokka T. Assessment of pain in rheumatic diseases. Clin Exp Rheumatol. 2005 September-October; 23(5 Suppl 39):S77-84).

Patients may be monitored during and/or following a course of treatment with the inhibitor, to assess the level of VAS morning stiffness severity by Visual Analogue Scale (VAS) to evaluate Severity of morning stiffness on a 10-cm horizontal line with 0=none on the left and 10=very severe on the right.

Measurement of morning stiffness in RA patients by a VAS for severity was found to be a responsive endpoint measure. Especially in clinical trials in which the effects of a therapy directed toward reduction of morning stiffness are evaluated assessment of morning stiffness by means of a VAS for severity appears to be a useful instrument. (Vliet Vlieland T P, Zwinderman A H, Breedveld F C, Hazes J M. Measurement of morning stiffness in rheumatoid arthritis clinical trials. J Clin Epidemiol. 1997 July; 50(7):757-63).

Patients may be monitored during and/or following a course of treatment with the inhibitor, to assess the level of VAS fatigue by a Visual Analogue Scale to Evaluate Fatigue Severity (VAS-F) consists of 18 items related to fatigue and energy. Each line is 100 mm in length. Fatigue (items 1-5 and 11-18) and energy (items 6-10) (Hewlett S, Hehir M, Kirwan J R. Measuring fatigue in rheumatoid arthritis: a systematic review of scales in use. Arthritis Rheum. 2007 Apr. 15; 57(3):429-39).

Patients may be monitored during and/or following a course of treatment with the inhibitor, to assess the level of neuropathic pain by using a Neuropathic pain questionnaire, the self-report version of the Leeds Assessment of Neuropathic Symptoms and Signs pain scale (S-LANSS: Bennett M I, Smith B H, Torrance N, Potter J. The S-LANSS score for identifying pain of predominantly neuropathic origin: validation for use in clinical and postal research. J Pain. 2005 March; 6(3):149-58).

Insufficiently controlled pain means, that the pain associated with RA is not alleviated when the patient is treated either with MTX alone or with MTX in combination with other chemical DMARDs or one TNF inhibitor.

The invention relates to the treatment of pain in connection with inflammatory and degenerative joint diseases selected from the list comprising, rheumatoid arthritis, SLE, psoriatic arthritis, ankylosing spondylitis, juvenile idiopathic arthritis, or osteoarthritis, including musculoskeletal and also neuropathic pain. Neuropathic pain may be present in patients with any of the above indications in the absence of concomitant signs of inflammation.

It is contemplated that the present methods and compositions may be employed for the treatment of pain from chronic conditions (including inhibiting progression of and/or reversing damage associated with chronic conditions). Chronic conditions include, for example, arthritic conditions such as osteoarthritis, rheumatoid arthritis, and psoriatic arthritis. For example, the present methods and compositions may be used to treat one or more symptoms or signs of osteoarthritis of the joint, (such as a hip or knee) or the back (for example, the lower back). Chronic conditions also include, for example, conditions associated with or resulting from pain such as chronic pain, including pain associated with or arising from cancer, from infection or from the nervous system (e.g., neurogenic pain such as peripheral neurogenic pain following pressure upon or stretching of a peripheral nerve or root or having its origin in stroke, multiple sclerosis or trauma, including of the spinal cord). Chronic conditions also include, for example, conditions associated with or arising from psychogenic pain (e.g., pain not due to past disease or injury or visible sign of damage inside or outside the nervous system). The present methods and compositions may also be employed for the treatment of back pain from other arthritic conditions, including gout and spondylarthropathies (including ankylosing spondylitis, Reiter's syndrome, psoriatic arthropathy, enteropathic spondylitis, juvenile arthropathy or juvenile ankylosing spondylitis, and reactive arthropathy).

The present methods and compositions may be used for the treatment of back pain from infectious or post-infectious arthritis (including gonoccocal arthritis, tuberculous arthritis, viral arthritis, fungal arthritis, syphilitic arthritis, and Lyme disease).

In further preferred embodiments of the methods of the present invention, the treatment alleviates fatigue and/or sleeping disturbances associated with pain (as determined using the MOS sleep scale or any other suitable scale). Intended to assess the extent of sleep problems, the MOS Sleep Scale measures six dimensions of sleep, including initiation, maintenance (e.g. staying asleep), quantity, adequacy, somnolence (e.g. drowsiness), and respiratory impairments (e.g. shortness of breath, snoring) (Hays R D, Stewart A L. Sleep measures. In Stewart A L & Ware J E. (eds.), Measuring Functioning and Well-being: The Medical Outcomes Study Approach. Durham, N.C.: Duke University Press, 1992, pp. 235-259).

In accordance with the methods of the present invention, the patient's mean pain experience is reduced for at least 1 year subsequent to the start of treatment (as determined by the patient using the Mean Change in VAS pain).

In accordance with the methods of the present invention, structural joint damages do not advance for at least 1 year subsequent to the start of treatment as determined using X-ray to determine the erosion score or the joint space narrowing compared with the corresponding parameters before the start of the inventive treatment.

In accordance with the methods of the present invention, the disease activity (DAS28-CRP) after at least 12 weeks subsequent to the start of treatment, e.g., at least 24 weeks subsequent to the start of treatment is reduced.

Primary Efficacy Values:
DAS28-CRP
CRP, C-reactive protein to be measured in serum
Tender joints counts (TJC) 28 joints
Swollen joints counts (SJC) 28 joints
VAS Patients global assessment disease activity on a visual analog scale In accordance with the methods of the present invention, the serum levels contains 50% of the anti-primate GM-CSF antibody or functional fragment thereof at least 7 days, at least 14 days, at least 21 days, e.g., at least 28 days after the last administration of an composition comprising the neutralizing antibody or functional fragment thereof according to the invention. Generally, the serum contains about 50% of the anti-primate GM-CSF antibody or functional fragment thereof at 28 days after the last administration. Preferably, the serum contains 50% of the anti-primate GM-CSF antibody or functional fragment thereof at 21 days after the last administration. The half-life of the anti-primate GM-CSF antibody may be at least 21 days, or at least about 25 days or longer.

In accordance with the methods of the present invention, the methods the treatment alleviate pain-associated fatigue and/or sleeping disturbances determined as VAS fatigue on the MOS sleep scale.

In accordance with the methods of the present invention, the methods the patient's pain symptoms remit for at least 1 year subsequent to the start of treatment.

In accordance with the methods of the present invention, the methods structural joint damages do not advance for at least 1 year subsequent to the start of treatment.

In accordance with the methods of the present invention, the disease activity (DAS28CRP) after at least 12 weeks subsequent to the start of treatment, e.g., at least 24 weeks subsequent to the start of treatment is reduced.

In further embodiments, the following clinical parameters may be measured: ePRO tool instruction, ePRO VAS pain; VAS Fatigue, VAS morning stiffness; S-LANSS Score; Neuropathic pain questionnaire; Joint-X ray, RAID+flare questions, SF-36v2. These PRO will be assessed daily to investigate effect on pain (with the exception of X-ray, Raid and SF-36).

In accordance with the methods of the present invention, the treatment of pain comprises the subcutaneous administration of the above-described analgesic compositions or neutralizing antibody or functional fragment thereof. The analgesic compositions, or the neutralizing antibody or functional fragments thereof of the present invention may be administered subcutaneously in the inventive methods of treatment of pain, e.g. at doses of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, of 300 mg, or higher. It is preferred that the analgesic compositions, or the neutralizing antibody or functional fragments thereof of the present invention is administered subcutaneously at doses of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 225 mg, 250 mg, 275 mg, of 300 mg, in at least 3, e.g., at least 5, e.g., at least 7 doses over a period of at least 21 weeks. It is, however, possible to administer fewer or more of doses according to the specific requirements and the patient's characteristics (e.g. depending on severity of disease, gender, age, weight, other drugs used, etc.). The duration of the treatment may be at least 21 weeks, but it is contemplated that the therapeutic methods of the invention are set forth as long as necessary. It is also contemplated that MTX is administered at the same time according to standard therapeutic regimen (e.g. 7.5 mg to 25 mg MTX per week as suggested in the Guidelines of the British Society for Rheumatology of July 2000), e.g., at a dose of 7.5 to 15 mg/week.

It is also possible to administer the herein disclosed analgesic compositions of the neutralizing antibody or functional fragments thereof for any of the above time periods, but with intervals, e g administer the compositions or active ingredients for 2, 3, or 4 weeks or 1, 2, or 3 months and use an interval of 2, 3, or 4 weeks or 1, 2, or 3 months, where no analgesic composition is administered. At the same time, administration of MTX at the above indicated weekly doses should be continued, optionally accompanied by supplementary administration of folic acid/folinic acid on the days where MTX is not administered.

In accordance with the methods of the present invention, the neutralizing antibodies against GM-CSF or functional fragments thereof are administered according to regimens set forth in the appended claims.

In accordance with the methods of the present invention, administration of any of the herein disclosed analgesic compositions, or of the neutralizing antibody or functional fragments thereof in a pharmaceutically acceptable carrier, e.g., in a pharmaceutically acceptable carrier that allows for subcutaneous administration is contemplated. In accordance with the methods of the present invention, administration of the analgesic composition or neutralizing antibody or functional fragment thereof results in an about ≥20%, about ≥25%, about ≥30%, ≥40%, or about ≥50% reduction of pain as measured on the 100 mm VAS scale after 12 weeks.

In accordance with the methods of the present invention, administration of the analgesic composition or neutralizing antibody or functional fragment thereof results in an about ≥20 points, about ≥25 points, about ≥30 points, about ≥40 points, or about >50 points reduction of pain according to the 100 mm VAS scale after 12 weeks.

In accordance with the methods of the present invention, administration of the analgesic composition or neutralizing antibody or functional fragment thereof results in an in vivo half-life of the active ingredient of about 2 to 6 weeks, e.g. about 3 to 4 weeks after administration to the patient.

Accordingly one aspect of the invention relates to a human monoclonal antibody or functional fragment thereof which specifically binds to and neutralizes primate GM-CSF.

The term "specifically binds" or related expressions such as "specific binding", "binding specifically", "specific binder" etc. as used herein refer to the ability of the human monoclonal antibody or functional fragment thereof to discriminate between primate GM-CSF and any number of other potential antigens different from primate GM-CSF to such an extent that, from a pool of a plurality of different antigens as potential binding partners, only primate GM-CSF is bound, or is significantly bound. Within the meaning of the invention, primate GM-CSF is "significantly" bound when, from among a pool of a plurality of equally accessible different antigens as potential binding partners, primate GM-CSF is bound at least 10-fold, e.g., 50-fold, e.g., 100-fold or greater more frequently (in a kinetic sense) than any other antigen different than primate GM-CSF. Such kinetic measurements can be performed on a Biacore apparatus.

As used herein, "neutralization," "neutralizer," "neutralizing" and grammatically related variants thereof refer to partial or complete attenuation of the biological effect(s) of GM-CSF. Such partial or complete attenuation of the biological effect(s) of GM-CSF results from modification, interruption and/or abrogation of GM-CSF-mediated signal transduction, as manifested, for example, in altering activation of cells, e.g. neurons, in particular nociceptive neurons, intracellular signaling, cellular proliferation or release of soluble substances, up- or down-regulation of intracellular gene activation, for example that resulting in expression of surface receptors for ligands other than GM-CSF. As one of skill in the art understands, there exist multiple modes of determining whether an agent, for example an antibody in question or functional fragment thereof is to be classified as a neutralizer. As an example, this may be accomplished by a standard in vitro test performed generally as follows: In a first proliferation experiment, a cell line, the degree of proliferation of which is known to depend on the activity of GM-CSF, is incubated in a series of samples with varying concentrations of GM-CSF, following which incubation the degree of proliferation of the cell line is measured. From this measurement, the concentration of GM-CSF allowing half-maximal proliferation of the cells is determined. A second proliferation experiment is then performed employing in each of a series of samples the same number of cells as used in the first proliferation experiment, the above-determined concentration of GM-CSF and, this time, varying concentrations of an antibody or functional fragment thereof suspected of being a neutralizer of GM-CSF. Cell proliferation is again measured to determine the concentration of antibody or functional fragment thereof sufficient to effect half-maximal growth inhibition. If the resulting graph of growth inhibition vs. concentration of antibody (or functional fragment thereof) is sigmoid in shape, resulting in decreased cell proliferation with increasing concentration of antibody (or functional fragment thereof), then some degree of antibody-dependent growth inhibition has been effected, i.e. the activity of GM-CSF has been neutralized to some extent. In such a case, the antibody or functional fragment thereof may be considered a "neutralizer" in the sense of the present invention. One example of a cell line, the degree of proliferation of which is known to depend on the activity of GM-CSF, is the TF-1 cell line, as described in Kitamura, T. et al. (1989). J Cell Physiol 140, 323-34. As one of ordinary skill in the art understands, the degree of cellular proliferation is not the only parameter by which neutralizing capacity may be established. For example, measurement of the level of signaling molecules (e.g. cytokines), the level of secretion of which depends on GM-CSF, may be used to identify a suspected GM-CSF neutralizer.

Other examples of cell lines which can be used to determine whether an antibody in question or functional fragment thereof is a neutralizer of primate GM-CSF activity include AML-193 (Lange, B. et al (1987). Blood 70, 192-9); GF-D8 (Rambaldi, A. et al (1993). Blood 81, 1376-83); GM/SO (Oez, S. et al (1990). Experimental Hematology 18, 1108-11); M07E (Avanzi, G. C. et al. (1990). Journal of Cellular Physiology 145, 458-64); TALL-103 (Valtieri, M. et al. (1987). Journal of Immunology 138, 4042-50); UT-7 (Komatsu, N. et al (1991). Cancer Research 51, 341-8).

As used herein, DMARDs (disease-modifying anti-rheumatic drugs) designates a group of synthetic drugs (not biologics) which are conventionally used in the treatment of RA to slow down disease progression. Often, the term is used to distinguish drugs from non-steroidal anti-inflammatory drugs and steroids. Examples of DMARD, anti-folate compounds such as methotrexate (MTX), hydroxychloroquine, auranophine, azathioprine, chloroquine, ciclosporin A, D-penicillamine, leflunomide, minocycline, sulfasalzine, and others. According to the invention, MTX is the DMARD generally used in combination therapy with the herein described neutralizing antibodies or functional fragments thereof of GM-CSF.

As used herein, the term "biologics" designates drugs that have been produced using biotechnological methods, e.g. therapeutic antibodies such as adalimumab, etanercept, golimumab, infliximab, and others.

As used herein, the term "TNF inhibitor" designates a biological drug that specifically targets TNFα or a receptor of TNFα. Drugs targeting TNF are for example the above-mentioned adalimumab, etanercept, golimumab, or infliximab.

Furthermore, it is also possible to use other biologics in combination with the analgesic compositions of the present invention, for example monoclonal antibodies targeting CD20, for example rituximab, or antibodies targeting other cytokines or cytokine receptors, for example tocilizumab, which targets the IL-6 receptor, or antibodies targeting the GM-CSF-receptor, anti-IL 17.

Pain may be analyzed in various animal models (J. S. Mogil, Nature Reviews Neuroscience, 2009, April 10(4): 283-294). The activity of rodent antibodies targeting GM-CSF was analyzed in mice with experimentally induced osteoarthritis (WO2010/071923). In contrast to the rodent antibodies used in animals in the osteoarthritis model, the human antibody or functional fragment thereof according to the invention is monoclonal. As used herein, the term "monoclonal" is to be understood as having the meaning typically ascribed to it in the art, namely an antibody (or its corresponding functional fragment) arising from a single clone of an antibody-producing cell such as a B cell, and recognizing a single epitope on the antigen bound.

It is particularly difficult to prepare human antibodies which are monoclonal. In contrast to fusions of murine B cells with immortalized cell lines, fusions of human B cells with immortalized cell lines are not viable. Thus, the human monoclonal antibody of the invention is the result of overcoming significant technical hurdles generally acknowledged to exist in the field of antibody technology. The monoclonal nature of the antibody makes it particularly well suited for use as a therapeutic agent, since such antibody will exist as a single, homogeneous molecular species which can be well-characterized and reproducibly made and purified. These factors result in a product whose biological activity can be predicted with a high level of precision, very important if such a molecule is going to gain regulatory approval for therapeutic administration in humans.

It is especially important that the monoclonal antibody (or corresponding functional fragment) according to the invention be a human antibody (or corresponding functional fragment). In contemplating an antibody agent intended for therapeutic administration to humans, it is highly advantageous that this antibody is of human origin. Following administration to a human patient, a human antibody or functional fragment thereof will most probably not elicit a strong immunogenic response by the patient's immune system, i.e. will not be recognized as being a "foreign", that is non-human protein. This means that no host, i.e. patient antibodies will be generated against the therapeutic antibody which would otherwise block the therapeutic antibody's activity and/or accelerate the therapeutic antibody's elimination from the body of the patient, thus preventing it from exerting its desired therapeutic effect.

The term "human" antibody as used herein is to be understood as meaning that the antibody of the invention, or its functional fragment, comprises (an) amino acid sequence(s) contained in the human germ line antibody repertoire. For the purposes of definition herein, an antibody, or its functional fragment, may therefore be considered human if it consists of such (a) human germ line amino acid sequence(s), i.e. if the amino acid sequence(s) of the antibody in question or functional fragment thereof is (are) identical to (an) expressed human germ line amino acid sequence(s). An antibody or functional fragment thereof may also be regarded as human if it consists of (a) sequence(s) that deviate(s) from its (their) closest human germ line sequence(s) by no more than would be expected due to the imprint of somatic hyper mutation. Additionally, the antibodies of many non-human mammals, for example rodents such as mice and rats, comprise VH CDR3 amino acid sequences which one may expect to exist in the expressed human antibody repertoire as well. Any such sequence(s) of human or non-human origin which may be expected to exist in the expressed human repertoire would also be considered "human" for the purposes of the present invention.

In accordance with the present invention, the primate GM-CSF is human (*Homo sapiens*) GM-CSF or non-human primate GM-CSF. Especially preferred variants of non-human primate GM-CSF include gibbon monkey (*Nomascus concolor*, also known as the western black crested gibbon) GM-CSF and GM-CSF of monkeys of the *macaca* family, for example rhesus monkey (*Macaca mulatta*) GM-CSF and cynomolgous monkey (*Macaca fascicularis*) GM-CSF. According to this embodiment of the invention, the human monoclonal antibody or functional fragment thereof exhibits cross reactivity between both human and at least one of the monkey species mentioned above. This is especially advantageous for an antibody molecule which is intended for therapeutic administration in human subjects, since such an antibody will normally have to proceed through a multitude of tests prior to regulatory approval, of which certain early tests involve non-human animal species. In performing such tests, it is generally desirable to use as a non-human species a species bearing a high degree of genetic similarity to humans, since the results so obtained will generally be highly predictive of corresponding results which may be expected when administering the same molecule to humans. However, such predictive power based on animal tests depends at least partially on the comparability of the molecule, and is very high when, due to cross-species reactivity, the same therapeutic molecule may be administered to humans and animal models. As in this embodiment of the invention, when an antibody molecule is cross reactive for the same antigen in humans as in another closely related species, tests may be performed using the same antibody molecule in humans as in this closely related species, for example in one of the monkey species mentioned above. This increases both the efficiency of the tests themselves as well as predictive power allowed by such tests regarding the behavior of such antibodies in humans, the ultimate species of interest from a therapeutic standpoint.

In accordance with the present invention, the human monoclonal antibody may be an IgG antibody. As is well known in the art, an IgG comprises not only the variable antibody regions responsible for the highly discriminative antigen recognition and binding, but also the constant regions of the heavy and light antibody polypeptide chains normally present in endogenously produced antibodies and, in some cases, even decoration at one or more sites with carbohydrates. Such glycosylation is generally a hallmark of the IgG format, and portions of these constant regions make up the so called Fc region of a full antibody which is known to elicit various effector functions in vivo. In addition, the Fc region mediates binding of IgG to Fc receptor, hence prolonging half life in vivo as well as facilitating homing of the IgG to locations with increased Fc receptor presence. Advantageously, the IgG antibody is an IgG1 antibody or an IgG4 antibody, formats which are preferred since their mechanism of action in vivo is particularly well understood and characterized. This is especially the case for IgG1 antibodies.

In accordance with the present invention, the functional fragment of the human monoclonal antibody may be an scFv, a single domain antibody, an Fv, a VHH antibody, a diabody, a tandem diabody, a Fab, a Fab' or a F(ab)$_2$. These formats may generally be divided into two subclasses, namely those which consist of a single polypeptide chain, and those which comprise at least two polypeptide chains. Members of the former subclass include an scFv (comprising one VH region and one VL region joined into a single polypeptide chain via a polypeptide linker); a single domain antibody (comprising a single antibody variable region) such as a VHH antibody (comprising a single VH region). Members of the latter subclass include an Fv (comprising one VH region and one VL region as separate polypeptide chains which are non-covalently associated with one another); a diabody (comprising two non-covalently associated polypeptide chains, each of which comprises two antibody variable regions—normally one VH and one VL per polypeptide chain—the two polypeptide chains being arranged in a head-to-tail conformation so that a bivalent antibody molecule results); a tandem diabody (bispecific single-chain Fv antibodies comprising four covalently linked immunoglobulin variable—VH and VL—regions of two different specificities, forming a homodimer that is twice as large as the diabody described above); a Fab (comprising as one polypeptide chain an entire antibody light chain, itself comprising a VL region and the entire light chain constant region and, as another polypeptide chain, a part of an antibody heavy chain comprising a complete VH region and part of the heavy chain constant region, said two polypeptide chains being intermolecularly connected via an interchain disulfide bond); a Fab' (as a Fab, above, except with additional reduced disulfide bonds comprised on the antibody heavy chain); and a F(ab)$_2$ (comprising two Fab' molecules, each Fab' molecule being linked to the respective other Fab' molecule via interchain disulfide bonds). In general, antibody functional fragments of the type described hereinabove allow great flexibility in tailoring, for example, the pharmacokinetic properties of an antibody desired for therapeutic administration to the particular exigencies at hand. For example, it may be desirable to reduce the size of the antibody administered in order to increase the degree of tissue penetration when treating tissues known to be poorly vascularized (for example, joints). Under some circumstances, it may also be desirable to increase the rate at which the therapeutic antibody is eliminated from the body, said rate generally being accelerable by decreasing the size of the antibody administered.

According to the invention, said human monoclonal antibody or functional fragment thereof may be present in monovalent monospecific; multivalent monospecific, in particular bivalent monospecific; or multivalent multispecific, in particular bivalent bispecific forms. In general, a multivalent monospecific, in particular bivalent monospecific antibody such as a full human IgG as described hereinabove may bring with it the therapeutic advantage that the neutralization effected by such an antibody is potentiated by avidity effects, i.e. binding by the same antibody to multiple molecules of the same antigen, here primate GM-CSF. Several monovalent monospecific forms or functional fragments of the antibody of the invention have been described above (for example, an scFv, an Fv, a VHH or a single domain antibody). Multivalent multispecific, in particular bivalent bispecific forms of the human monoclonal anti-primate GM-CSF antibody of the invention may include a full IgG in which one binding arm binds to primate GM-CSF while the other binding arm of which binds to another antigen different from primate GM-CSF. A further multivalent multispecific, in particular bivalent bispecific form may advantageously be a human single chain bispecific antibody, i.e. a recombinant human antibody construct comprising two scFv entities as described above, connected into one contiguous polypeptide chain by a short interposed polypeptide spacer as generally known in the art (see for example WO 99/54440 for an anti-CD19×anti-CD3 bispecific single chain antibody). Here, one scFv portion of the bispecific single chain antibody comprised within the bispecific single chain antibody will specifically bind primate GM-CSF as set out above, while the respective other scFv portion of this bispecific single chain antibody will bind another antigen determined to be of therapeutic benefit.

In accordance with the present invention, the human monoclonal antibody or functional fragment thereof may be derivatized, for example with an organic polymer, for example with one or more molecules of polyethylene glycol ("PEG") and/or polyvinyl pyrrolidone ("PVP"). As is known in the art, such derivatization can be advantageous in modulating the pharmacodynamic properties of antibodies or functional fragments thereof. Especially preferred are PEG molecules derivatized as PEG-maleimide, enabling conjugation with the antibody or functional fragment thereof in a site-specific manner via the sulfhydryl group of a cysteine amino acid. Of these, especially preferred are 20 kD and/or 40 kD PEG-maleimide, in either branched or straight-chain form. It may be especially advantageous to increase the effective molecular weight of smaller human anti-primate GM-CSF antibody functional fragments such as scFv functional fragments by coupling the latter to one or more molecules of PEG, especially PEG-maleimide.

In accordance with the present invention, the human monoclonal antibody or functional fragment thereof specifically binds to an epitope, in particular to a discontinuous epitope, of human or non-human primate GM-CSF comprising amino acids 23-27 (RRLLN) (SEQ ID NO: 57) and/or amino acids 65-77 (GLR/QGSLTKLKGPL) (SEQ ID NO: 58).

The variability at position 67 within the amino acid sequence stretch 65-77 depicted above reflects the heterogeneity in this portion of primate GM-CSF between, on the one hand, human and gibbon GM-CSF (in which position 67 is R) and, on the other hand, monkeys of the *macaca* family, for example cynomolgous and rhesus monkeys (in which position 67 is Q).

As used herein, the numbering of human and non-human primate GM-CSF refers to that of mature GM-CSF, i.e. GM-CSF without its 17 amino acid signal sequence (the total length of mature GM-CSF in both human and non-human primate species described above is 127 amino acids). The sequence of human GM-CSF and gibbon GM-CSF is as follows:

```
                                          (SEQ ID NO: 49)
APARSPSPST QPWEHVNAIQ EARRLLNLSR DTAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE.
```

The sequence of GM-CSF in certain members of the *macaca* monkey family such as for example rhesus monkey and cynomolgous monkey is as follows:

```
                                          (SEQ ID NO: 50)
APARSPSPGT QPWEHVNAIQ EARRLLNLSR DTAAEMNKTV

EVVSEMFDLQ EPSCLQTRLE LYKQGLQGSL TKLKGPLTMM

ASHYKQHCPP TPETSCATQI ITFQSFKENL KDFLLVIPFD

CWEPVQE.
```

The minimum epitope, advantageously a discontinuous epitope, bound by the human monoclonal antibody of the invention (or functional fragment thereof) as described above is indicated in the above GM-CSF sequence in boldface. As used herein, the term "discontinuous epitope" is to be understood as at least two non-adjacent amino acid sequence stretches within a given polypeptide chain, here mature human and non-human primate GM-CSF, which are simultaneously and specifically (as defined above) bound by an antibody. According to this definition, such simultaneous specific binding may be of the GM-CSF polypeptide in linear form. Here, one may imagine the mature GM-CSF polypeptide forming an extended loop, in one region of which the two sequences indicated in boldface above line up, for example more or less in parallel and in proximity of one another. In this state they are specifically and simultaneously bound by the antibody functional fragment of the invention. According to this definition, simultaneous specific binding of the two sequence stretches of mature GM-CSF indicated above may also take the form of antibody binding to a conformational epitope. Here, mature GM-CSF has already formed its tertiary conformation as it normally exists in vivo (Sun, H. W., J. Bernhagen, et al. (1996). Proc Natl Acad Sci USA 93, 5191-6). In this tertiary conformation, the polypeptide chain of mature GM-CSF is folded in such a manner as to bring the two sequence stretches indicated above into spatial proximity, for example on the outer surface of a particular region of mature, folded GM-CSF, where they are then recognized by virtue of their three-dimensional conformation in the context of the surrounding polypeptide sequences.

In accordance with the present invention, the above (discontinuous) epitope further comprises amino acids 28-31 (LSRD), italicized in the above sequences of human and non-human primate GM-CSF. In an especially preferred embodiment, either of the above (discontinuous) epitopes further comprises amino acids 32-33 (TA) and/or amino acids 21-22 (EA), each of which stretch is underlined in the above sequences of human and non-human primate GM-CSF.

In accordance with the present invention, the human monoclonal antibody or functional fragment thereof, or compositions or medicaments according to the invention comprising such antibodies or functional fragments, comprise in its heavy chain variable region a CDR3 comprising an amino acid sequence chosen from the group consisting of those set out in any of the SEQ ID NOs: 1-13 or 56. Preferred is a human monoclonal antibody or functional fragment thereof comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 1; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 2; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 3; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 4; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 5; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 6; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 7; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 8; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 9; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 10; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 11; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 12; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 13; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 56.

In accordance with the present invention, any of the above 14 combinations of CDR1, CDR2 and CDR3 sequences exists in a human monoclonal antibody or functional fragment thereof further comprising in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

Analgesic compositions or medicaments according to the invention comprising the above antibodies or functional fragments or uses thereof are embodiments of the invention.

In accordance with the present invention, the human monoclonal antibody of the invention or functional fragment thereof comprises in its light chain variable region an amino acid sequence as set out in SEQ ID NO: 19. Preferred is a human monoclonal antibody or functional fragment thereof, the light chain variable region comprising an amino acid sequence as set out in SEQ ID NO: 19 and a heavy chain variable region comprising an amino acid sequence as set out in SEQ ID NO: 20; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 21; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 22; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 23; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 24; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 25; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 26; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 27; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 28; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 29; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 30; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 31; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 32; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 33; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 52; or a human monoclonal antibody or functional fragment thereof, the light chain variable region comprising an amino acid sequence as set out in SEQ ID NO: 19 and a heavy chain variable region comprising an amino acid sequence as set out in SEQ ID NO: 53.

In accordance with the present invention, the human monoclonal antibody of the invention or functional fragment thereof comprises in its light chain variable region an amino acid sequence as set out in SEQ ID NO: 54. Preferred is a human monoclonal antibody or functional fragment thereof, the light chain variable region comprising an amino acid sequence as set out in SEQ ID NO: 54 and a heavy chain variable region comprising an amino acid sequence as set out in SEQ ID NO: 20; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 21; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 22; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 23; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 24; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 25; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 26; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 27; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 28; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 29; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 30; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 31; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 32; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 33; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 52; or a human monoclonal antibody or functional fragment thereof, the light chain variable region comprising an amino acid sequence as set out in SEQ ID NO: 54 and a heavy chain variable region comprising an amino acid sequence as set out in SEQ ID NO: 53.

In accordance with the present invention, the human monoclonal antibody of the invention or functional fragment thereof comprises in its light chain variable region an amino acid sequence as set out in SEQ ID NO: 55. Preferred is a human monoclonal antibody or functional fragment thereof, the light chain variable region comprising an amino acid sequence as set out in SEQ ID NO: 55 and a heavy chain variable region comprising an amino acid sequence as set out in SEQ ID NO: 20; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 21; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 22; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 23; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 24; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 25; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 26; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 27; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 28; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 29; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 30; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 31; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 32; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 33; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 52; or a human monoclonal antibody or functional fragment thereof, the light chain variable region comprising an amino acid sequence as set out in SEQ ID NO: 55 and a heavy chain variable region comprising an amino acid sequence as set out in SEQ ID NO: 53.

In accordance with the present invention, a human monoclonal antibody or functional fragment thereof is used, said antibody comprising in its light chain a variable region a CDR1 region comprising an amino acid sequence as set out in SEQ ID NO: 16, a CDR2 region having an amino acid sequence as set out in SEQ ID NO: 17 and a CDR3 having an amino acid sequence as set out in SEQ ID NO: 18 and comprising in its heavy chain variable region a CDR1 region comprising an amino acid sequence as set out in SEQ ID NO: 14, a CDR2 region having an amino acid sequence as set out in SEQ ID NO: 15 and a CDR3 having an amino acid sequence as set out in any of SEQ ID NOs. 1, 2, 3, 4, 5, 6, 7, 8, 9, 10, 11, 12, 13 or 56, e.g., the heavy chain variable region comprises a CDR3 having an amino acid sequence set out in SEQ ID No. 2.

Analgesic compositions or medicaments according to the invention or kits comprising the above antibodies or functional fragments or uses thereof are embodiments of the invention.

In accordance with the present invention, the human monoclonal antibody comprises in its light chain an amino acid sequence as set out in SEQ ID NO: 34 and in its heavy chain an amino acid sequence as set out in SEQ ID NO: 35; or in its light chain an amino acid sequence as set out in SEQ ID NO: 34 and in its heavy chain an amino acid sequence as set out in SEQ ID NO: 36; or in its light chain an amino acid sequence as set out in SEQ ID NO: 34 and in its heavy chain an amino acid sequence as set out in SEQ ID NO: 37; or in its light chain an amino acid sequence as set out in SEQ ID NO: 34 and in its heavy chain an amino acid sequence as set out in SEQ ID NO: 38; or in its light chain an amino acid sequence as set out in SEQ ID NO: 34 and in its heavy chain an amino acid sequence as set out in SEQ ID NO: 39; or in its light chain an amino acid sequence as set out in SEQ ID NO: 34 and in its heavy chain an amino acid sequence as set out in SEQ ID NO: 40; or in its light chain an amino acid sequence as set out in SEQ ID NO: 34 and in its heavy chain an amino acid sequence as set out in SEQ ID NO: 41; or in its light chain an amino acid sequence as set out in SEQ ID NO: 34 and in its heavy chain an amino acid sequence as set out in SEQ ID NO: 42; or in its light chain an amino acid sequence as set out in SEQ ID NO: 34 and in its heavy chain an amino acid sequence as set out in SEQ ID NO: 43; or in its light chain an amino acid sequence as set out in SEQ ID NO: 34 and in its heavy chain an amino acid sequence as set out in SEQ ID NO: 44; or in its light chain an amino acid sequence as set out in SEQ ID NO: 34 and in its heavy chain an amino acid sequence as set out in SEQ ID NO: 45; or in its light chain an amino acid sequence as set out in SEQ ID NO: 34 and in its heavy chain an amino acid sequence as set out in SEQ ID NO: 46; or in its light chain an amino acid sequence as set out in SEQ ID NO: 34 and in its heavy chain an amino acid sequence as set out in SEQ ID NO: 47; or in its light chain an amino acid sequence as set out in SEQ ID NO: 34 and in its heavy chain an amino acid sequence as set out in SEQ ID NO: 48. Neutralizing antibodies comprising in the light chain an amino acid sequence as set out in SEQ ID NO: 34 and in its heavy chain an amino acid sequence as set out in SEQ ID NO: 35, or functional fragments of such antibodies, are embodiments of the invention.

Analgesic compositions or medicaments comprising the above antibodies or functional fragments or uses thereof are embodiments of the invention.

In accordance with the present invention, human monoclonal antibody molecules and/or functional fragments thereof are provided which are especially advantageous as neutralizers of the activity of primate, especially of human GM-CSF. Human monoclonal antibodies or functional fragments thereof are highly advantageous for several reasons.

First, they recognize primate GM-CSF highly specifically, that is to say that from a mixture of primate GM-CSF with other primate colony stimulating factors (for example primate G-CSF and M-CSF), the binding molecules according to these especially preferred embodiments are highly discriminating for primate GM-CSF, whereas the other colony stimulating factors in the same milieu are not recognized. This means that a human monoclonal antibody or functional fragment thereof according to these embodiments, when administered to a human, will be expected to specifically bind to and neutralize only the desired target, whereas other undesired targets are neither bound nor neutralized. Ultimately, this leads to a high degree of predictability concerning the therapeutic mode of action in vivo.

Second, binders according to these especially preferred embodiments bind to primate GM-CSF with extremely high affinity. $K_D$ values of from about $4 \times 10^{-9}$ M down to as low as about 0.04×10⁻⁹ M, the latter corresponding to about 40 pM, have been observed for molecules of this class. Since the kinetic on-rate of such molecules in aqueous media is largely diffusion controlled and therefore cannot be improved beyond what the local diffusion conditions will allow under physiological conditions, the low $K_D$ arises primarily as a result of the kinetic off-rate, $k_{off}$, which for the highest affinity antibody binder is approximately $10^{-5\ -s}$. This means that once the complex between a human monoclonal antibody or functional fragment thereof according to any of these embodiments of the invention on the one hand and primate GM-CSF on the other hand is formed, it does not readily, or at least does not quickly separate. For binding molecules intended as neutralizers of biological activity, these characteristics are highly advantageous since the desirable neutralizing effect will normally last only as long as the molecule, the biological activity of which is to be neutralized (here primate GM-CSF) remains bound by the neutralizing binding molecule. So a neutralizing molecule which remains bound to its intended target for a long time will continue to neutralize for a correspondingly long time.

The high binding affinity of human monoclonal antibodies or functional fragments thereof to primate GM-CSF has an additional advantage. Normally, antibodies or functional fragments thereof will be eliminated from the bloodstream of a patient in a size-dependent fashion, with smaller molecules being excreted and eliminated before larger ones. Since the complex of the two polypeptides—antibody or antibody functional fragment and bound GM-CSF—is obviously larger than the antibody alone, the low $k_{off}$ mentioned above has the effect that therapeutic neutralizer is excreted and eliminated from the patient's body more slowly than would be the case, were it not bound to GM-CSF. Thus, not only the magnitude of the neutralizing activity but also its duration in vivo is increased.

Accordingly, when the antibodies or functional fragments are used in methods according to the invention or to provide analgesic medicaments or analgesic pharmaceutical compositions, the duration of pain reduction can be extended compared with less specific analgesics. An advantage of the antibodies or functional fragments or compositions and medicaments of the present invention is that the period between two administrations of the herein described medicaments, compositions or the active ingredients can be extended. Alternatively, the amount of active ingredients in compositions comprising the same as analgesic compound, due to its high affinity to GM-CSF, may be shortened compared with other analgesics that are less specific. This property of the compositions, medicaments, etc. of the present invention increases patient compliance.

Finally, the neutralizing activity determined for binders according to these especially preferred embodiments is surprisingly high. As will be described in more detail herein below, neutralizing activity was measured in vitro using a TF-1 growth inhibition assay (Kitamura, T. et al. (1989). J Cell Physiol 140, 323-34). As an indication of neutralizing potential, $IC_{50}$ values were measured, $IC_{50}$ representing the concentration of human monoclonal antibody or functional fragment thereof according to any of these embodiments of the invention required to elicit a half-maximal inhibition of TF-1 cell proliferation. For human monoclonal antibodies or functional fragments thereof according to any of these embodiments of the invention an $IC_{50}$ value of approximately $3\times10^{-10}$ M, or about 0.3 nM was determined. The binding molecules according to any of these embodiments of the invention are therefore highly potent neutralizes of the activity of primate GM-CSF.

In summary, then, a human monoclonal antibody or functional fragment thereof according to any of the above embodiments of the invention exhibits high degree of discrimination for the desired antigen, binds this antigen extremely tightly and for a long time and exhibits highly potent neutralizing activity for the long time it remains bound. At the same time, the long persistence of the binder-antigen complex slows elimination of this binder from the body, thereby lengthening the duration of the desired therapeutic effect in vivo, and thereby advantageously extending the time interval between two administrations of compositions or medicaments according to the invention comprising the active ingredients in the treatment of pain.

A further aspect of the invention provides a human monoclonal antibody or functional fragment thereof comprising an amino acid sequence having at least 70%, at least 75% at least 80% at least 85% at least 90% at least 95%, e.g., at least 97% homology with an amino acid as set out in any of SEQ ID NOs: 1-48 and/or 52-56. Homology may be determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). As the term is used herein, two amino acids in question are considered as being "conservative substitutions" of one another if they each belong to the same chemical class, i.e. acidic, nonpolar, uncharged polar and basic. By way of non-limiting example, two different amino acids belonging to the class of nonpolar amino acids would be considered "conservative substitutions" of one another, even if these two amino acids were not identical, whereas a nonpolar amino acid on the one hand and a basic amino acid on the other hand would not be considered "conservative substitutions" of one another. Panel 3.1 of "Molecular Biology of the Cell", $4^{th}$ Edition (2002), by Alberts, Johnson, Lewis, Raff, Roberts and Walter groups amino acids into four main groups: acidic, nonpolar, uncharged polar and basic. Such a grouping may be used for the purposes of determining, for the purposes of the present invention, whether or not a particular amino acid is a conservative substitution of another amino acid in question.

A further aspect of the invention provides a polynucleotide molecule having a nucleotide sequence encoding an amino acid sequence as set out in any of SEQ ID NOs: 1-48 and/or 52 to 56 or a nucleotide sequence exhibiting at least 70%, at least 75% at least 80% at least 85% at least 90% at least 95%, e.g., at least 97% homology therewith, wherein homology may be determined by comparing a nucleotide sequence encoding an amino acid sequence of any of SEQ ID NOS: 1-48 and/or 52-56 with a nucleotide sequence in question by sequence alignment (as described above for amino acid sequences), wherein a nucleotide in the sequence in question is considered homologous if it is either identical to the corresponding nucleotide in the nucleotide sequence encoding a corresponding amino acid sequence of any of SEQ ID NOs: 1-48 and/or 52-56 or if one or more nucleotide deviation(s) in the sequence in question from the corresponding one or more nucleotide(s) in the nucleotide sequence encoding an amino acid sequence of any of SEQ ID NOs: 1-48 and/or 52-56 results in a nucleotide triplet which, when translated, results in an amino acid which is either identical to (due to a degenerate triplet) or a conservative substitution of the corresponding amino acid in the corresponding amino acid sequence of any of SEQ ID NOs:

1-48 and/or 52-56. Here, the term "conservative substitution" is to be understood as described above.

A further aspect of the invention provides a pharmaceutical composition comprising a human monoclonal antibody or functional fragment thereof or a polynucleotide molecule having a nucleotide sequence encoding an amino acid sequence as set out in any of SEQ ID NOs: 1-48 and/or 52-56 or encoding an amino acid sequence comprising an amino acid sequence bearing at least 70%, at least 75% at least 80% at least 85% at least 90% at least 95%, e.g., at least 97% homology to any of SEQ ID NOs: 1-48 and/or 52-56, wherein "homology" is to be understood as explained hereinabove. In accordance with this invention, the term "pharmaceutical composition" relates to a composition for administration to a patient, e.g., a human patient. In a preferred embodiment, the pharmaceutical composition comprises a composition for parenteral, transdermal, subcutaneous, intraluminal, intra-arterial, intrathecal and/or intranasal administration or by direct injection into tissue. It is in particular envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. In preferred embodiments of the present invention, the analgesic compositions are suitable for subcutaneous administration. Methods of treatment of subjects, e.g., human subjects according to the present invention involve the subcutaneous administration of analgesic compositions as described throughout the present disclosure. These methods comprise the administration of the inventive compositions to patients suffering from pain, e.g. pain-associated with RA. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, liposomes, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the pharmaceutical composition of the present invention might comprise proteinaceous carriers, like, e.g., serum albumin or immunoglobulin, e.g., of human origin. It is envisaged that the pharmaceutical composition of the invention might comprise, in addition to the human monoclonal antibody or functional fragment thereof (as described in this invention), further biologically active agents, depending on the intended use of the pharmaceutical composition. Such agents might be drugs acting on the gastrointestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines or other analgesics, e.g. NSAIDs, COX-2 inhibitors, tramadol hydrochloride, known in the art, antibiotic and antimicrobial drugs, anticoagulation drugs, cholesterol reducing drugs, statins, anti-depressive drugs, antihypertensive drugs, nitroglycerin, and other heart medication drugs. The dosage of such additional compounds will also be determined by the attending physician and clinical factors, e.g. the patient's size, body surface area, age, the particular compound to be administered, sex, time and route of administration, general health, and other drugs being administered concurrently.

It is of particular importance that the neutralizing antibodies and/or functional fragments thereof provide a sufficient stability upon storage. It is possible to produce a wide variety of proteins for therapeutic applications. After their production, protein pharmaceuticals are usually stored prior to their use. Due to the fact that proteins are generally larger and more complex than "traditional" pharmaceuticals, formulation and processing of protein pharmaceuticals that are suitable for storage can be particularly challenging. For reviews of protein pharmaceutical formulation and process design, see Carpenter et al. (1997), Pharm. Res. 14: 969-975; Wang (2000), Int. J. Pharmaceutics 203: 1-60; and Tang and Pikal (2004), Pharm. Res. 21: 191-200. Several factors can be considered in designing formulations and processes for protein pharmaceutical production. Of primary concern is the stability of the protein through any or all steps of manufacture, shipping, and handling steps, which may include preparation of the composition, freezing, lyophilizing, drying, storage, shipping, reconstitution, freeze/thaw cycles, and post-reconstitution storage by the end user. Other potential considerations include ease and economy of manufacture, handling, and distribution; composition of the final product for patient administration; and ease of use by the end user, including solubility of the lyophilized formulation upon reconstitution.

Stable formulation comprising the neutralizing anti-GM-CSF antibody or functional fragments thereof according to the present invention can be regarded as an aqueous solution, wherein the antibody or functional fragments thereof are directly dissolved and/or dispersed therein. An embodiment of the present invention is a liquid formulation containing the antibody or functional fragments thereof which is stable and does not undergo the formation of conjugates/aggregates or functional fragments/degradation products when stored for a long period, and which formulation is suitable for subcutaneous administration.

Specifically, the neutralizing anti-GM-CSF antibody or functional fragments thereof could be stabilized if a tonicity modifier is added to the solution which is to be stored. Examples for tonicity modifiers include, but are not limited to, sugars and sugar alcohols. Simple sugars are called monosaccharides and include glucose, fructose, galactose, xylose, ribose, mannose, lactulose, allose, altrose, gulose, idose, talose, arabinose and lyxose. More preferred for the present inventions are disaccharides which include for example sucrose, maltose, lactose, isomaltose, trehalose and cellubiose. Sugar alcohols include sorbitol, mannitol, glycerin, erythritol, maltitol, xylitol, polyglycitol. In a preferred embodiment, the sugar is a non-reducing sugar such as sucrose or trehalose. Non-reducing sugars are characterized by the absence of an open chain structure, so they are not susceptible to oxidation-reduction reactions. Therefore one or more of non-reducing sugars, such as sucrose or trehalose, or one or more of sugar alcohols, such as mannitol or sorbitol could be added to the formulation comprising a compound neutralizing GM-CSF. Also combinations of non-reducing sugars and sugar alcohols could be added to the solution, such as sucrose and mannitol, sucrose and sorbitol, trehalose and mannitol, or trehalose and sorbitol. More preferably the sugar alcohols mannitol and/or sorbitol are added, e.g., in their D-form, most preferably sorbitol is added to the solution. The concentration of the tonicity modifier, e.g., sorbitol, is between about 1% and about 15% (w/v), e.g., between about 2% and about 10% (w/v), e.g., between about 3% and about 7% (w/v), e.g., between about 4% and about 6% (w/v) and preferably about 5% (w/v).

Another specifically preferred substance to stabilize the neutralizing anti-GM-CSF antibody or functional fragments thereof at a high concentration with regard to long-term storage is a buffer system with a pH of between about 4 and about 10, e.g., between about 4 and about 7, e.g., between about 4 and about 6 or between about 5 and about 7, e.g., between about 5.5 and about 6.5, preferably with a pH of about 5.8. The buffer may be preferably selected from a histidine buffer, an acetate buffer and a citrate buffer. When referred herein, an amino acid is meant to be an L-amino acid or D-amino acid, wherein L-amino is preferred. Preferably histidine or a salt thereof is used for the buffer system. Preferably the salt is a chloride, phosphate, acetate or sulphate, more preferably the salt is a chloride. The pH of the histidine buffer system is between about 5 and about 7, preferably between about 5.5 and about 6.5, more preferred the pH is about or exactly 5.8. The pH may be adjusted by the use of conventionally used bases and acids, preferably NaOH. The concentration of the buffer system, preferably the histidine buffer system, is between about 10 mM and about 50 mM, preferably between about 20 mM and about 40 mM, more preferably about 30 mM.

According to a preferred embodiment, a combination of the buffer system, preferably the histidine buffer, and the tonicity modifier, preferably the sugar alcohol, more preferably mannitol or even more preferably sorbitol, is used to stabilize the neutralizing anti-GM-CSF antibody or functional fragments thereof in the solution, in order to prevent aggregation and to render the formulation sufficiently stable for long-term storage and/or one or more freeze/thaw cycles. It was shown that it is preferable in terms of stability to have about 6% (w/v) and higher of sugar alcohol, preferably sorbitol, in the formulation. However, the upper limit for osmolality of the formulation is set to be about 470 mOsm/kg which is still hyperosmotic. A preferable concentration of sugar alcohol, preferably sorbitol, is therefore between about 3% and about 7% (w/v), more preferably between about 4% and about 6% (w/v) and most preferably about 5% (w/v). In some embodiments of the present invention, the formulations or compositions of the invention comprising the neutralizing anti-GM-CSF antibody or functional fragments thereof do not require further excipients in addition to those disclosed above (i.e., a buffer and a tonicity modifier), such as, for example, surfactants and amino acids, which are used in traditional formulations to stabilize proteins in solution. In addition, the formulations described herein are preferred over standard formulations because they have decreased immunogenicity due to the lack of additional agents commonly needed for protein stabilization. It is known that amino acids are useful to stabilize proteins at a high concentration by, inter alia, mediating protein solubility and/or inhibiting protein aggregation. Although threonine (e.g. at 250 mM) indicates a minor stabilizing effect, the liquid formulation comprising the neutralizing anti-GM-CSF antibody or functional fragments thereof is preferably free from further amino acids.

Furthermore, it is preferred that the present formulation is free or essentially free of sodium chloride. By "essentially free" is meant that the concentration of sodium chloride is at or very near to 0 (zero) mM, e.g. less than about 50 mM, preferably less than about 20 mM, more preferably less than about 10 mM, even more preferably less than about 5 mM and most preferably less than about 2 mM or even less than about 1 mM.

In biopharmaceutical products, the addition of surfactants can be useful to reduce protein degradation during storage. The polysorbates 20 and 80 (Tween 20 and Tween 80) are well established excipients for this purpose.

In a more preferred embodiment the polysorbate 20 to protein ratio is between about 0.01:1 to about 3:1, preferably between about 0.05:1 to about 2:1, more preferably between about 0.1:1 and about 1.5:1, even more preferably between about 0.1:1 to about 0.8:1, and most preferably between about 0.1:1 to about 0.2:1. For a protein concentration of 80 mg/mL, the polysorbate 20 concentration is between about 0.001% (w/v) and about 0.2% (w/v), preferably between about 0.005% (w/v) and about 0.15% (w/v), more preferably between about 0.007% (w/v) and about 0.1% (w/v), even more preferably between about 0.007% (w/v) and about 0.06% (w/v) and most preferably about 0.01% (w/v). For a protein concentration of 150 mg/mL, the polysorbate 20 concentration is between about 0.001% (w/v) and about 0.4% (w/v), preferably between about 0.006% (w/v) and about 0.25% (w/v), more preferably between about 0.01% (w/v) and about 0.18% (w/v), even more preferably between about 0.01% (w/v) and about 0.1% (w/v) and most preferably about 0.02% (w/v).

In another more preferred embodiment, the polysorbate 80 to protein ratio is between about 0.01:1 to about 3:1, preferably between about 0.05:1 to about 2:1, more preferably between about 0.1:1 and about 1.5:1, even more preferably between about 0.1:1 to about 0.6:1, and most preferably from about 0.3:1 to about 0.6:1. For a protein concentration of 80 mg/mL, the polysorbate 80 concentration is between about 0.001% (w/v) and about 0.2% (w/v), preferably between about 0.004% (w/v) and about 0.14% (w/v), more preferably between about 0.007% (w/v) and about 0.1% (w/v), even more preferably between about 0.007% (w/v) and about 0.05% (w/v), and most preferably about 0.04% (w/v). For a protein concentration of 150 mg/mL, the polysorbate 80 concentration is between about 0.001% (w/v) and about 0.4% (w/v), preferably between about 0.007% (w/v) and about 0.26% (w/v), more preferably between about 0.01% (w/v) and about 0.2% (w/v), even more preferably between about 0.01% (w/v) and about 0.08% (w/v), most preferably about 0.04% (w/v).

The concentration of the neutralizing anti-GM-CSF antibody or functional fragments thereof used is at least about 20 mg/ml, preferably at least about 50 mg/ml, more preferably at least about 100 mg/ml in the liquid formulation which is to be stored, freeze/thawed and/or ready to use. Concentrations of about 20 mg/ml to about 200 mg/mg, preferably about 50 mg/ml to about 200 mg/ml, more preferably about 100 mg/ml to about 180 mg/ml, even more preferably about 130 mg/ml to about 170 mg/ml, even more preferably about 135 mg/ml to about 165 mg/ml, and most preferred about 150 mg/ml are used in the present invention. Another preferred concentration of the neutralizing anti-GM-CSF antibody or functional fragments thereof used is about 80 mg/ml.

Furthermore, in one embodiment, the present formulation of the neutralizing anti-GM-CSF antibody or functional fragments thereof comprises from about 135 mg/ml to about 165 mg/ml of the neutralizing antibody, about 5% (w/v) sorbitol, about 30 mM L-histidine and has a pH of about 5.8.

Furthermore, in one embodiment, the present formulation of the neutralizing anti-GM-CSF antibody or functional fragments thereof comprises from about 80 mg/ml to about 150 mg/ml of the neutralizing antibody, about 5% (w/v) sorbitol, about 30 mM L-histidine, and from about 0.01% to about 0.08% (w/v) polysorbate 80 and has a pH of about 5.8.

Furthermore, in one embodiment, the present formulation of the neutralizing anti-GM-CSF antibody or functional fragments thereof comprises about 80 mg/ml to of the neutralizing antibody, about 5% (w/v) sorbitol, about 30 mM L-histidine, about 0.04% (w/v) polysorbate 80 and has a pH of about 5.8.

Furthermore, in one embodiment, the present formulation of the neutralizing anti-GM-CSF antibody or functional fragments thereof comprises about 150 mg/ml to of the neutralizing antibody, about 5% (w/v) sorbitol, about 30 mM L-histidine, about 0.04% (w/v) polysorbate 80 and has a pH of about 5.8.

The shelf life of the produced liquid formulation has a preferred minimum requirement of 24 months at 2 to 8° C., preferably 36 months at 2 to 8° C., more preferably 48 months at 2 to 8° C. or at least 28 days at ambient temperature (25° C.±2° C.).

The neutralizing anti-GM-CSF antibody or functional fragments thereof is provided in a stable formulation, e.g., a stable liquid formulation that surprisingly allows for long-term storage of compounds neutralizing GM-CSF. This formulation is useful, in part, because it is more convenient to use for the patient, as the neutralizing anti-GM-CSF antibody or functional fragments thereof of this formulation are highly concentrated so as to reduce side effects like pain due to high volume injection.

Accordingly, the formulations comprising a neutralizing anti-GM-CSF antibody or functional fragments thereof according to the invention comprise a buffer system preferably selected from a histidine buffer, an acetate buffer and/or a citrate buffer with a preferred pH of between 5 and 7, and a tonicity modifier preferably selected from non-reducing sugars, such as sucrose or trehalose, or sugar alcohols, such as mannitol or sorbitol are rendered sufficiently stable for long-term storage and/or freeze/thaw cycles. The formulation of the invention has many advantages over standard buffered formulations. In one aspect, the formulation shows minimal aggregation behaviour upon long-term storage without deleterious effects that might be expected with high protein formulations. Other advantages of the formulation according to the invention are: minimal functional fragmentation of neutralizing anti-GM-CSF antibody or functional fragments thereof and no significant impact on bioactivity of neutralizing anti-GM-CSF antibody or functional fragments thereof over long-term storage, and low viscosity of the composition. Finally, in a preferred embodiment, the formulation is free of further excipients such as surfactants, additional amino acids and/or sodium chloride.

A further aspect of the invention provides a use of a human monoclonal antibody or functional fragment thereof as described hereinabove or a polynucleotide molecule comprising a nucleotide sequence encoding an amino acid sequence as set out in any of SEQ ID NOs: 1-48 and/or 52-56 or encoding an amino acid sequence comprising an amino acid sequence bearing at least 70% homology, at least 75% at least 80% at least 85% at least 90% at least 95%, e.g., at least 97% to any of SEQ ID NOs: 1-48 and/or 52-56, wherein "homology" is to be understood as explained hereinabove, in the manufacture of a medicament for the treatment of rheumatoid arthritis, SLE, psoriatic arthritis, ankylosing spondylitis, juvenile idiopathic arthritis, or osteoarthritis with concomitant pain, e.g., rheumatoid arthritis (RA), including RA which is insufficiently controlled by treatment with MTX and/or TNF inhibitors.

A further aspect of the invention provides a use of a human monoclonal antibody or functional fragment thereof as described hereinabove or a polynucleotide molecule comprising a nucleotide sequence encoding an amino acid sequence as set out in any of SEQ ID NOs: 1-48 and/or 52-56 or encoding an amino acid sequence comprising an amino acid sequence bearing at least 70% homology, at least 75% at least 80% at least 85% at least 90% at least 95%, e.g., at least 97% to any of SEQ ID NOs: 1-48 and/or 52-56, wherein "homology" is to be understood as explained hereinabove in the manufacture of a medicament, optionally comprising one or more analgesics, e.g. NSAIDs, COX-2 inhibitors, anti-inflammatory agents, e.g. methotrexate, etc. are especially preferred. Furthermore, the antibodies or functional fragments thereof or homologs thereof can be used in the manufacture of a medicament further comprising antagonists of the receptor for GM-CSF (GM-CSF-receptor), wherein the antagonists may be small molecules, small blocking peptides or antibodies neutralizing the activity of the GM-CSF-receptor, e.g. through prevention of the binding of natural ligand (GM-CSF) or any molecules that induce downstream signaling events, e.g., downstream signaling in neurons expressing the GM-CSF-receptor. The prevention of downstream signaling may be determined by any suitable method for the measurement of the activation of neurons, e.g. patch-clamp methods measuring the ion-flux, or other methods known in the art. Additionally, the present methods and compositions may be used for the treatment of arthritis associated with various syndromes, diseases, and conditions, such as arthritis associated with vasculitic syndrome, arthritis associated with polyarteritis nodosa, arthritis associated with hypersensitivity vasculitis, arthritis associated with Luegenec's granulomatosis, arthritis associated with polymyalgin rheumatica, and arthritis associated with joint cell arteritis. Other preferred indications contemplated for employing the compositions and methods herein include calcium crystal deposition arthropathies (such as pseudo gout), non-articular rheumatism (such as bursitis, tenosynovitis, epicondylitis, carpal tunnel syndrome, and repetitive use injuries), neuropathic joint disease, hemarthrosis, Henoch-Schonlein Purpura, hypertrophic osteoarthropathy, and multicentric reticulohistiocytosis. Other preferred indications contemplated for employing the compositions and methods herein include arthritic conditions associated with sarcoidosis, hemochromatosis, sickle cell disease and other hemoglobinopathies, hyperlipoproteineimia, hypogammaglobulinemia, hyperparathyroidism, acromegaly, familial Mediterranean fever, Behcet's Disease, lupus (including systemic lupus erythematosus), hemophilia, relapsing polychondritis, lumbago, and pain associated with herniated disc.

The present disclosure relates to compositions, dosage forms, and kits with a neutralizing antibody specifically binding to primate GM-CSF or a functional fragment thereof in the treatment of pain optionally in combination with another analgesic, wherein the amount of said analgesic enhances the potency of the analgesic of the present invention, or wherein the amounts of the neutralizing antibody specifically binding to primate GM-CSF or a functional fragment thereof and the amount of the other analgesic together are effective to alleviate (e.g., ameliorate, attenuate, reduce, diminish, block, inhibit or prevent) one or more symptoms or signs of an arthritic condition, or chronic pain. The disclosure further relates to methods for administering to human subjects such compositions, dosage forms, and kits.

The methods comprise administering to a human subject an amount of a neutralizing antibody specifically binding to primate GM-CSF or a functional fragment thereof or the combination of said neutralizing antibody specifically binding to primate GM-CSF or a functional fragment thereof, and another analgesic that is effective to enhance potency of the neutralizing antibody specifically binding to primate GM-CSF or a functional fragment thereof and/or to alleviate one or more symptoms or signs of an arthritic condition or pain associated with a chronic condition, including for example, as measured by a suitable index, scale or measure. The attenuation of one or more symptoms or signs of an arthritic may be measured on the WOMAC Osteoarthritis Index or one of its subscales (in other words, the pain, stiffness, or physical function subscales of the WOMAC Osteoarthritis Index). Any suitable version of the WOMAC OA Index may be used, including, for example, Version 3.0 or Version 3.1. Any suitable scale may be used as well. The WOMAC OA Index is available in Likert and Visual Analog scaled formats, either of which may be employed in the present methods. WOMAC values can be considered as surrogate markers for the diagnosis, prognosis, monitoring or treatment of an arthritic condition, and/or chronic pain. The WOMAC values represent a subjective surrogate marker. Alternatively or additionally, the attenuation of one or more symptoms or signs may be measured on another suitable index, scale or measure, such the Australian/Canadian (AUSCAN) Osteoarthritis Hand Index or the Osteoarthritis Global Index (OGI). The AUSCAN 3.1 Index and User Guide are currently available from http://www.womac.org/contact/index.cfm, as are the WOMAC 3.1 Osteoarthritis Index and User Guide. Another suitable measure of attenuation is the Definition of Improvement in Rheumatoid Arthritis described in Felson et al., Arthritis & Rheumatism 38:727-735 (1995) incorporated herein by reference. This measure, which also may be designated as the ACR (American College of Rheumatology) 20 improvement, is a composite defined as both improvement of 20% in the number of tender and number of swollen joints, and a 20% improvement in three of the following five: patient global, physician global, patient pain, patient function assessment, and C-reactive protein (CRP). Another suitable measure is described by Paulus et al., Arthritis & Rheumatism 33:477-484 (1990) which is incorporated herein by reference. Paulus et al. provides a definition of improvement based on a set of measures that discriminate between active second-line drug treatment and placebo. These include a 20% improvement in morning stiffness, erythrocyte sedimentation rate (ESR), joint tenderness score, and joint swelling score and improvement by at least 2 grades on a 5-grade scale (or from grade 2 to grade 1) for patient and physician global assessments of current disease severity. Current disease severity can be measured in a variety of ways, including patient or physician global assessments, patient or physician assessments of joint tenderness, joint swelling stiffness, pain, or physical function, cytokine levels, B-cell or T-cell subtype ratios, erythrocyte sedimentation rate (ESR), or C-reactive protein. Suitable measures of attenuation of one or more symptoms or signs, of inhibiting the progression of an arthritic condition or chronic condition, or of reversing tissue or cellular damage include measuring current disease severity. Other indexes, definitions, measures, or scales may also be used for measuring attenuation of one or more symptoms or signs, inhibition of progression, or reversal of tissue or cellular damage.

EXAMPLES

Example 1

A phase 2 multicenter, randomized, double-blind, placebo-controlled, parallel group dose finding trial with different dose arms designed to compare three different dose levels of an antibody neutralizing GM-CSF (hereinafter referred to as "anti-GM-CSF-1") comprising a light chain CDR1 as depicted in SEQ ID NO: 16, a light chain CDR2 shown in SEQ ID NO: 17, a light chain CDR3 according to SEQ ID NO: 18, a heavy chain CDR1 shown in SEQ ID NO: 14, a heavy chain CDR2 shown in SEQ ID NO: 15, and a heavy chain CDR3 as depicted in SEQ ID NO: 2 (an antibody having a variable heavy chain and light chain as specified in SEQ ID Nos. 34 and 35) is used at doses of 20 mg, 80 mg or 150 mg administered subcutaneously at week 0, 2, 6, 10, 14, 18, 22 in combination with stable continued dose of MTX versus placebo. Preparation of this antibody is disclosed in WO 2006/111353.

The effect of anti-GM-CSF-1 on disease activity and signs and symptoms will be assessed by examination of joints (66 swollen and 68 tender joints) by a blinded assessor. Acute phase reactants e.g. DAS28CRP will be measured in serum and ESR will be measured in blood at all visits. Effect on function (HAQ-DI) and Patient's and Physician's global assessment of the disease activity will be assessed using a Visual analogue scale (VAS) at all site visits.

Effect on RA pain intensity will be investigated using electronic capturing of VAS pain measures from two weeks prior to baseline and will have daily monitoring throughout the treatment period. Change in quality of pain will be assessed by questionnaires at week 1, 12 and 24. SLANSS is assessed at baseline, week 2, 12 and 24. For VAS pain it is assessed at all visits up to week 24. Quality of life and patient reported outcomes will also be explored. Change in structural joint damage (mTSS change from baseline) will be explored at week 24. The primary endpoint at week 12 (DAS28-CRP mean change from baseline) is 2 weeks after the 4th administration of anti-GM-CSF-1 or placebo.

Based on improvement in tender and swollen joint count at week 12 early escape to treatment of non-responders will be allowed from week 14.

The subject population will be subjects with moderate to severe RA for ≥6 months disease duration and insufficiently controlled by either MTX alone or MTX in combination with one or more other DMARD(s) or one prior TNF inhibitor.

A total of 324 subjects will be randomly assigned to one of the treatment groups for the treatment period in a 1:1:1:1 ratio. The baseline randomization will also cover the treatment in the active extension period, in which subjects continue on the same dose, except for subjects randomized to placebo who at week 24 will randomly be allocated to either 80 or 150 mg which will consequently be a 1:1 ratio of the (80, 150 mg) doses.

The study consists of the following periods:
Screening period (week −8/−2 to Baseline Visit).
Treatment period (Baseline Visit 3 (Day 1) to week 24).
Active extension period (week 24 to week 72).
Safety follow-up period (week 72 to week 80/12 weeks after last administration).
Study Population RA patients whose disease is not sufficiently controlled on MTX and/or other DMARDs in monotherapy or in combination or glucocorticoids (GC) at a dose of no more than 10 mg/day are eligible to have biologics added to current MTX/DMARD/GC therapy according to current recommendations.

In the trial, anti-GM-CSF-1 will be tested as second line treatment in biologic naïve patients, and as third line treatment in patients who have failed treatment with anti-TNF compounds.

Patients in the trial must have had RA defined by the 1987 ACR criteria for at least 6 months prior to trial entry. The bio-naïve patients must have been treated with MTX for three months, and are thus eligible to a second-line treatment. Patients had to have active disease defined as swollen and tender joint count ≥4 for each (referred to the 28 joint-count system), and DAS28CRP and DAS28ESR > or equal 3.2, with 4 or more swollen joints, which usually is found in RA patients with this disease activity. Furthermore the patients should be in current stable therapy with MTX.

Selecting a population with this characteristics aims to ensure that anti-GM-CSF-1 is tested in combination with the anchor drug MTX in an appropriate patient population eligible for biologic treatment and with a disease activity that gives a high probability of reducing signs and symptoms of RA.

Study Design and Sample Size

The current design offers an above 90% power to detect a relevant difference to placebo on the primary endpoint (DAS28CRP mean change from baseline at week 12).

Concomitant Medications and Controls

The choice of controls is also in accordance with the CPMP/EMA Guideline (December 2003, 4). Section 5.1 of the guideline recommends use of placebo controls for a limited duration of 3 to 6 months. The use of MTX monotherapy in the placebo arm is needed for the evaluation of superiority of any dose level of anti-GM-CSF-1 plus MTX compared to MTX alone, but also to get an indication of the magnitude of the response if it is found.

The chronic use of non-steroidal anti-inflammatory drugs (NSAIDs) with gastric protection, low dose corticosteroids and hydroxychloroquine, all in stable doses, is allowed in the study to ensure adequate medical care.

Efficacy Endpoints

The continuous endpoint DAS28 (DAS28-CRP) was selected as primary endpoint as it is considered a more sensitive endpoint for signs and symptoms compared to the more traditional dichotomous ACR20 response rates and it is an absolute parameter used in daily clinical practice to follow disease activity and has been confirmed to be a suitable parameter for the evaluation of disease activity in clinical trials with RA according to EULAR/ACR Collaborative Recommendations (Fransen and Van Riel 244; Aletaha et al. 1371-77).

To further evaluate the efficacy of anti-GM-CSF-1 in combination with MTX in reducing signs and symptoms of RA, the proportions of subjects achieving ACR 20/50/70 and EULAR good and moderate response will be assessed at time of the primary endpoint or after 24 weeks. The proportion of RA patients achieving remission as defined by DAS28-CRP, SDAI, CDAI and the new ACR/EULAR remission criteria will be assessed as secondary endpoints at week 12 and 24.

Disease modifying anti-rheumatic drugs (DMARDs) for treatment of RA have to demonstrate ability to prevent or slow progression of structural joint damage. The effect of anti-GM-CSF-1 on inhibition of structural joint damage will therefore be explored after 24 weeks treatment in this dose finding trial, as well as in an extension period up to week 72. X-rays will be assessed under blinded conditions.

Trial Duration

For the majority of biologics in RA, it will take up to 24 weeks to generate a deep inflammation control measurable as DAS28 remission or high level ACR responses such as ACR50/70. Therefore, in this trial the double blind treatment period is 24 weeks.

Active Extension Period (Week 24 to 72)

Responders at week 24 will be eligible to continue on their current double blind dose of anti-GM-CSF-1 until week 70 provided that thorough evaluation of the safety across the dose level by the DMC has not revealed any risk benefit issue that prevent an extension period. Subjects randomized at baseline to placebo and who are responders at week 24 will be eligible to continue into the active extension period randomized to one of the highest dose levels anti-GM-CSF-1 (80 mg, 150 mg) subcutaneously administered every 4 weeks for at least 12 weeks. The justification of this handling of placebo responders after 24 weeks is that achieving a low disease activity or an improvement of DAS28CRP>1.2 from baseline is not an ultimately achievable goal in RA, and an even better clinical response can be pursued in these subjects. Given they do achieve a improved clinical response (change in DAS28-CRP>1.2) after 12 weeks in the active extension period they should be eligible to continue for the whole active extension period up to week 70 on this dose.

1.1 Screening Period

Subjects will be screened at the Screening Visit between week −8 and week −3 before IMP administration, allowing for careful evaluation of the eligibility of the subjects and for the washout of TNF inhibitor and/or DMARDs except MTX (and hydroxycholoroquine and chloroquine), Three weeks prior to Baseline the subject will return to the site for visit where the eligibility will be checked, and subjects will be trained in obtaining electronic capturing of VAS pain, VAS Fatigue and morning stiffness daily from three weeks prior to baseline and until week 24.

Subjects will return to the clinic on Day 1, undergo baseline assessments and confirmation of eligibility and if eligible be randomized to one of the treatment groups in the treatment period as well as the active extension period.

1.2 The Treatment Period

Eligible subjects will return to the clinic on Day 1 when eligibility criteria will be reviewed again, vital signs will be recorded, lung functions test will be performed, clinical efficacy assessment, blood specimens will be collected and the subject will have one subcutaneous injection of anti-GM-CSF-1 or placebo.

Before leaving the site the subject will have a follow up evaluation and a blood specimen drawn for pharmacokinetic analysis.

In the treatment period (week 1 to 24) subjects will return to the study center for dosing at week 2 (w2), 6, 10, 14, 18, 22. Before dosing, vital signs, lung function test and an examination of the injection site will be undertaken. Clinical efficacy assessment (SJC and TJC) by a trained blinded assessor will be undertaken at all visits before anti-GM- CSF-1 administration. In addition a blood sample for pharmacokinetic and biomarker analysis will be drawn before anti-GM-CSF-1 administration.

Subjects will have disease activity and safety (including laboratory evaluation) assessed two weeks after first anti-GM-CSF-1 administration and subsequently every month. Nine site visits in the treatment period are planned (visit 3 to visit 11).

X-ray of hands (posteroanterior view) and forefeet (anteroposterior view) will be obtained and digitalised for blinded reading at baseline and at week 24 and for those subjects that participate in the active extension period at week 72 or at last study visit. Assessment will be done centrally by readers with no knowledge of the treatment allocations and blinded to the order at which the images had been obtained, using the van der Heijde modification of Sharp method (mTSS).

1.3 Active Extension Period (Week 24 to 72)

Subjects who at week 24 have achieved low disease activity (DAS28CRP<3.2) or have a DAS28CRP reduction ≥1.2 from baseline to week 24 will be eligible. Subjects will continue on the same dose as in the treatment period and treatment will be kept blinded. However, patients treated with placebo in the treatment period and who meet this response criteria will not continue on placebo, but will receive either 80 mg or 150 mg anti-GM-CSF-1, 1:1, in the active extension period and be eligible to continue in the active extension period up to week 72 if they achieve a low disease activity DAS28CRP<3.2 or have a DAS28CRP reduction ≥1.2 after the initial 12 weeks in the active extension period. If not they will have to leave the trial.

In the active extension period, disease activity and safety (including laboratory evaluation) will be assessed regularly the first 3 months and subsequently every 3 months until week 72.

1.4 Safety Follow Up Period (12 Weeks after Trial Completion/Premature Discontinuation)

Two site contacts, where the first one can be a phone call, are scheduled to follow up on possible adverse events and immunogenicity before end of the trial. In this period, the investigator can at own discretion start treatment of the subject per current medical practice.

For subjects who enter into the active extension period, the trial will have a total duration of up to 88 weeks.

Data on exposure of anti-GM-CSF-1 (PK) will be collected during the treatment period at all dosing visits. Furthermore, PK data will be collected during the active extension period according to the schedule of study procedures.

Example 2

A 24-week randomized, open-label, parallel-group, active-controlled, exploratory, proof-of-mechanism imaging study investigating the efficacy of 150 mg of neutralizing anti-primate GM-CSF referred to in Example 1 administered subcutaneously compared with anti-TNF antibody Adalimumab in patients with moderate to severe early RA diagnosed within 6 months and inadequately controlled by MTX alone.

A total of 36 subjects will be enrolled and will remain in the study for a maximum of 44 weeks. The study consists of the following periods:
Screening Period (Week −4/−2 to Baseline Visit).
Treatment Period (Baseline Visit [Day 1] to Week 24).
Treatment-Free Period (Week 25 to Week 40).
End of Study Visit (Week 40).

Subjects will be randomly assigned in a 2:1 ratio to the following open-label treatment groups:
1) Neutralizing anti-primate GM-CSF 300 mg subcutaneous (SC) as loading dose that is administered at Week 0 followed thereafter by 150 mg SC administered at Weeks 2, 6, 10, 14, 18, and 22 as an add-on to weekly existing stable MTX and folic acid: 24 subjects;
2) Active control, adalimumab 40 mg SC administered at Weeks 0, 2, 4, 6, 8, 10, 12, 14, 16, 18, 20, and 22 as an add-on to weekly existing stable MTX and folic acid: 12 subjects.

Primary Objective(s)

To explore the effect on structural damage imaging markers measured as change from baseline in synovitis, erosion progression and bone marrow oedema (osteitis), in metocarpophalangeal (MCP) joints and wrist at week 24 on MRI using the RAMRIS OMERACT score.

Secondary Objective(s)

To explore the effect on structural damage imaging markers measured as change from Baseline in dynamic contrast enhanced (DCE)-MRI parameters at Week 24 on MCP joints and wrist. To explore other efficacy outcomes of anti-GM-CSF in RA such as Disease Activity Score 28 based on C-reactive protein (DAS28-CRP) and the American College of Rheumatology (ACR) 20, 50, and 70 criteria. To explore the speed of onset of efficacy measured as effect on synovitis, bone marrow edema, erosion (RAMRIS) and synovial perfusion using static and DCE-MRI at Weeks 6 and 12. To evaluate the safety and tolerability of anti-GM-CSF antibody/MTX coadministration.

Endpoints

Primary Endpoints

Change from baseline in synovitis, erosion and bone marrow oedema (osteitis), on MRI of the MCP and wrist using the RAMRIS OMERACT at week 24.

Secondary Endpoints

To evaluate changes on:
Vascular perfusion of the synovium measured as a change from baseline in Dynamic Contrast Enhanced MRI (DCE-MRI) parameters at week 24. The ability to induce synovial remission (absence of synovial inflammation) will be assessed at weeks 6 and 12 using static (RAMRIS OMERACT synovitis score) and DCE-MRI parameters;
Proportion of subjects who achieved DAS28-CRP (<2.6) remission by week 24.
Proportion of subjects who achieved DAS28-CRP (<3.2) low disease activity by week 24.
Clinical disease activity measured as decrease in DAS28-CRP from baseline at all applicable post baseline visits.
Proportion of clinical remission defined as SDAI<3.3 at week 24 from baseline.
Proportion of low disease activity defined as SDAI<11 at week 24 from baseline.
Effect on signs and symptoms measured as proportion of subjects achieving ACR20, 50 and 70 at all applicable post baseline visits including visits up to week 40.

Study Subjects

Male and female adults aged 18 years with moderate to severe early RA.

The subjects have
Swollen joint count (SJC)≥4 and tender joint count (TJC) ≥4 (referred to the 28 joint-count system) at Screening and Baseline Visit; and
C-reactive protein (CRP)≥4.3 mg/L at Screening Visit and ESR≥28 mm/hr, and imaging (ultrasound powerdoppler) evidence of moderate to severe inflammation of at least one MCP joint of the dominant hand or one joint of the dominant wrist at Screening and Baseline Visit;

Received weekly MTX for at least 3 months prior to the Screening Visit; and

Received treatment with MTX≥15-25 mg/week at a stable dose via the same route of administration and formulation for at least 8 weeks prior to Baseline Visit. or Subject is on a stable dose for at least 8 weeks of MTX of ≥7.5 mg/week is acceptable, if the MTX dose have been reduced for reasons of documented intolerance to MTX, The subject is willing to continue or initiate treatment with oral folic acid (at least 5 mg/week) or equivalent and be treated during the entire trial (mandatory co-medication for MTX treatment).

Study Medication and Materials 1 ml of anti-GM-CSF-antibody 150 mg/ml solution for subcutaneous injection was administered to patient participating in the study Comparator Medication Adalimumab in an amount of 40 mg administered every other week as a single dose via subcutaneous injection. Methotrexate was continued during treatment with Adalimumab.

Companion Medication

Concomitant treatment with weekly MTX (15-25 mg) at stable doses was continued, with appropriate oral folic/(at least 5 mg/week) folinic acid supplementation or equivalent was continued during the entire study (mandatory co-medication for MTX treatment).

All study medications were administered upon visit of the participating subjects in the clinic for dosing of study drug at weeks 0, 2, 6, 10, 14, 18 and 22 if assigned to anti-GM-CSF. Subjects assigned to take adalimumab will visit the clinic for dosing of study drug at weeks 0, 2, 4, 6, 8, 10, 12, 14, 16, 18, 20 and 22.

TABLE 1

Doses administered

| Treatment Group | Dose | Treatment Description |
|---|---|---|
| Anti-GM-CSF solution for injection | 150 mg/ml | 1 ml subcutaneous injection |
| Adalimumab pre filled syringe | 40 mg | Subcutaneous injection |

Efficacy Measurements

MRI

MRI of the dominate hand and wrist were performed at Baseline and weeks 6, 12, and 24. Several MRI images were taken before and after the contract injection using, Gadolinium.

Ultrasound (US) Powerdoppler

US Powerdoppler was performed on the dominant hand or dominant wrist at screening and baseline to confirm evidence of moderate to severe inflammation for eligibility.

DAS28-CRP/ESR

The DAS28-CRP score was calculated at screening and baseline and at visits in weeks 2, 6, 10, 12, 18, 24, 32, and 40.

The Disease Activity Score 28 (DAS28) combines information relating to the number of swollen and tender joints, in addition to a measure of general health, and the acute phase response. The DAS28 is a modification of the original DAS and is based on a count of 28 swollen and tender joints and has been used to objectively evaluate a subject's response to treatment. The DAS 28 CRP utilizing joint scores from the following 28 joints: elbows, shoulders, elbow, wrists, metacarpal-phalangeals I-V, proximal interphalangeals I-V and knees. IT is calculated using the following formula:

$$DAS28(CRP)=0.56*\sqrt{(TJC28)}+0.28*\sqrt{(SJC28)}+0.014*GH+0.36*\ln(CRP+1)+0.96$$

Where TJC—Tender joint Count, SJC=Swollen Joint Count, (GH=subject assessment of disease activity using a 100 mm visual analogue scale (VAS) with 0=best, 100=worst) and CRP=C reactive Protein (in mg/L).

The DAS 28 ESR is very similar to DAS 28 CRP but utilizes ESR (Erythrocyte sedimentation rate) instead of CRP in its below formula. DAS28 (ESR) was measured by the site at randomization to check eligibility criteria.

$$DAS28(ESR)=0.56*\sqrt{(TJC28)}+0.28*\sqrt{(SJC28)}+0.014*GH+0.70*\ln(ESR)+0.70$$

ESR in mm/hour.

American College of Rheumatology (ACR) Criteria Assessment

ACR Criteria assessment was performed at screening and baseline and at the visits in weeks 2, 6, 10, 12, 18, 24, 32, and 40.

ACR20/50/70 response rate are included as secondary efficacy endpoints at all applicable post baseline visits including visits up to week 40. Responders will be defined as those subjects whose improvement from baseline to week 40 fulfils the following criteria:

≥20/50/70% reduction in the TJC (66/68).
≥20/50/70% reduction in the SJC (66/68).
≥20/50/70% reduction in three of the following additional measures:

Patient Global and Physician Global VAS, and HAQ-DI

Patient's/physician's global assessment of disease activity captures the state of disease over the previous 7 days on the day of the visit. Disease activity will be assessed by both subject and physician using a 100 mm VAS (with the endpoints 0=not active at all, and 100=extremely active). Subject and physician will mark these points on the scale using the electronic site device.

Patient's assessment of pain focused on pain (VAS pain) experienced over the previous 7 days, as recorded during study site visits. Maximum intensity of pain will be documented, as part of the HAQ-DI, by marking the respective value on a VAS contained within an electronic site device (100 mm line with the endpoints 0=no pain at all, and 100=very severe pain).

The Health Assessment Questionnaire-Disability Index (HAQ-DI) questionnaire will be the basis for the subjects' self-assessment of their health status. The HAQ-DI includes eight blocks of questions covering difficulties encountered in the previous 7 days when performing simple daily activities, such as personal hygiene (washing, and dressing or undressing), mobility domestic and outdoors (walking, mounting steps, going shopping, carrying things), as well as intake of food or drink and the handling of tools used in everyday life. Furthermore, the use of mechanical aids and the need for helpers is queried. The Investigator will check for plausibility and completeness of entries, without influencing the subjects in their assessments.

Patient Global and Physician Global VAS, and HAQ-DI were performed at screening and baseline and at the visits in weeks 2, 6, 10, 12, 18, 24, 32, and 40.

The EuroQoL Health Questionnaire (EQ-5D) was completed by the participants in the study at baseline, and in weeks 6, 12, and 24.

Safety Assessments

Safety assessments will be performed throughout the trial via the monitoring of adverse events (AEs), physical examinations, vital signs, laboratory results (haematology, serum biochemistry, and urinalysis), lung function tests and electrocardiograms (ECGs). In addition, thorough and extensive monitoring of pulmonary symptoms and signs (including pulsoximetry and a dyspnea questionnaire, at all visits, and chest x-ray and lung function testing, at selected time points) will be conducted to identify any signs of potential PAP at an early stage.

What is claimed is:

1. A method of treating an inflammatory disease in a human subject, wherein the inflammatory disease is selected from the group consisting of sarcoidosis, systemic lupus erythematosus (SLE), psoriatic arthritis, ankylosing spondylitis, juvenile idiopathic arthritis, and osteoarthritis, comprising administering to the human subject a neutralizing antibody or a functional fragment thereof that specifically binds a primate granulocyte macrophage colony-stimulating factor (GM-CSF), wherein the neutralizing antibody or functional fragment thereof is administered according to the following dosing scheme:
   i) administering a first initial dose to the human subject comprising 300 mg or 150 mg of the neutralizing antibody or a functional fragment thereof;
   ii) administering a second dose to the human subject comprising 150 mg of the neutralizing antibody or a functional fragment thereof about 14 days or about 28 days after the first initial dose;
   iii) administering a third dose to the human subject comprising 150 mg of the neutralizing antibody or a functional fragment thereof about 28 days after the second dose; and
   iv) administering one or more additional doses to the human subject comprising 150 mg of the neutralizing antibody or a functional fragment thereof with intervals of about 28 days beginning about 28 days after the third dose;
   wherein the neutralizing antibody or functional fragment thereof comprises a light chain variable region and a heavy chain variable region, wherein the light chain variable region comprises a CDR1 comprising the amino acid sequence of SEQ ID NO: 16, a CDR2 comprising the amino acid sequence of SEQ ID NO:

17, and a CDR3 comprising the amino acid sequence of SEQ ID NO: 18, and wherein the heavy chain variable region comprises a CDR1 comprising the amino acid sequence of SEQ ID NO: 14, a CDR2 comprising the amino acid sequence of SEQ ID NO: 15, and a CDR3 comprising the amino acid sequence of SEQ ID NO: 2.

2. The method of claim 1, wherein the neutralizing antibody or functional fragment thereof is administered subcutaneously.

3. The method of claim 1, wherein the neutralizing antibody or functional fragment thereof is administered subcutaneously in at least 5 or at least 7 doses over a period of at least 21 weeks.

4. The method of claim 1, wherein the light chain variable region comprises the amino acid sequence of SEQ ID NO: 19, and the heavy chain variable region comprises the amino acid sequence of SEQ ID NO: 21.

5. The method of claim 4, wherein the neutralizing antibody or functional fragment thereof is formulated for subcutaneous administration.

6. The method of claim 1, wherein the light chain comprises the amino acid sequence of SEQ ID NO: 34, and the heavy chain comprises the amino acid sequence of SEQ ID NO: 35.

7. The method of claim 6, wherein the neutralizing antibody or functional fragment thereof is formulated for subcutaneous administration.

8. The method of claim 1, wherein structural joint damage does not advance for at least 1 year subsequent to the start of treatment.

9. The method of claim 1, wherein the human subject receives at least one additional anti-inflammatory drug selected from the group consisting of disease-modifying antirheumatic drugs (DMARDs), corticosteroids, nonsteroidal anti-inflammatory drugs (NSAIDS), opioids, and biologic drugs.

10. The method of claim 9, wherein the at least one additional anti-inflammatory drug is an anti-folate compound.

11. The method of claim 10, wherein the anti-folate compound is methotrexate.

12. The method of claim 11, wherein the methotrexate is administered once weekly.

13. The method of claim 12, wherein the methotrexate is administered at a dose of 7.5 to 25 mg per administration.

14. The method of claim 9, wherein the neutralizing antibody or functional fragment thereof is formulated for subcutaneous administration.

* * * * *

```
                         SEQUENCE LISTING

<160> NUMBER OF SEQ ID NOS: 58

<210> SEQ ID NO 1
   <211> LENGTH: 10
   <212> TYPE: PRT
   <213> ORGANISM: artificial sequence
   <220> FEATURE:
   <223> OTHER INFORMATION: CDR-H3 7A-701

<400> SEQUENCE: 1

Ser Gly Leu Ile Ala Asn His Met Thr Pro
   1               5                   10

<210> SEQ ID NO 2
   <211> LENGTH: 10
   <212> TYPE: PRT
   <213> ORGANISM: artificial sequence
   <220> FEATURE:
   <223> OTHER INFORMATION: CDR-H3 7B1-502

<400> SEQUENCE: 2

Thr Thr Leu Ile Ser Val Tyr Phe Asp Tyr
   1               5                   10

<210> SEQ ID NO 3
   <211> LENGTH: 10
   <212> TYPE: PRT
   <213> ORGANISM: artificial sequence
   <220> FEATURE:
   <223> OTHER INFORMATION: CDR-H3 L38-A1

<400> SEQUENCE: 3

Ser Gly Leu Ile Phe Asp Tyr Trp Leu Asp
   1               5                   10

<210> SEQ ID NO 4
   <211> LENGTH: 10
   <212> TYPE: PRT
   <213> ORGANISM: artificial sequence
   <220> FEATURE:
   <223> OTHER INFORMATION: CDR-H3 L38-A12

<400> SEQUENCE: 4

Ser Gly Leu Ile Ile Asp Ala Leu Ser Pro
   1               5                   10

<210> SEQ ID NO 5
   <211> LENGTH: 10
   <212> TYPE: PRT
   <213> ORGANISM: artificial sequence
   <220> FEATURE:
   <223> OTHER INFORMATION: CDR-H3 L38-G7

<400> SEQUENCE: 5

Thr Ser Leu Met Ser Ile Tyr Phe Asp Tyr
   1               5                   10

<210> SEQ ID NO 6
```

```
<211> LENGTH: 10
<212> TYPE: PRT
<213> ORGANISM: artificial sequence
<220> FEATURE:
<223> OTHER INFORMATION: CDR-H3 L39-D11

<400> SEQUENCE: 6

Ser Gly Leu Leu Phe Leu Tyr Phe Asp Tyr
1               5                   10

<210> SEQ ID NO 7
<211> LENGTH: 10
<212> TYPE: PRT
<213> ORGANISM: artificial sequence
<220> FEATURE:
<223> OTHER INFORMATION: CDR-H3 E1-37-E7

<400> SEQUENCE: 7

Ser Gly Leu Ile Asn Leu Gly Met His Pro
1               5                   10

<210> SEQ ID NO 8
<211> LENGTH: 10
<212> TYPE: PRT
<213> ORGANISM: artificial sequence
<220> FEATURE:
<223> OTHER INFORMATION: CDR-H3 M1_3-82

<400> SEQUENCE: 8

Ser Gly Leu Ile Phe Asp Ala Leu Arg Asp
1               5                   10

<210> SEQ ID NO 9
<211> LENGTH: 10
<212> TYPE: PRT
<213> ORGANISM: artificial sequence
<220> FEATURE:
<223> OTHER INFORMATION: CDR-H3 Ln4p-23

<400> SEQUENCE: 9

Ser Gly Leu Ile Phe Asp Lys Leu Thr Ser
1               5                   10

<210> SEQ ID NO 10
<211> LENGTH: 10
<212> TYPE: PRT
<213> ORGANISM: artificial sequence
<220> FEATURE:
<223> OTHER INFORMATION: CDR-H3 Ln4p-28

<400> SEQUENCE: 10

Ser Gly Leu Ile Asn Leu His Phe Asp Thr
1               5                   10

<210> SEQ ID NO 11
<211> LENGTH: 10
<212> TYPE: PRT
<213> ORGANISM: artificial sequence
<220> FEATURE:
<223> OTHER INFORMATION: CDR-H3 Ln4p-50

<400> SEQUENCE: 11

Ser Thr His Phe Ser Ala Tyr Phe Asp Tyr
1               5                   10

<210> SEQ ID NO 12
<211> LENGTH: 10
```

```
<212> TYPE: PRT
<213> ORGANISM: artificial sequence
<220> FEATURE:
<223> OTHER INFORMATION: CDR-H3 Ln4p-65

<400> SEQUENCE: 12

Ser Gly Leu Ile Met Asp Lys Leu Asp Asn
1               5                   10

<210> SEQ ID NO 13
<211> LENGTH: 10
<212> TYPE: PRT
<213> ORGANISM: artificial sequence
<220> FEATURE:
<223> OTHER INFORMATION: CDR-H3 Ln4p-90

<400> SEQUENCE: 13

Ser Gly Leu Ile Ile Asp Asn Leu Asn Pro
1               5                   10

<210> SEQ ID NO 14
<211> LENGTH: 5
<212> TYPE: PRT
<213> ORGANISM: artificial sequence
<220> FEATURE:
<223> OTHER INFORMATION: CDR-H1 7B1-502

<400> SEQUENCE: 14

Asp Tyr Leu Leu His
1               5

<210> SEQ ID NO 15
<211> LENGTH: 17
<212> TYPE: PRT
<213> ORGANISM: artificial sequence
<220> FEATURE:
<223> OTHER INFORMATION: CDR-H2 7B1-502

<400> SEQUENCE: 15

Trp Leu Asn Pro Tyr Ser Gly Asp Thr Asn Tyr Ala Gln Lys Phe Gln
1               5                   10                  15

Gly

<210> SEQ ID NO 16
<211> LENGTH: 11
<212> TYPE: PRT
<213> ORGANISM: artificial sequence
<220> FEATURE:
<223> OTHER INFORMATION: CDR-L1 5-306

<400> SEQUENCE: 16

Arg Ala Ser Gln Asn Ile Arg Asn Ile Leu Asn
1               5                   10

<210> SEQ ID NO 17
<211> LENGTH: 7
<212> TYPE: PRT
<213> ORGANISM: artificial sequence
<220> FEATURE:
<223> OTHER INFORMATION: CDR-L2 5-306

<400> SEQUENCE: 17

Ala Ala Ser Asn Leu Gln Ser
1               5

<210> SEQ ID NO 18
```

```
<211> LENGTH: 9
<212> TYPE: PRT
<213> ORGANISM: artificial sequence
<220> FEATURE:
<223> OTHER INFORMATION: CDR-L3 5-306

<400> SEQUENCE: 18

Gln Gln Ser Tyr Ser Met Pro Arg Thr
1               5

<210> SEQ ID NO 19
<211> LENGTH: 107
<212> TYPE: PRT
<213> ORGANISM: artificial sequence
<220> FEATURE:
<223> OTHER INFORMATION: VL 5-306* L-version

<400> SEQUENCE: 19

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys
            100                 105

<210> SEQ ID NO 20
<211> LENGTH: 119
<212> TYPE: PRT
<213> ORGANISM: artificial sequence
<220> FEATURE:
<223> OTHER INFORMATION: VH with CDR-H3 = 7A-701

<400> SEQUENCE: 20

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
            100                 105                 110

Thr Met Val Thr Val Ser Ser
            115

<210> SEQ ID NO 21
<211> LENGTH: 119
```

```
<212> TYPE: PRT
<213> ORGANISM: artificial sequence
<220> FEATURE:
<223> OTHER INFORMATION: VH with CDR-H3 = 7B1-502*

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
                100                 105                 110

Thr Met Val Thr Val Ser Ser
            115

<210> SEQ ID NO 22
<211> LENGTH: 119
<212> TYPE: PRT
<213> ORGANISM: artificial sequence
<220> FEATURE:
<223> OTHER INFORMATION: VH with CDR-H3 = 3077*

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
                100                 105                 110

Thr Met Val Thr Val Ser Ser
            115

<210> SEQ ID NO 23
<211> LENGTH: 119
<212> TYPE: PRT
<213> ORGANISM: artificial sequence
<220> FEATURE:
<223> OTHER INFORMATION: VH with CDR-H3 = L38-A1

<400> SEQUENCE: 23

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
```

```
                        20                  25                  30
Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Tyr Trp Leu Asp Trp Gly Gln Gly
            100                 105                 110

Thr Met Val Thr Val Ser Ser
        115

<210> SEQ ID NO 24
<211> LENGTH: 119
<212> TYPE: PRT
<213> ORGANISM: artificial sequence
<220> FEATURE:
<223> OTHER INFORMATION: VH with CDR-H3 = L38-A12

<400> SEQUENCE: 24

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Ala Leu Ser Pro Trp Gly Gln Gly
            100                 105                 110

Thr Met Val Thr Val Ser Ser
        115

<210> SEQ ID NO 25
<211> LENGTH: 119
<212> TYPE: PRT
<213> ORGANISM: artificial sequence
<220> FEATURE:
<223> OTHER INFORMATION: VH with CDR-H3 = L38-G7

<400> SEQUENCE: 25

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95

Thr Arg Thr Ser Leu Met Ser Ile Tyr Phe Asp Tyr Trp Gly Gln Gly
            100                 105                 110

Thr Met Val Thr Val Ser Ser
        115

<210> SEQ ID NO 26
<211> LENGTH: 119
<212> TYPE: PRT
<213> ORGANISM: artificial sequence
<220> FEATURE:
<223> OTHER INFORMATION: VH with CDR-H3 = L39-D11

<400> SEQUENCE: 26

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Thr Arg Ser Gly Leu Leu Phe Leu Tyr Phe Asp Tyr Trp Gly Gln Gly
            100                 105                 110

Thr Met Val Thr Val Ser Ser
        115

<210> SEQ ID NO 27
<211> LENGTH: 119
<212> TYPE: PRT
<213> ORGANISM: artificial sequence
<220> FEATURE:
<223> OTHER INFORMATION: VH with CDR-H3 = E1-37-E7

<400> SEQUENCE: 27

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Gly Leu Ile Asn Leu Gly Met His Pro Trp Gly Gln Gly
            100                 105                 110

Thr Met Val Thr Val Ser Ser
        115

<210> SEQ ID NO 28
```

```
<211> LENGTH: 119
<212> TYPE: PRT
<213> ORGANISM: artificial sequence
<220> FEATURE:
<223> OTHER INFORMATION: VH with CDR-H3 = M1_3-82

<400> SEQUENCE: 28
```

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Ala Leu Arg Asp Trp Gly Gln Gly
            100                 105                 110

Thr Met Val Thr Val Ser Ser
        115

```
<210> SEQ ID NO 29
<211> LENGTH: 119
<212> TYPE: PRT
<213> ORGANISM: artificial sequence
<220> FEATURE:
<223> OTHER INFORMATION: VH with CDR-H3 = Ln4p-23

<400> SEQUENCE: 29
```

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Lys Leu Thr Ser Trp Gly Gln Gly
            100                 105                 110

Thr Met Val Thr Val Ser Ser
        115

```
<210> SEQ ID NO 30
<211> LENGTH: 119
<212> TYPE: PRT
<213> ORGANISM: artificial sequence
<220> FEATURE:
<223> OTHER INFORMATION: VH with CDR-H3 = Ln4p-28

<400> SEQUENCE: 30
```

Glu Val Gln Leu Leu Glu Ser Gly Ala Glu Val Lys Lys Pro Gly Ala
1               5                   10                  15

```
Ser Val Lys Val Ser Cys Lys Ala Phe Gly Tyr Pro Phe Thr Asp Tyr
             20                  25                  30

Leu Leu His Trp Val Arg Gln Ala Pro Gly Gln Gly Leu Glu Trp Val
             35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Ser Gly Leu Ile Asn Leu His Phe Asp Thr Trp Gly Gln Gly
            100                 105                 110

Thr Met Val Thr Val Ser Ser
            115

<210> SEQ ID NO 31
<211> LENGTH: 119
<212> TYPE: PRT
<213> ORGANISM: artificial sequence
<220> FEATURE:
<223> OTHER INFORMATION: VH with CDR-H3 = Ln4p-50

<400> SEQUENCE: 31

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
             20                  25                  30

Leu Leu His Trp Val Arg Gln Ala Pro Gly Gln Gly Leu Glu Trp Val
             35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Thr Arg Ser Thr His Phe Ser Ala Tyr Phe Asp Tyr Trp Gly Gln Gly
            100                 105                 110

Thr Met Val Thr Val Ser Ser
            115

<210> SEQ ID NO 32
<211> LENGTH: 119
<212> TYPE: PRT
<213> ORGANISM: artificial sequence
<220> FEATURE:
<223> OTHER INFORMATION: VH with CDR-H3 = Ln4p-65

<400> SEQUENCE: 32

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
             20                  25                  30

Leu Leu His Trp Val Arg Gln Ala Pro Gly Gln Gly Leu Glu Trp Val
             35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80
```

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
            100                 105                 110

Thr Met Val Thr Val Ser Ser
        115

<210> SEQ ID NO 33
<211> LENGTH: 119
<212> TYPE: PRT
<213> ORGANISM: artificial sequence
<220> FEATURE:
<223> OTHER INFORMATION: VH with CDR-H3 = Ln4p-90

<400> SEQUENCE: 33

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Asn Leu Asn Pro Trp Gly Gln Gly
            100                 105                 110

Thr Met Val Thr Val Ser Ser
        115

<210> SEQ ID NO 34
<211> LENGTH: 214
<212> TYPE: PRT
<213> ORGANISM: artificial sequence
<220> FEATURE:
<223> OTHER INFORMATION: Light Chain 5-306* L-version

<400> SEQUENCE: 34

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 35
<211> LENGTH: 449
<212> TYPE: PRT
<213> ORGANISM: artificial sequence
<220> FEATURE:
<223> OTHER INFORMATION: Heavy Chain with CDR-H3 = 7B1-502*

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Thr Leu Ile Ser Val Tyr Phe Asp Tyr Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 36
<211> LENGTH: 449
<212> TYPE: PRT
<213> ORGANISM: artificial sequence
<220> FEATURE:
<223> OTHER INFORMATION: Heavy Chain with CDR-H3 =7A-701*

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Asn His Met Thr Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 37
<211> LENGTH: 449
<212> TYPE: PRT
<213> ORGANISM: artificial sequence
<220> FEATURE:
<223> OTHER INFORMATION: Heavy Chain with CDR-H3 = L38-A1*

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
                35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Ser Gly Leu Ile Phe Asp Tyr Trp Leu Asp Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 38
<211> LENGTH: 449
<212> TYPE: PRT
<213> ORGANISM: artificial sequence
<220> FEATURE:
<223> OTHER INFORMATION: Heavy Chain with CDR-H3 = L38-A12*

<400> SEQUENCE: 38

Gln Val Gln Leu Val Gln Ser Gly Ala Glu Val Lys Lys Pro Gly Ala

```
1               5                   10                  15
Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
                35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Gly Leu Ile Ile Asp Ala Leu Ser Pro Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

Ala Leu His Asn His Tyr Thr Gln Lys Ser Leu Ser Leu Ser Pro Gly
            435                 440                 445

Lys

<210> SEQ ID NO 39
<211> LENGTH: 449
<212> TYPE: PRT
<213> ORGANISM: artificial sequence
<220> FEATURE:
<223> OTHER INFORMATION: Heavy Chain with CDR-H3 = L38-G7*

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Thr Arg Thr Ser Leu Met Ser Ile Tyr Phe Asp Tyr Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 40
<211> LENGTH: 449
<212> TYPE: PRT
<213> ORGANISM: artificial sequence
<220> FEATURE:
<223> OTHER INFORMATION: Heavy Chain with CDR-H3 = L39-D11*

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 41
<211> LENGTH: 449
<212> TYPE: PRT
<213> ORGANISM: artificial sequence
<220> FEATURE:
<223> OTHER INFORMATION: Heavy Chain with CDR-H3 = E1-37-E7*

<400> SEQUENCE: 41

Gln Val Gln Leu Val Gln Ser Gly Ala Glu Val Lys Lys Pro Gly Ala
1               5                   10                  15
Ser Val Lys Val Ser Cys Lys Ala Phe Gly Tyr Pro Phe Thr Asp Tyr
            20                  25                  30
Leu Leu His Trp Val Arg Gln Ala Pro Gly Gln Gly Leu Glu Trp Val
        35                  40                  45
Gly Trp Leu Asn Pro Tyr Ser Gly Asp Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Gly Leu Ile Asn Leu Gly Met His Pro Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 42
<211> LENGTH: 449
<212> TYPE: PRT
<213> ORGANISM: artificial sequence
<220> FEATURE:
<223> OTHER INFORMATION: Heavy Chain with CDR-H3 = M1_3-82*

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
             85                  90                  95

Ala Arg Ser Gly Leu Ile Phe Asp Ala Leu Arg Asp Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 43
<211> LENGTH: 449
<212> TYPE: PRT
<213> ORGANISM: artificial sequence
```

<220> FEATURE:
<223> OTHER INFORMATION: Heavy Chain with CDR-H3 = Ln4p-23*

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Lys Leu Thr Ser Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 44
<211> LENGTH: 449
<212> TYPE: PRT
<213> ORGANISM: artificial sequence
<220> FEATURE:
<223> OTHER INFORMATION: Heavy Chain with CDR-H3 = Ln4p-28*

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu His Phe Asp Thr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 45
<211> LENGTH: 449
<212> TYPE: PRT
<213> ORGANISM: artificial sequence
<220> FEATURE:
<223> OTHER INFORMATION: Heavy Chain with CDR-H3 = Ln4p-50*

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 46
<211> LENGTH: 449
<212> TYPE: PRT
<213> ORGANISM: artificial sequence
<220> FEATURE:
<223> OTHER INFORMATION: Heavy Chain with CDR-H3 = Ln4p-65*

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
                100                 105                 110

Thr Met Val Thr Val Ser Ser Ala Ser Thr Lys Gly Pro Ser Val Phe
            115                 120                 125
```

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 47
<211> LENGTH: 449
<212> TYPE: PRT
<213> ORGANISM: artificial sequence
<220> FEATURE:
<223> OTHER INFORMATION: Heavy Chain with CDR-H3 = Ln4p-90*

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30
```

-continued

```
Leu Leu His Trp Val Arg Gln Ala Pro Gly Gln Gly Leu Glu Trp Val
         35                  40                  45
Gly Trp Leu Asn Pro Tyr Ser Gly Asp Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Ser Gly Leu Ile Ile Asp Asn Leu Asn Pro Trp Gly Gln Gly
                100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 48
<211> LENGTH: 449
<212> TYPE: PRT
<213> ORGANISM: artificial sequence
<220> FEATURE:
<223> OTHER INFORMATION: Heavy Chain with CDR-H3 = 3077*

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 49
<211> LENGTH: 127
<212> TYPE: PRT
<213> ORGANISM: Homo sapiens
<220> FEATURE:
<223> OTHER INFORMATION: human GM-CSF

<400> SEQUENCE: 49

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 50
<211> LENGTH: 127
<212> TYPE: PRT
<213> ORGANISM: Macaca mulatta
<220> FEATURE:
<223> OTHER INFORMATION: Can also be found in Macaca fascicularis
<220> FEATURE:
<223> OTHER INFORMATION: macaca GM-CSF

<400> SEQUENCE: 50

Ala Pro Ala Arg Ser Pro Ser Pro Gly Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Lys Thr Val Glu Val Val Ser Glu Met Phe Asp
        35                  40                  45

Leu Gln Glu Pro Ser Cys Leu Gln Thr Arg Leu Glu Leu Tyr Lys Gln
    50                  55                  60

Gly Leu Gln Gly Ser Leu Thr Lys Leu Lys Gly Pro Leu Thr Met Met
65                  70                  75                  80

```
Ala Ser His Tyr Lys Gln His Cys Pro Pro Thr Pro Glu Thr Ser Cys
            85                  90                  95

Ala Thr Gln Ile Ile Thr Phe Gln Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 51
<211> LENGTH: 127
<212> TYPE: PRT
<213> ORGANISM: Nomascus concolor
<220> FEATURE:
<223> OTHER INFORMATION: gibbon GM-CSF

<400> SEQUENCE: 51

Ala Pro Ser Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Ile Asn Glu Thr Val Glu Val Val Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
            85                  90                  95

Ala Thr Gln Ile Ile Ile Phe Glu Ser Phe Lys Glu Asn Leu Lys Asp
            100                 105                 110

Phe Leu Leu Val Ile Pro Phe Asp Cys Trp Glu Pro Val Gln Gly
            115                 120                 125

<210> SEQ ID NO 52
<211> LENGTH: 119
<212> TYPE: PRT
<213> ORGANISM: artificial sequence
<220> FEATURE:
<223> OTHER INFORMATION: VH with CDR-H3 7B1-502

<400> SEQUENCE: 52

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Thr Arg Thr Thr Leu Ile Ser Val Tyr Phe Asp Tyr Trp Gly Gln Gly
            100                 105                 110

Thr Met Val Thr Val Ser Ser
            115

<210> SEQ ID NO 53
```

```
<211> LENGTH: 119
<212> TYPE: PRT
<213> ORGANISM: artificial sequence
<220> FEATURE:
<223> OTHER INFORMATION: VH with CDR-H3 3077

<400> SEQUENCE: 53
```

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser
        115

```
<210> SEQ ID NO 54
<211> LENGTH: 107
<212> TYPE: PRT
<213> ORGANISM: artificial sequence
<220> FEATURE:
<223> OTHER INFORMATION: VL 5-306

<400> SEQUENCE: 54
```

Glu Leu Val Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

```
<210> SEQ ID NO 55
<211> LENGTH: 107
<212> TYPE: PRT
<213> ORGANISM: artificial sequence
<220> FEATURE:
<223> OTHER INFORMATION: VL 5-306* V-version

<400> SEQUENCE: 55
```

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

```
Leu Asn Trp Tyr Gln Gln Arg Pro Gly Lys Ala Pro Gln Leu Leu Ile
            35                  40                  45

Tyr Ala Ala Ser Asn Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ser Tyr Ser Met Pro Arg
                 85                  90                  95

Thr Phe Gly Gly Gly Thr Lys Val Glu Ile Lys
            100                 105

<210> SEQ ID NO 56
<211> LENGTH: 10
<212> TYPE: PRT
<213> ORGANISM: artificial sequence
<220> FEATURE:
<223> OTHER INFORMATION: CDR-H3 3077

<400> SEQUENCE: 56

Ser Gly Leu Ile Ala Val Tyr Phe Asp Tyr
1               5                   10

<210> SEQ ID NO 57
<211> LENGTH: 5
<212> TYPE: PRT
<213> ORGANISM: artificial sequence
<220> FEATURE:
<223> OTHER INFORMATION: Discontinuous epitope

<400> SEQUENCE: 57

Arg Arg Leu Leu Asn
1               5

<210> SEQ ID NO 58
<211> LENGTH: 13
<212> TYPE: PRT
<213> ORGANISM: artificial sequence
<220> FEATURE:
<223> OTHER INFORMATION: Discontinuous epitope
<220> FEATURE:
<221> NAME/KEY: VARIANT
<222> LOCATION: 3
<223> OTHER INFORMATION: Xaa = Arg or Gln

<400> SEQUENCE: 58

Gly Leu Xaa Gly Ser Leu Thr Lys Leu Lys Gly Pro Leu
1               5                   10
```